US008828966B2

(12) United States Patent
Mitchell et al.

(10) Patent No.: US 8,828,966 B2
(45) Date of Patent: Sep. 9, 2014

(54) METHOD FOR TREATMENT OF MACULAR DEGENERATION BY MODULATING P2Y12 OR P2X7 RECEPTORS

(76) Inventors: Claire Mitchell, Philadelphia, PA (US); Alan Laties, Philadelphia, PA (US)

( * ) Notice: Subject to any disclaimer, the term of this patent is extended or adjusted under 35 U.S.C. 154(b) by 0 days.

(21) Appl. No.: 13/457,749

(22) Filed: Apr. 27, 2012

(65) Prior Publication Data
US 2012/0264708 A1    Oct. 18, 2012

Related U.S. Application Data

(63) Continuation-in-part of application No. 12/418,328, filed on Apr. 3, 2009, which is a continuation of application No. PCT/US2007/021211, filed on Oct. 3, 2007.

(60) Provisional application No. 61/480,055, filed on Apr. 28, 2011, provisional application No. 60/849,050, filed on Oct. 3, 2006, provisional application No. 60/966,086, filed on Aug. 23, 2007.

(51) Int. Cl.
| | | |
|---|---|---|
| *A61K 31/70* | (2006.01) | |
| *A61K 31/44* | (2006.01) | |
| *A61K 31/185* | (2006.01) | |
| *A61K 31/47* | (2006.01) | |
| *C40B 30/06* | (2006.01) | |
| *C12N 5/07* | (2010.01) | |
| *A61K 31/7076* | (2006.01) | |
| *A61K 31/137* | (2006.01) | |
| *G01N 33/84* | (2006.01) | |
| *A61K 45/06* | (2006.01) | |
| *G01N 33/50* | (2006.01) | |

(52) U.S. Cl.
CPC ............ *A61K 31/137* (2013.01); *A61K 31/7076* (2013.01); *G01N 33/84* (2013.01); *A61K 45/06* (2013.01); *G01N 33/5044* (2013.01)
USPC ............. 514/47; 514/340; 514/576; 514/311; 506/10; 435/375

(58) Field of Classification Search
CPC ........ C07H 19/20; C07H 19/10; C07H 21/00; A61K 31/70; A61K 31/7076; A61K 31/185; A61K 31/12; C07D 413/04; C07D 401/12; C07D 413/14; C07D 231/12; C07D 249/08; A01N 41/04; C07C 49/84; C07C 309/46
USPC ........ 514/47, 340, 576, 311; 506/10; 435/375
See application file for complete search history.

(56) References Cited

U.S. PATENT DOCUMENTS

| 6,207,391 B1 | 3/2001 | Wu | |
|---|---|---|---|
| 6,306,659 B1 | 10/2001 | Parce | |
| 2002/0077270 A1 | 6/2002 | Rosen | |
| 2003/0186981 A1 * | 10/2003 | Duplantier et al. | ............ 514/242 |
| 2005/0171156 A1 * | 8/2005 | Gross et al. | .................... 514/317 |
| 2007/0014833 A1 * | 1/2007 | Milburn et al. | ............... 424/427 |
| 2007/0225217 A1 | 9/2007 | Chappell | |
| 2009/0247483 A1 | 10/2009 | Mitchell | |
| 2010/0267762 A1 | 10/2010 | Boes | |
| 2011/0077248 A1 | 3/2011 | Vu | |

FOREIGN PATENT DOCUMENTS

WO  PCT/US2007/021211   4/2008

OTHER PUBLICATIONS

Mayo Clinic (1998).*
WebMd (2009).*
Al-Awqati, "Chloride Channels of Intracellular Organelles and their Potential Role in Cystic Fibrosis" Biol., 172:245-266 (1992).
Allikmets, R., et al, "A Photoreceptor Cell-Specific ATP-Binding Transporter Gene (ABCR) is Mutated in Recessive Stargardt Macular Dystrophy." Nature Genet., 15, 236-246 (1997).
Altan N, Chen Y, Schindler M, Simon, "Tamoxifen Inhibits Acidification in Cells Independent of the Estrogen Receptor." Proc. Natl. Acad. Sci., 96:4432-4437 (1999).
Ambati et al., "An Animal Model of Age-Related Macular Degeneration in Senescent Ccl-2- or Ccr-2-Deficient Mice." Nat. Med., 9:1390-1397 (2003).
Anderson et al., "Generation of cAMP-Activated Chloride Currents by Expression of CFTR." Science, 2679-682 (1991).
Avila, "Noninvasive Assessment of Aqueous Humor Turnover in the Mouse Eye" Investigative Ophthalmology & Visual Science, 44(2):722-727 (2003).
Bae, "Protein Kinase A Regulates Chloride Conductance in Endocytic Vesicles from Proximal Tubule" Nature, 348:637-639 (1990).
Barrett, "In Proteinases in Mammalian Cells and Tissues" Elsiver/North-Hollard, Biomedical. Press, New York, 220-224 (1977).
Barasch et al., "Thyrotropin Induces the Acidification of the Secretory Granules of Parafollicular Cells by Increasing the Chloride Conductance of the Granular Membrane" J. Cell. Biol., 107: 2137-2147 (1988).
Barasch et al., "Defective Acidification of Intracellular Organelles in Cystic Fibrosis" Nature, 352:70-73 (1991).
Beatty et al., "The Role of Oxidative Stress in the Pathogenesis of Age-Related Macular Degeneration" Surv. Ophthalmol., 45:115-134 (2000).

(Continued)

*Primary Examiner* — Shirley V Gembeh

(74) *Attorney, Agent, or Firm* — Montgomery, McCracken, Walker & Rhoads, LLP

(57) ABSTRACT

Provided is a method of treating or preventing age-related macular degeneration (AMD) in a patient subject to, or symptomatic of the disease, wherein the method comprises restoring normal lysosomal pH ($pH_L$), or acidifying an abnormally elevated $pH_L$, thus decreasing or preventing a damaging accumulation of lipofuscin or waste products in the retinal pigment epithelium (RPE) cells of the eye of the patient. Further, this method is achieved by modulating the action of the P2X7 and/or P2Y12 receptors of the RPE cells, specifically decreasing the acidity ($pH_L$) of the RPE lysosomes by administering selected receptor antagonists affecting the action of the P2X7 and/or P2Y12 receptors of the RPE. Methods for selecting and quantifying the effectiveness of drugs to restore $pH_L$ and determine outer segment clearance rates is also provided using a high through-put screening protocol.

10 Claims, 14 Drawing Sheets

(56) References Cited

OTHER PUBLICATIONS

Beck, "New therapeutic options for lysosomal storage disorders: enzyme replacement, small molecules and gene therapy" Hum. Genet., 121:1-22 (2007).
Ben-Shabat et al., "Biosynthetic studies of A2E, a major fluorophore of retinal pigment epithelial lipofuscin" J. Biol. Chem., 277:7183-7190 (2002).
Berger et al., "Identification and regulation of the cystic fibrosis transmembrane conductance regulator-generated chloride channel" J. Clin. Invest., 88:1422-1431 (1991).
Bergmann et al., "Inhibition of the ATP-driven proton pump in RPE lysosomes by the major lipofuscin fluorophore A2-E may contribute to the pathogenesis of age-related macular degeneration" FASEB. J., 18:562-564 (2004).
Bergmann, "Does A2E, a Retinoid Component Lipofuscin and Inhibitor of Lysosomal Degradative Functions, Directly Affect the Activity . . . " Exp. Eye Res., 72:191-195 (2001).
Biwersi, "Functional CFTR in endosomal compartment of CFTR-expressing fibroblasts and T84 cells" Am. J. Physiol., 266:C149-C156 (1994).
Cai et al., "Dose-dependent effects of the dopamine D1 receptor . . . " J. Pharm. Exp. Ther., 283:183-189 (1997).
Caci et al, "CFTR activation in human bronchial epithelial cells by novel benzoflavone and benzimidazolone compounds" Am. J. Physiol. Lung Cell Mol. Physiol., 285:L180-L188 (2003).
Campochiaro, "The pathogenesis of choroidal neovascularization in patients with aged-related macular degeneration" Mol. Visl., 5:34-38 (1999).
Chen et al., "A mechanism for tamoxifen-mediated inhibition of acidification" J. Biol. Chem., 274:18364-18373 (1999).
Communi, "Closing of a Human Purinergic P2Y Receptor Coupled to Phosphoipase C and Adenylyl Cyclase" J. Biol. Chem., 272:31969-31973 (1997).
Communi et al., "Pharmacological characterization of the human P2Y11 receptor" Br. J. Pharmacol,128:1199-206 (1999).
Cousins, "The Role of Aging, High Fat Diet and Blue Light Exposure in an Experimental Mouse Model for Basal Laminar Deposit Formation" Exp. Eye Res., 75:543-553 (2002).
Cousins et al., "In Macular Degeneration Eds. Penfold & Provis, Springer-Verlag" New York, pp. 167-200, (2005).
Crabb et al., "Drusen proteome analysis: An approach to the etiology of age-related macular degeneration" Proc. Nat. Acad. Sci., USA. 99:14682-14687 (2002).
Curcio, "Basal Linear Deposit and Large Drusen Are Specific for Early Age-Related Maculopathy" Arch. Ophthalmol., 117:329-339 (2009).
Davis-Kaplan, "Chloride is an allosteric effector of copper assembly for the yeast multicopper oxidase Fet3P . . . " Proc. Nat. Acad. Sci., USA, 95:13641-13645 (1998).
DE, "Interaction of A2E with Model Membranes. Implications to the Pathogenesis of Age-Related Macular Degeneration" J. Gen. Physiol., 120:147-157 (2002).
Do, "cAMP-activated maxi-CI channels in native bovine pigmented ciliary epithelial cells" Am. J. Physiol. Cell Physiol., 287, C1003-C1011 (2004).
Dunn et. al., "ARPE-19, a human retinal pigment epithelial cell line with differentiated properties" Exp. Eye Res., 62:155-69 (1996).
Eldred. "Retinal age pigments generated by self-assembling lysosomotropic detergents" Nature. 361:724-726. (1993).
Eldred, "Lipofuscin fluorophore inhibits lysosomal protein degradation and may cause early stages of macular degeneration" Gerontology, 41(Suppl. 2):15-28 (1995).
Eldred, "In the Retinal Pigment Epithelium" Eds. Marmor & Wolfensberger, Oxford, University Press, New York, pp. 651-668 (1998).
Faundez, "Intracellular Chloride Channels: Determinants of Function in the Endosomal Pathway" Science's Stke., 233:re8 (2004).
Feeney-Burns, "Liposuscin of Human Retinal Pigment Epithelium" Am. J. Ophthalmol., 90:783-791 (1980).
Feeney, "Lipofuscin and melanin of human retinal pigment epithelium" Invest. Ophthal. mol. Vis. Sci., 17:583-600 (1978).
Finneman, "Phagocytosis of rod outer segments by retinal pigment, epithelial cells requires avb5 integrin for binding but not . . . " Natl. Acad. Sci., USA, 94:12932-12937 (1997).
Finneman et al., "The lipofuscin component A2E selectively inhibits phagolysosomal degradation of photoreceptor phospholipid by the retinal pigment epithelium" Proc. Natl. Acad. Sci., 99:3842-3847 (2002).
Fleischhauer, "PEG2, + Ca2+, and cAMP mediate ATP activation of C1-channels in pigmented ciliary epithelial cells . . . " Am. J. Physiol. Cell. Physiol. 281: C1614-23 (2001).
Fleischhauer, "Common Actions of Adenosine Receptor Agonists in Modulating Human Trabecular Meshwork Cell Transport" J. Membrane Biol.,193:121-136 (2003).
Fredholm, et al., "Nomenclature and classification of purinoceptors" Pharmacol. Rev., 46:143-156 (1994).
Galietta, "Cell-based assay for high-throughput quantitative screening of CTFR chloride transport agonists" Am. J. Physiol. Cel. Physiol., 281:C1734-42 (2001).
Galietta, "Identification of CTFR activators and inhibitors: chance or design?" Curr. Op. Pul. Med., 4:497-503 (2004).
Geisow, "pH in the endosome: measurements during pinocytosis and receptor-mediated endocytosis" Exp. Cell. Res., 50:36-46 (1984).
Gregory, "Stimulation of A2 Adenosine Receptors Inhibits the Ingestion of Photoreceptor Outer Segments by Retinal Pigmentl . . . " Invest. Ophthalmol. Vis. Sci. 35:819-825 (1994).
Griesenbach et. al., "Advances in cystic fibrosis gene therapy" Curr. Opin. Pulm. Med.,10:542-546 (2004).
Hadjiconstantinou, "A Potential Neurotransmitter in Retina" J. Neurochem., 41:1440-1444 (1983).
Haines, "Complement Factor H Variant Increases the Risk of Age-Related Macular Degeneration" Science 308:419-421 (2005).
Hall. "Kinetic Studies of Rod Outer Segment Binding and Ingestion by Cultured Rat RPE Cells" Exp. Eye Res., 45:907-922 (1987).
Hall et al., "The phagocytosis of rod outer segments is inhibited by drugs linked to cyclic adenosine monophosphate production" Invest. Ophthalmol. Vis. Sci., 34:2392-2401 (1993).
Hara-Chikuma et al., "CIC-3 chloride channels facilitate endosomal acidification and chloride accumulation" J. Biol. Chem., 280:1241-1247 (2005).
Harikumar, "The Lysososmal Proton pump is Electrogenic" Biol. Chem. 258:10403-10410 (1983).
Hayasaka et al., "Degradation of rod outer segment proteins by cathepsin" D. J. Biochem., 78:1365-1367 (1975).
Holz, "Inhibition of Lysosomal Degradative Functions in RPE Cells by a Retinoid Component of Lipfuscin" Invest. Ophthalmol. Vis. Sci., 40:737-743 (1999).
Holz et al., "Fundus autofluorescence and development of geographic atrophy in age-related macular degeneration" Invest. Ophthalmol. Vis. Sci., 42:1051-1056 (2001).
Hoppe, "Oxidized Low Density Lipoprotein-Induced Inhibition of Processing of Photoreceptor Outer Segments by RPE" Invest. Ophthal. Vis. Sci., 42:2714-2720 (2001).
Ida et al., "EST analysis of mouse retina and RPE/choroid cDNA libraries" Mol. Vis., 10:439-444 (2004).
Irons, "Redistribution of Mn++-Dependent Pyrimidine 5'-Nucleotidase (MDPNase Activity During Shedding and Phagocytosis" Invest. Opthalmol. Vis. Sci., 28:83-91 (1987).
Jentsch et al., "Molecular structure and physiological function of chloride channels" Physiol. Rev., 82:503-568 (2002).
Johnson et al.,"The Alzheimer's Abeta-peptide is deposited at sites of complement activation in pathologic deposits associated with aging and age-related macular degeneration" Proc. Natl. Acad. Sci., 99:11830-11835 (2002).
Joseph, "Colocalization of ATP Release sites and Ecto-ATPase Activity at the Extracellular Surface of Human Astrocytes" J. Biol. Chem., 278:23331-233242 (2003).
Karl, "Differential P1-purinergic modulation of human Schlemm's canal inner-walls cells" Am. J. Physiol. Cell Physiol., 288:C784-C794 (2005).

(56) References Cited

OTHER PUBLICATIONS

Kasper et al., "Loss of the chloride channel ClC-7 leads to lysosomal storage disease and neurodegeneration" Embo J., 24:1079-1091 (2005).
Katz et. al., "Influence of early photoreceptor degeneration on lipofuscin in the retinal pigment epithelium" Exp. Eye Res., 43:561-573 (1986).
Kim, "Rpe65 Leu450 Met variant is associated with reduced levels of the retinal levels of the retinal pigment epithelium lipofuscin fluorophores . . . " Proc. Nat. Acad. Sci.,101:11668-116172 (2004).
Kliffen et al., "Morphologic changes in age-related maculopathy" Microsc. Res. Tech., 36:106-122 (1997).
Klinge et al., "What differentiates antiestrogen-liganded vs. estradiol-liganded estrogen receptor action?" Oncol. Res. 4:137-144(1992).
Klein et al., "The relationship of age-related maculopathy, cataract and glaucoma to visual acuity" Invest. Ophthalmol. Vis. Sci., 36:182-191 (1995).
Klein, "Complement Factor H Polymorphism in Aged-Related Macular Degeneration" Science, 308:385-389 (2005).
Klotz, "Adenosine receptors and their ligands" Naunyn Schmied Arch. Pharacol., 362:382-391 (2000).
Kornak et al., "Loss of the ClC-7 chloride channel leads to osteopetrosis in mice and man" Cell, 104:205-215 (2001).
Krogstad et al., "The basis of antimalarial action: non-weak base effects of chloroquine on acid vesicle pH" Am. J. Trop. Med. Hyg. Mar., 36(2):213-220 (1987).
Kuehn, "Gene discovery provides clues to cause of age-related macular degeneration" JAMA., 293:1841-1845 (2005).
Lavail, "Rod Outer Segment Disc Shedding in Relation to Cyclic Lighting" Exp. Eye Res., 23:277-280 (1976).
Lazzaroni et al., "Tamoxifen retinopathy: does it really exist?" Graefes Arch. Clin. Exp. Ophthalmol., 236:669-673 (1998).
Lee et al., "Novel molecular approaches to cystic fibrosis gene therapy" Biochem. J. 387: 1-15 (2005).
Lewis et al. "D1 and functionally selective dopamine agonists as neuroprotective agents in Parkinson's disease" CNS Neurol. Disord. Drug Targets, 5:345-353 (2006).
Leibovich, "Synergistic Up-Regulation of Vascular Endothelial Growth Factor Expression in Murine Macrophages by Adenosine A2A Receptor . . . " Am. J. Pathol., 160:2231-2244 (2002).
Li et al., "The ClC-3 chloride channel promotes acidification of lysosomes in CHO-K1 and Huh-7 cells" Am. J. Physiol. Cell Physiol., 282: C1483-C1491 (2002).
Liu, "Restoration of Lysosomal pH in RPE Cells from Cultured Human and ACCA4-/- Mice: Pharmacologic Approaches and Functional . . . " Invest. Ophthalmol. Vis. Sci., 49:772-780 (2008).
Lu, "Stimulation of the P2Y1 Receptor Up-Regulates Nucleoside-Triphosphate . . . " The American Society for Pharmacology and Experimental Therapeutics, JPET, 323: 157-164 (2007).
Lukacs, "The Cystic Fibrosis Transmembrane conductance Regulator (CFTR) Chloride Conductance Identified by . . . " J. Biol. Chem., 267:14568-14572 (1992).
Lutty et al., "Changes in choriocapillaris and retinal pigment epithelium (RPE) in age-related macular degeneration." Mol Vis., 5:35-38 (1999).
Ma et al., "High-affinity activators of cystic fibrosis transmembrane conductance regulator (CFTR) chloride conductance identified by high-throughput screening" J. Biol. Chem., 277:37235-37241 (2002).
Mahon et al., "Chloroquine causes lysosomal dysfunction in neural retina and RPE: implications for retinopathy" Curr. Eye Res., 28:277-284 (2004).
Mailman et al., "Parkinson's disease and D 1 dopamine receptors" Curr. Opin. Investig. Drugs, 2: 1582-1591 (2001).
Maiti, "Small Molecule RPE65 Antagonists Limit the Visual Cycle and Prevent Lipofuscin Formation" Biochemistry, 45, 852-860 (2006).

Majumdar, "Activation of Microglia Acidifies Lysosomes and Leads to Degradation of Alzheimer Amyloid Fibrils," Mol. Biol. Cell., 18:1490-1496 (2007).
Maminishkis, "The P2Y2 Receptor Agonist INS37217 Stimulates RPE Fluid Transport in Vitro and Retinal Reattachment in Rat" Investment Oopthalmol. Vis. Sci., 43:3555-3566 (2002).
Mata et al., "Biosynthesis of a major lipofuscin fluorophore in mice and humans with ABCR-mediated retinal and macular degeneration" Proc. Nat. Acad. Sci., 97:7154-7159 (2000).
Mata et al., "Delayed dark-adaptation and lipofuscin accumulation in abcr / mice: implications for involvement of ABCR in age-related macular degeneration" Invest. Ophthalmol. Vis Sci., 42:1685-1690 (2001).
McLaren, "Kinetics of Rod Outer Segment Phagocytosis by Cultured Retinal Pigment Epithelial Cells" Invest. Ophthalmal Vis. Sci., 37:1213-1224 (1996).
McLaughlin "Timolol may inhibit aqueous humor secretion by cAMP-independent action on ciliary epithelial cells" Am. J. Physiol. Cell. Physiol., 281:C865-C75 (2001).
Mitchell et al., "Properties of a non-selective high conductance channel in bovine pigmented ciliary epithelial cells" J. Membr. Biol., 150:105-111 (1996).
Mitchell, "Volume-sensitive chloride current in pigmented ciliary epithelial cells: role of phospholipases" Am. J. Physiol. Cell. Physiol., 276:C212-222 (1997).
Mitchell, "A Large-Conductance Chloride Channel in Bovine Pigmented Ciliary Epithelial Cells Activated by GTPγS" J. Membrane Biol., 158:167-175 (1997).
Mitchell, "Release of ATP by a human retinal pigment epithelial cell line: potential for autocrine stimulation through subretinal space" J. Physiol., 534:193-202 (2001).
Mitchell et al., "A3 adenosine receptors regulate Cl—channels of nonpigmented ciliary epithelial cells" Am. J. Physiol., 276:C659-C666 (1999).
Mitchell et al., "Elevated Pressure Triggers a Physiological Release of ATP from the Retina: Possible Role for Pannexin Hemichannels" Purinergic Signal, 4:101-107 (2008).
Moore et al.,"Age-Related Variation in the Hydraulic Conductivity of Bruch's Membrane" Invest. Ophthalmol. Vis. Sci. 36:1290-1297 (1995).
Moriyama, "Internal Anion Binding Site and Membrane Potential Dominate the Regulation of proteins common to extracellular deposits associated with . . . " Biochem. and Biophys. Res. Comm. 149(1):140-144.
Mullins et al., "Drusen associated with aging and age-related macular degeneration contain proteins common to extracellular deposits associated with atherosclerosis, elastosis, amyloidosis, and dense deposit disease" FASEB. J., 14:835-846 (2000).
Noureddin et al., "Ocular toxicity in low dose tamoxifen: a prospective study" Eye. 13:729-733 (1999).
Njus, "Bioenergetics of secretory vesicles" Biochim. Biophys. Acta., 853:237-265 (1986).
Olivier, "Photodegradation Study of a New Activator of the Cystic Fibrosis Chloride Channel, the 6-Hydroxy-10-chlorobenzo . . . " J. Pharmaceut. Sci., 91:324-330 (2002).
Parish et al., "Isolation and one-step preparation of A2E and iso-A2E, fluorophores from human retinal pigment epithelium" Proc. Nat. Acad. Sci., 95:14609-1413 (1998).
Penfold, "Immunological and Aetiological Aspects of Macular Degeneration" Prog. Ret. Eye Res., 20:385-414.
Peterson, "Extracellular ATP Activates Calcium Signaling, Ion, and Fluid Transport in Retinal Pigment Epithelium" J. Neurosci., 17:2324-37 (1997).
Picollo, "Chloride/proton antiporter activity of mammalian CLC proteins ClC-4 and ClC-5" Nature, 436:420-423 (2005).
Pothos et al., Stimulation-dependent regulation of the pH, volume and quantal size of bovine and rodent secretory vesicles J. Physiol., 542:453-476 (2002).
Reigada, "Release of ATP from retinal pigment epithelial cells involves both CFTR and vesicular transport" Am. J. Physiol. Cell. Physiol., 288:C132-C140 (2005).

(56) References Cited

OTHER PUBLICATIONS

Reigada et al., "Release of ATP from retinal pigment epithelial cells involves both CFTR and vesicular transport" Am. J. Physiol. Cell Physiol., 289:C617-C624, (2005).

Reigada, "Stimulation of an a1-adrenergic receptor downregulates ecto-5' nucleotidase activity on the apical membrane of RPE cells" Purinegic Signalling, 2:499-507 (2006).

Reigada et al., "Glutamate acts at NMDA receptors on fresh bovine and on cultured human retinal pigment epithelial cells to trigger release of ATP" J. Physiol., 575:707-720 (2006).

Riese, "Dopamine D1 Stimulation of NA+, K+, C1-Cotransport in Human NPE Cells: Effects of Multiple Horomones" Invest. Ophthalmal. Vis. Sci. 39:1444-1452 (1998).

Roth et al., "Key pathophysiologic pathways in age-related macular disease" Graefes. Arch. Clin. Exp. Ophthalmol., 242:710-716 (2004).

Rubenstein et al., "In Vitro Pharmacologic Restoration of CFTR-mediated Chloride Transport with Sodium 4-Phenylbutyrate in Cystic Fibrosis Epithelial Cells Containing DF508-CFTR" J. Clin. Invest.,100:2457-2465. (1997).

Ryan, "Purinergic regulation of cation condutances and intracellular Ca2+ incultured rat retinal pigment epithelial cells" J. Physiol. 520:745-759 (1999).

Sabirov et al., "Volume-dependent ATP-conductive Large-Conductance Anion Channel as a Pathway for Swelling-induced ATP Release" J. Gen. Physiol., 118:251-266 (2001).

Scheel et al., "Voltage-dependent electrogenic chloride/proton exchange by endosomal CLC proteins" Nature, 436:424-427 (2005).

Schneider, "ATP-dependent Acidification of Intact and Disrupted Lysosomes" J.Biol. Chem., 256:3858-3864 (1981).

Schutt et al., "Ein Retinoidbestandteil von Lipofuszin, A2-E, ist ein Photosensitizer in humanen RPE-Zellen" Ophthalmologe., 97:682-687 (2000).

Schutt et al., "Isolation of intact lysosomes from human RPE cells and effectsof A2-E on the integrity of the lysosomal and other cellular membranes" Graefes. Arch. Clin. Exp. Ophthalmol., 240:983-988 (2002).

Schwiebert, "ATP Release Mechanisms, ATP Receptors and Purinergic Signalling Along the Nephron" Clin. Exp. Pharmacol. Physiol., 28:340-350 (2001).

Seksek et al., "Evidence against Defective trans-Golgi Acidification in Cystic Fibrosis" J. Biol. Chem., 271:15542-15548 (1996).

Shamsi et al., "Inhibition of RPE Lysosomal and Antioxidant Activity by the Age Pigment Lipofuscin" Invest. Ophthalmol., Vis. Sci. 42:3041-3046 (2001).

Smith et al., "The actions of a D-1 agonist in MPTP treated primates show dependence on both D-1 and D-2 receptor function and tolerance on repeated administration" J. Neur. Trans., 109:123-140 (2002).

Sonawane et al., "Chloride Concentration in Endosomes Measured Using a Ratioable Fluorescent CI Indicator" J. Biol. Chem., 277:5506-5513 (2002).

Sparrow, "The Lipofuscin Fluorophore A2E Mediates Blue Light-Induced Damage to Retinal Pigmented Epithelial Cells" Invest. Ophthalmol. Vis. Sci., 41:1981-1989, Jan. 2000.

Sparrow et al., "Involvement of Oxidative Mechanisms in Blue-Light-Induced Damage to A2E-Laden RPE" Invest Ophthalmol. Vis. Sci., 43:1222-1227 (2002).

Sparrow et al., "A2E, a Lipofuscin Fluorophore, in Human Retinal Pigmented Epithelial Cells in Culture" Invest Ophthalmol. Vis Sci., 40(12):2988-2995 (1999).

Sparrow et al., "RPE lipofuscin and its role in retinal pathobiology" Exp. Eye. Res., 80:595-606 (2005).

Stobrawa, "Disruption of ClC-3, a Chloride Channel Expressed on Synpatic Vesicles, Leads to a Loss of the Hippocampus" Neuron, vol. 29: 185-196, Jan. 2001.

Stuchlik et al., "Effect of dopamine D1 receptor antagonist SCH23390 and D1 agonist A77636 on active allothetic place avoidance, a spatial cognition task" Behav. Br. Res., 172:250-255 (2006).

Sullivan, "Identification and Characterization of P2Y2 Nucleotide Receptors in Human Retinal Pigment Epithelial Cells" J. Neurosci. Res., 49:43-52 (1997).

Sun et al., "Stargardt's ABCR is localized to the disc membrane of retinal rod outer segments" Nature. Gen.,17:15-16 (1997).

Sun et al., "Retinal Stimulates ATP Hydrolysis by Purified and Reconstituted ABCR, the Photoreceptor-specific ATP-binding Cassette Transporter Responsible for Stargardt Disease" J. Biol. Chem., 274:8269-8281 (1999).

Tilly, "Cyclic AMP-dependent Protein Kinase Activation of Cystic Fibrosis Transmembrane Conductance Regulator Chloride Channels in . . . " J. Biol. Chem., 267(14):9470-9473 (1992).

Toimela et al., "Effects of tamoxifen, toremifene and chloroquine on the lysosomal enzymes in cultured retinal pigment epithelial cells" Pharmacol. Toxicol., 83:246-251 (1998).

Toimela et al., "Retinal pigment epithelium cell culture as a model for evaluation of the toxicity of tamoxifen and chloroquine" Ophthal. Res., 1:150-153 (1995).

Valverde, "Differential effects of tamoxifen and I- on three distinguishable chloride currents activated in T84 . . . " Pflug. Archiv. Eur. J. Physiol., 425:552-554 (1995).

Van Adelsburg, "Measurement of pH of Intracellular Compartments in Living Cells by Floourescent Dyes" Meth. Enzymol., 172:85-95 (1989).

Van Dyke et al., "Role of CFTR in Lysosome Acidification" Biochem. Biophys. Res. Comm., 184:300-305 (1992).

Van Dyke et al., "cAMP and Protein Kinase A Stimulate Acidification of Rat Liver Endosomes in the Absence of Chloride" Biochem Biophys Res Comm., 222:312-316 (1996).

Van Leeuwen et al., "Is Medication Use Associated with the Incidence of Early Age-Related Maculopathy?" Ophthalmol., 111:1169-1175 (2004).

Versaux-Botteri et al., "Molecular identification of a dopamine D1b receptor in bovine retinal pigment epithelium" Neurosci. Letts., 237:9-12 (1997).

Von Kugelgen, "Molecular pharmacology of P2Y-receptors" Naunyn. Schmied. Arch. Pharmacol., 362:310-323 (2000).

Von Ruckmann et al., "Distribution of pigment epithelium autofluorescence in retinal disease state recorded in vivo and its change over time" Graefes Arch. Clin. Exp. Ophthalmol., 237:1-9 (1999).

Weng et al., "Insights into the Function of Rim Protein in Photoreceptors and Etiology of Stargardt's Disease from the Phenotype in abcr Knockout Mice" Cell., 98:13-23 (1999).

Weng et al., "Oxidant and antioxidant modulation of chloride channels expressed in human retinal pigment epithelium" Am. J. Physiol. Cell. Physiol., 283:C839-C849 (2002).

Wilson, "Adeno-associated Virus and Lentivirus Pseudotypes for Lung-directed Gene Therapy" Proc. Am. Thorac. Soc., 1:309-314 (2004).

Wills et al., "Chloride Channel Expression in Cultured Human Fetal RPE Cells: Response to Oxidative Stress" Invest. Ophthalmol. Vis. Sci., 41:4247-4255 (2000).

Wistow et al., "Expressed sequence tag analysis of human RPE/choroid for the NEIBank Project: Over 6000 non-redundant transcripts, novel genes and splice variants" Mol. Vis., 8:205-220 (2002).

Woll et al., "Fluorescence-optical measurements of chloride movements in cells using the membrane-permeable dye diHMEQ" Pflug. Arch. Eur. J. Physiol., 432:486-493 (1996).

Yang, "Molecular basis of defective anion transport in L cells expressing recombinant forms of CFTR" Human Molecular Genetics., 2(8):1253-1261 (1993).

Yoshikawa, "CLC-3 deficiency leads to phenotypes similar to human neuronal ceroid lipfucsinosis" Genes to Cells, 7:597-605 (2002).

Young et al., "Pathophysiology of age-related macular degeneration" Surv. Ophthalmol., 31:291-306 (1987).

Zhang et al., "Tamoxifen Blocks Chloride Channels: A Possible Mechanism for Cataract Formation" J. Clin. Invest., 94:1690-1697 (1994).

Zhang, "Selective and Protracted Apoptosis in Human Primary Neurons Microinjected with Active Caspase-3, -6, -7, and -8" J. Neurosci., 20(22):8384-8389 (2000).

(56) References Cited

OTHER PUBLICATIONS

Zhang et al., "Oxidant-induced cell death in retinal pigment epithelium cells mediated through the release of apoptosis-inducing factor" J. Cell. Sci., 116:1915-1923 (2003).

Zhang et al., "Stimulation of P2X7 Receptors Elevates Ca2 and Kills Retinal Ganglion Cells" Invest. Ophthalmol. Vis. Sci., 46:2183-2191 (2005).

Zhang, "Balance of purines may determine life or death of retinal ganglion cells as A3 adenosine receptors prevent loss following P2X7 . . . " J. Neurochem., 98:566-575 (2006).

Zhang, "Identification of the A3 adenosine receptor in rat retinal ganglion cells" Molecular Vision,12:937-48 (2006).

Zimmermann, "In Purinergic and Pyraminergic Signalling I: Molecular, Nervous and Urogenitary System Function" Eds. Abbracchio and Williams, Springer-Verlag. New York, pp. 209-250 (2001).

International Search Report for PCT/US2012/035409.

Written Opinion for PCT/US2012/035409.

Yang et al., "Activation of P2X Receptors Induces Apoptosis in Human Retinal Pigment Epithelium," Invest. Ophthalmol. Vis. Sci. Mar. 2011 vol. 52(3), p. 1522-1530.

Reigada et al., "Degradation of extracellular ATP by the retina pigment epithelium." Am. J. Physiol. Cel. Physiol. 2005, Vo. 289(3), p. C617-624.

Bergmann et al., "Inhibition of the ATP-driven proton pump in RPE lysosomes by the major lipofuscin fluorophore A2-E may contribute to the pathogenesis of age-related macular degeneration," FASEB, J. Mar. 2004: 18(3):562-564.

Ueno et al., "Biocompatibility of brilliat blue G in a rat model of subretinal injection." Retina, 2007, vol. 27(4), p. 499-504.

Wallentin, "P2Y12 inhibitors: difference in properties and mechanisms of action and potential consequences for clinical use. "Euro Heart J. 2009, vol. 30, p. 1964-1977.

Kaarinranta et al., "Age-related macular degeneration activation of innate immunity system via pattern recognition receptors." J. Mol. Med (Berl.) 2009, vol. 87(2), p. 117-123.

Carroll et al., "Selective P2X7 receptor antagonists for chronic inflammation and pain." Puringeric Signalling, 2009, vol. 5, p. 63-73.

Michelson, "P2Y12 Antagonism promises and Challenges." Arterioscler. Thromb. Vasc. Biol., 2008, vol. 28, p. s33-s38.

* cited by examiner

A

B

C

METHOD FOR TREATMENT OF MACULAR DEGENERATION BY MODULATING P2Y12 OR P2X7 RECEPTORS

CROSS-REFERENCE TO RELATED APPLICATIONS

This application claims priority to U.S. Provisional Application 61/480,055, filed on May 28, 2011, which is incorporated herein in its entirety. This application is also a Continuation-in-Part of U.S. patent application Ser. No. 12/418,328, filed Apr. 3, 2009, which is a continuation of International Application PCT/US2007/021211, filed on Oct. 3, 2007 and published on Apr. 10, 2008, which claims priority to U.S. Provisional Application 60/849,050, filed on Oct. 3, 2006, and U.S. Provisional Application 60/966,086, filed on Aug. 23, 2007, each of which is incorporated herein in its entirety.

GOVERNMENT INTEREST

This invention was supported in part by funds from the U.S. Government (Department of Health and Human Services Grant No. EY-13434) and the U.S. Government may therefore have certain rights in the invention.

FIELD OF THE INVENTION

The invention relates to treatment of vision loss and retinal diseases, particularly macular degeneration, by modification of the pH of retinal pigment epithelial lysosomes, based upon manipulation of the lysosomal pH.

BACKGROUND

Age-related macular degeneration (AMD) is the leading cause of untreatable vision loss in elderly Americans (Klein et al., *Invest. Ophthalmol. Vis. Sci.* 36:182-191 (1995)). The initial stages of the disease are neither well understood nor currently treatable. The photoreceptors of the retina comprise the rods and cones, each of which is a specialized sensory cell, a bipolar neuron. Each is composed of an inner and an outer region. The cone's outer segment, like that of adjacent rod photoreceptors, consists of a series of stacked cell membranes that are rich in photosensitive pigments. The distal tips of the rod outer segments are intimately associated with the outermost layer of the retina, the pigment epithelium (RPE). The rod outer segments are in a continuous state of flux, wherein new stacks of membrane are added at the base of the outer segment, and old, worn-out stacks of membrane are shed from its distal tip. The shed rhodopsin-laden segments are phagocytosed by cells of the retinal pigment epithelium (RPE) and engulfed by lysosomes, becoming residual bodies in the cytoplasm of the epithelial cells. Daily phagocytosis of spent photoreceptor outer segments is a critical maintenance function performed by the RPE to preserve vision. Aging retinal pigment epithelium (RPE) accumulates lipofuscin, which includes N-retinylidene-N-retinylethanolamine (A2E) as the major autofluorescent component. Additional components include partially degraded lipids and proteins of either photoreceptor or RPE origin which can act as precursors and combine into the lipofuscin complex.

A2E is localized to lysosomes in cultured RPE, as well as in human RPE in situ. Thus, one of the earliest characteristics of the disorder is the accumulation of lipofuscin in the RPE (Feeney-Burns et al., *Am. J. Ophthalmol.* 90:783-791 (1980); Feeney et al., *Invest Ophthalmol Vis. Sci.* 17:583-600 (1978)). A2E, a primary constituent of lipofuscin (Eldred et al., *Nature.* 361:724-726, 1993.)), undermines lysosomal organelles in several ways including by elevating lysosomal pH ($pH_L$) (Eldred et al., *Gerontol.* 2:15-28 (1995); Holz et al., *Invest Ophthalmol Vis. Sci.* 40:737-743 (1999)). As key lysosomal enzymes act optimally in a narrow range of acidic environments, an increase in $pH_L$ reduces their degradative ability. Because of the circadian rhythm of RPE phagocytosis in the eye, a delay in lipid degradation results in a build up of undigested material in RPE after 24 hours. A consequent accumulation of undigested material compromises RPE cells and appears to hasten the development of AMD. In this regard, the restoration of an optimal acidic environment to lysosomes could enhance enzyme activity and slow or stop the progression of AMD.

Dry AMD is characterized by the failure of multiple systems in the posterior eye and is associated with the accumulation of abnormal deposits within and upon Bruch's membrane (Moore et al., *Invest Ophthalmol Vis. Sci.* 36:1290-1297 (1995)), which separates the blood vessels of the choriod from the RPE layer. The RPE sends metabolic waste from the photoreceptors across Bruch's membrane to the choroid. The Bruch's membrane allows 2-way transit; in for nutrients and out for waste. Thus, Bruch's membrane's vital function is to supply the RPE and outer part of the sensory retina with all of their nutritional needs. However, as Bruch's membrane thickens and gets clogged with age, the transport of metabolites is decreased. This may lead to the formation of drusen, which can be seen in the eye as yellow-gray nodules located between the RPE and Bruch's membrane in age-related macular degeneration (Kliffen et al., *Microsc Res Tech.* 36:106-122 (1997); Cousins et al., In *Macular Degeneration* Eds. Penfold & Provis, Springer-Verlag, New York, pp. 167-200, (2005)). Drusen deposits vary in size and may exist in a variety of forms, from soft to calcified. With increased drusen formation the RPE are gradually thinned and begin to lose their functionality. While drusen formation is not necessarily the cause of dry ARMD, it does provide evidence of an unhealthy RPE. There is also a build up of deposits (Basal Linear Deposits or BLinD and Basal Laminar Deposits BLamD) on and within the membrane. Consequently, the retina, which depends on the RPE for its vitality, may be affected and vision problems arise.

While the initial triggers for these changes are not certain, decline in the hydraulic conductivity of Bruch's membrane, decreased choroidal perfusion (Lutty et al., *Mol. Vis.* 5:35 (1999)), environmental and immunologic injury (Beatty et al., *Surv. Ophthalmol.* 45:115-134 (2000); Zhang et al., *J. Cell. Sci.* 116:1915-1923 (2003)), genetic defects (Kuehn et al., *J. Am. Med. Ass.* 293:1841-1845 (2005); Ambati et al., *Nature. Med.* 9:1390-1397 (2003)), and other degenerative diseases (Johnson et al., *Proc. Nat. Acad. Sci. USA* 99:11830-11835 (2002); Mullins et al., *FASEB. J.* 14:835-846 (2000)) may all contribute to the development of the pathology. The identification of lysozyme C and oxidation products of docosahexaenoate in material present between Bruch's membrane and the RPE suggests that the extrusion of material from the lipofuscin-laden RPE contributes to sub-retinal deposit formation (Young et al., *Surv. Ophthalmol.* 31:291-306 (1987); Crabb et al., *Proc. Nat. Acad. Sci. USA.* 99: 14682-14687 (2002)). The correlation between RPE lipofuscin levels and those retinal regions showing the highest degree of atrophy supports the growing concept that lipofuscin is not just an indicator of disease, but rather, is itself a causal factor von Ruckmann et al., *Graefes Arch. Clin. Exp. Ophthalmol.* 237:1-9 (1999); Roth et al., *Graefes. Arch. Clin. Exp. Ophthalmol.* 242:710-716 (2004), suggesting that a reduction in the rate of lipofuscin formation and an enhancement in lysosomal degradative capacity will slow or stop the progression of AMD before substantial degeneration has occurred.

Lipofuscin in the RPE is primarily derived from incomplete digestion of phagocytosed photoreceptor outer segments (Young et al., *Surv. Ophthalmol.* 31:291-306 (1987); Eldred., In *The Retinal Pigment Epithelium*, Eds. Marmor & Wolfensberger, Oxford, University Press, New York, pp. 651-668, (1998)), with rates of formation reduced when photoreceptor activity is diminished (Katz et al., *Exp. Eye. Res.* 43:561-573 (1986); Sparrow et al., *Exp. Eye. Res.* 80:595-606 (2005)). A2E is a key component of RPE lipofuscin, with A2PE, iso-A2E and other related forms present (Eldred et al., supra, 1993; (Mata et al., *Proc. Nat. Acad. Sci. USA* 97:7154-7159 (2000)).

A2E has been identified in post-mortem eyes from elderly subjects, while levels are substantially elevated in Stargardt's disease, characterized by early-onset macular degeneration (Mata et al., supra, 2000). The disease is associated with mutations in the ABCA4 (ABCR) gene, whose product transports a phospholipid conjugate of all-trans-retinaldehyde out of the intradisk space of the photoreceptors (Allikmets et al., *Nature. Gen.* 15:236-246 (1997); Sun et al., *Nature. Gen.* 17:15-16 (1997)). The accumulation of substrate resulting from the transport failure leads to formation of A2PE, which is subsequently delivered to the RPE after the phagocytosis of the outer segments (Sun et al., *J. Biol. Chem.* 274:8269-8281 (1999)). A2PE is cleaved to A2E in the RPE, with small amounts of spontaneous isomerization to iso-A2E occurring (Parish et al., *Proc. Nat. Acad. Sci. USA* 95:14609-1413 (1998); Ben-Shabat et al., *J. Biol. Chem.* 277:7183-7190 (2002)). Measurements from ABCA4$^{-/-}$ mice, developed by Travis and colleagues, have demonstrated that A2E levels are greatly enhanced in the RPE of ABCA4 mutant mice, consistent with the elevated levels of A2E in patients with Stargardt's disease (Mata et al., supra, 2000). In a rate-determining step in the visual cycle, retinaldehyde is reduced to retinol by the enzyme retinol dehydrogenase located in the photoreceptor outer segment. Thus, only the retinaldehyde that escapes conversion to retinol can react with phosphatidylethanolamine, and enter the A2E biosynthetic pathway to generate A2E in a multistep process.

The above-noted localization of A2E predominantly to lysosomes and late endosomes of RPE cells in vitro and in situ, is consistent with the phagolysosomal origins of lipofuscin granules (Holz et al., supra, 1999; Finnemann et al., *Proc. Natl. Acad. Sci. USA* 99:3842-3847 (2002)). As lysosomal organelles in the RPE degrade phagocytosed outer segments, the accumulation of undigested material of outer segment origin in AMD is consistent with a lysosomal dysfunction. Addition of A2E to cultured cells reduces the lysosomal degradation of photoreceptor outer segment lipids (Finnemann et al., supra, 2002), and decreases the pH-dependent protein degradation attributed to lysosomal enzymes (Holz et al., supra, 1999).

The mechanisms by which A2E causes lysosomal damage are influenced by levels of light and A2E itself. At high concentrations, the amphiphilic structure leads to a detergent-like insertion of A2E into the lipid bilayer, with consequent loss of membrane integrity and leakage of lysosomal enzymes (Eldred et al., supra, 1993; Sparrow et al., *Invest. Ophthalmol. Vis. Sci.* 40:2988-2995 (1999); Schutt et al., *Graefes. Arch. Clin. Exp. Ophthalmol.* 240:983-988 (2002)). Low-wavelength light can oxidize lipofuscin and A2E into toxic forms, which rapidly lead to cell death (Sparrow et al., supra, 2005; Sparrow et al., *Invest. Ophthalmol. Vis. Sci.* 41:1981-1989 (2000)). The direct effect on degradative lysosomal enzymes is also dependent on light. While lipofuscin directly decreases the activity of several lysosomal enzymes removed from lysosomes when exposed to light, it had little effect on their activity in the dark (Shamsi et al., *Invest. Ophthalmol. Vis. Sci.* 42:3041-3046 (2001)). The lack of direct effects on lysosomal enzymes in the absence of light treatment has been confirmed by Bermann et al., *Exp Eye Res.* 72:191-195 (2001).

Conversely, however, indirect effects are likely, since A2E interferes with the function of the lysosomal vH$^+$ATPase proton pump (Bergmann et al., *FASEB. J.* 18:562-564 (2004)), and low levels of A2E increased lysosomal pH (Holz et al., supra, 1999). The detected lysosomal pH change indicated that A2E could reduce enzyme effectiveness by alkalinizing the lysosomes. Yet, because this pH-dependent effect occurred at low levels of A2E that had little effect on membrane leakage, the alkalinization apparently preceded acute disruption of membrane integrity.

The modification and degradation of material by lysosomes is essential for cellular function. Lysosomes are characterized by their low pH (4.5-5.0), with optimal enzyme activity dependent on vesicle pH (Geisow et al., *Exp. Cell. Res.* 150:36-46 (1984)). Lysosomes are thought to acidify when positively charged hydrogen ions are pumped across the membrane by an H$^+$-ATPase pump, but the build up of charge limits the degree of acidification. The charge imbalance is overcome by the movement of negatively charged chloride ions into the lysosome through a Cl$^-$ channel. Thus, agents that cause the Cl$^-$ channel to open, lead to further acidification of the lysosome.

The degradation of outer segment proteins of the photoreceptor is primarily mediated by the aspartic protease cathepsin D (Hayasaka et al., *J. Biochem.* 78:1365-1367 (1975)). While its pK$_A$ varies with substrate, the degradative activity of cathepsin D is generally optimum near pH 4, and falls below 20% of maximum at pH>5.0 (Barrett, In *Protinases in Mammalian Cells and Tissues*, Elsiver/North-Hollard, Biomedical. Press, New York, pp. 220-224 (1977)). Rats treated with chloroquine, which is known to alkalinize lysosomes (Krogstad et al., *Am. J. Trop. Med. Hyg.* 36:213-220 (1987)), doubled the number of outer segment-derived lysosome-associated organelles in the RPE (Mahon et al., *Curr. Eye. Res.* 28:277-284 (2004)), leading to the finding that lysosomal alkalization by A2E contributes to the accumulation of lipofuscin in the AMD. However, pharmacologic restoration in a disorder that progresses over decades can be fully realized only when the mechanisms controlling lysosomal pH are understood. Thus, the present invention serves an important function by meeting this need.

Lysosomal vesicle acidification is regulated by a series of membrane proteins, with proton delivery to lysosomes and late endosomes primarily mediated by the vacuolar proton pump (vH$^+$ATPase). The transport of protons by vH$^+$ATPases creates both a proton gradient and an electrical potential across vesicular membranes (Schneider D L., *J. Biol. Chem.* 256: 3858-3864, 1981; (Faundez et al., *Science's Stke.* 233: re8 (2004)). While the activity of vH$^{++}$ATPase in these vesicles is frequently constitutive, the conductance through CV channels is regulated (Hara-Chikuma et al., *J. Biol. Chem.* 280:1241-1247 (2005); Barasch et al., *J. Cell. Biol.* 107: 2137-2147 (1988); Sonawane et al., *J. Biol. Chem.* 277:5506-5513 (2002)).

Thus, a need has remained in the art, until the present invention, to find a way to slow the progression of AMD, particularly by regulating the acidity of the lysosomes within the RPE cells.

SUMMARY OF THE INVENTION

The present invention provides a method for slowing the progression of AMD by restoring an optimal acidic pH to pH-compromised lysosomes in the RPE, and identifies compounds that lower lysosomal pH and increase the activity of degradative enzymes. Treatment of the RPE cell, such as by administering exogenous compositions to modulate lysosomal acidity ("lysosomal pH" ($pH_L$)), modulates a series of second messenger responses, which result in lysosomal acidification or restore acidity of lysosomes within the RPE cell. Therefore, by combining a mechanistic analysis of lysosomal acidification with a high through-put evaluation of the pharmacologic approach and the application of these findings to animal models, the present invention has determined methods for regulating lysosomal pH ($pH_L$) in the RPE cells. Moreover, since the entry of into the lysosomal lumen electrically balances the accumulation of protons, regulation of the channels of the RPE offers a further rate-limiting step in vesicle acidification, and thus, is associated with the development of the pathology.

It is, therefore, an object of the invention to provide methods of pharmacologic manipulation to restore a perturbed lysosomal pH and enhance degradative ability in RPE cells. The absolute value over which the defect occurs in the RPE cells of $ABCA4^{-/-}$ mice (animal model of AMD) is highly relevant to the determination of how to change $pH_L$ and how to quantify that change. In AMD models the RPE cells are gradually lost over time along with a secondary loss of photoreceptors. One method of regulating lysosomal $pH_L$ in the RPE cells is provided by inhibiting the action of compositions that otherwise inhibit acidification of the lysosomes and/or decrease the activity of the degradative enzymes, as measured in both cultured RPE cells, and in defective RPE cells from $ABCA4^{-/-}$ model animals. Thus, an effective treatment is provided by the present invention for reversing the abnormally elevated $pH_L$ associated with macular degeneration, particularly for the macular degeneration found in AMD and in Stargardt's disease, and for restoring the damage caused by the increased $pH_L$ in the patient's eye. As a result, the photoreceptors repopulate toward normality (meaning photoreceptor levels are restored, preserved or maintained to levels comparable to levels and activity found in a normal eye that is not affected by AMD, i.e., when RPE lysosomal $pH_L$ is not abnormally elevated).

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended drawings. It should be understood, however, that the invention is not limited to the precise arrangements and instrumentalities shown.

FIG. 2A shows that A2E (14 nM)±LDL elevated $pH_L$, but LDL itself had an effect. pH is normalized to the mean control of each week (n=8). FIG. 2B shows that incubation with tamoxifen (Tmx) raised $pH_L$. Symbols are mean±SEM fit with a single exponential curve (all n=30, all diff from 0 mM, p<0.001). FIG. 2C shows that the effect of tamoxifen was neither mimicked not inhibited by 17-β-estradiol (17-β, n=6). FIG. 2D shows that tamoxifen and chloroquine (CHQ) slowed clearance of outer segments labeled with calcein after 24 hrs. n=12 for all.

FIG. 3A shows that nonselective adenosine receptor agonist NECA reversed lysosomal alkalinization by tamoxifen in ARPE-19 cells (n=16-63, p always vs. Tmx alone) FIG. 3B shows that $A_1$ agonists CPA and ENBA had no effect (n=8), while in FIG. 3C, $A_{2A}$ adenosine receptor agonist CGS21680 inhibited the effect of tamoxifen (n=22-71) in ARPE-19 cells. FIG. 3D shows $A_{2A}$ receptor expression in ARPE-19 cells and post-mortem human RPE cells by RT-PCR of expected 473 bp. No bands were seen without reverse transcriptase (-). FIG. 3E shows that tamoxifen increased $pH_L$ in primary cultures of bovine RPE cells. Adenosine acidified the lysosomes, although the decrease by NECA was not quite significant (n=4).

FIG. 4A shows that adrenoceptor agonists norepinephrine (Nor) and epinephrine (Epi) and isoproterenol (Iso) helped restore $pH_L$ raised by tamoxifen (n=20-45). FIG. 4B shows that the acidification by norepinephrine was blocked by the β-adrenoceptor inhibitor, timolol (Tim, n=8). FIG. 4C shows that norepinephrine also acidified cells exposed to chloroquine (CHQ, n=20). FIG. 4D shows that cell permeant cAMP analog cpt-cAMP acidified the cells exposed to 10 and 30 μM tamoxifen (n=22-88).

FIG. 5A shows that CFTR agonist genistein (Gen) restored acidity, while antagonist glybenclamide (Glyb) increased $pH_L$ in cells exposed to tamoxifen (n=10-38). FIG. 5B shows that genistein and glibenclamide had smaller effects on control cells (n=7-38; note scale). FIG. 5C shows that $pH_L$ was lower in cells transfected with CFTR; and that control transfection agents had no effect (n=3-4, confirming 3 other trials). FIG. 5D is a Western blot with monoclonal antibody M3A7, showing an increased band at 180 kD protein 48 hours after transfection with CFTR. By comparison, the band is faint in untransfected cells at this exposure. FIG. 5E shows that $NH_4Cl$ (10 mM) increased the 340/380 ratio in isolated lysosomes loaded with Lysosensor dye, consistent with an increase in pH.

FIG. 6A shows that $A_{2A}$ adenosine receptor agonist CGS21680 (CGS) reduced the lysosomal alkalinization induced by chloroquine (CHQ) in ARPE-19 cells. FIG. 6B shows the effect of restoring lysosomal pH on the activity of lysosomal enzymes, as quantified by measuring clearance of fluorescently labeled rod outer segments. ***p<0.001 vs Control, *p<0.05 vs CHQ alone, n=6 for all.

FIG. 7A shows that CFTR-specific antagonist—CFTR-172 (n=32) increased lysosomal pH, verifying a role for CFTR in maintaining $pH_L$. FIG. 7B shows that the newly developed CFTR activator—CFTR$_{Act16}$ (Act16) restored acidity in cells exposed to tamoxifen (TMX, n=6 for all).

FIG. 11A shows that pH$_L$ was increased in RPE cells from ABCA4$^{-/-}$ mice (n=6 trials, from 26 mice aged 216±28 days) compared to cells from wild type mice (n=7 trials, from 22 mice aged 215±32 days). FIG. 11B shows that lysosomal pH increases with the age of ABCA4$^{-/-}$ mice (n=4, 2 mice each, MO=months old). FIG. 11C shows that dopamine D1-like receptor agonists A68930 and A77636 decreased lysosomal pH of ARPE-19 cells treated by tamoxifen (n=8). FIG. 11D shows that dopamine D1-like receptor agonists A68930 and A77636 decreased pH$_L$ of RPE cells from 11-month-old ABCA4$^{-/-}$ mice (n=8). In FIG. 11D, values are given as the ratio of light excited at 340 to 380 nm, an index of lysosomal pH. *=p<0.05, =p<0.01, *=p<0.001 vs control. Bars=mean±SEM.

In FIG. 13A, stimulation of the P2X7 receptor with agonist BzATP is seen to elevate the lysosomal pH$_L$, while administering the P2X7 antagonists A438079 and BBG reduced pH$_L$ and the enhanced autofluorescence. FIG. 13B shows that outer-segment-associated autofluorescence in ARPE-19 cells is decreased in the presence of P2X7 antagonist, A438079 and BBG, as seen in FACS analysis of autofluorescence readouts from ARPE-19 cells excited at 488 nm. Treating the cells for 7 days with 10 μM chloroquine (CHQ) increased autofluorescence, as did feeding the cells with photoreceptor outer segments (POS) for 7 days. FACS analyses were conducted of autofluorescence readouts from ARPE-19 cells excited at 488 nm. FIG. 13C shows that BzATP reduced lysosomal enzyme activity. Cathepsin-D activity in ARPE-19 cells, monitored with a fluorescent reporter, was visibly decreased by the addition of BzATP.

FIG. 14A is a Western blot indicating that stimulating ARPE-19 cells with P2X7 receptor agonist BzATP leads to a rapid increase in LC3B and P62. FIG. 14B provides graphs showing quantification of the effect of treatment with BzATP on the cells, confirming rapid increases in LC3BII and p62, consistent with an increase in lysosomal pH triggered by BzATP.

DETAILED DESCRIPTION OF CERTAIN EMBODIMENTS OF THE INVENTION

While the identification of compounds that can acidify defective lysosomes has direct implications for the health of RPE cells, the development of optimal treatments requires an understanding of the mechanisms controlling pH$_L$. There are many different receptors for ATP each with different effects. Elevation of the lysosomal pH, results in impaired degradation of material by lysosomes, leading to pathological consequences both to the RPE cell and to the immediate area adjacent thereto. As a result, to slow the progression of AMD, particularly by regulating the acidity of the lysosomes within the RPE cells, involves regulation by a series of membrane proteins, with proton delivery primarily mediated by the vacuolar proton pump (vH+ATPase). Re-acidification of pH-compromised lysosomes can rectify an elevated lysosomal pH in RPE cells, and restore or enhance their essential degradative function. However, it has been further determined that stimulation of the P2X7 and P2Y12 receptors has a converse effect, thereby elevating lysosomal pH$_L$ in RPE cells.

The P2Y12 and P2X7 receptors are present on the plasma membrane, meaning that when the RPE cells are treated, second messengers are activated, which travel through the cytoplasm to the lysosomal membrane. Stimulation of the P2Y12 receptors and/or the P2X7 receptors thus activates transport mechanisms located on the lysosomal membrane. This is distinct from modulating cellular or cytoplasmic pH. In this situation, lysosomal pH$_L$ is modified or modultated via the cytoplasmic messengers—but without affecting cytoplasmic pH. Similarly, mere alteration of the RPE cytoplasmic pH, has no effect on the membrane bound lysosomes that are sequestered from the cytoplasm. The drugs being administered do not usually pass the plasma membrane, but do affect the receptors thereon.

Conversely, as is further shown by the data presented herein, administering "antagonists" to the P2X7 receptor, or alternatively to the P2Y12 receptor, effectively re-acidifies lysosomal pH$_L$ in the RPE cells to normal or expected levels, as compared to high pH$_L$. levels seen in pH-compromised lysosomes of diseased RPE cells, such as in age-related macular degeneration. As a result, as further demonstrated, administration of an antagonist either to the P2X7 receptor or to the P2Y12 receptor enhances degradative function of RPE lysosomes, and thus provides an alternative to treatment for macular degeneration, and/or offers an element in a combined treatment therefor involving modulation of an endogenous agonist or of the receptors themselves. The endogenous agonist to the P2X7 receptor is ATP, while the endogenous P2Y12 agonist is ADP.

Figure 1:
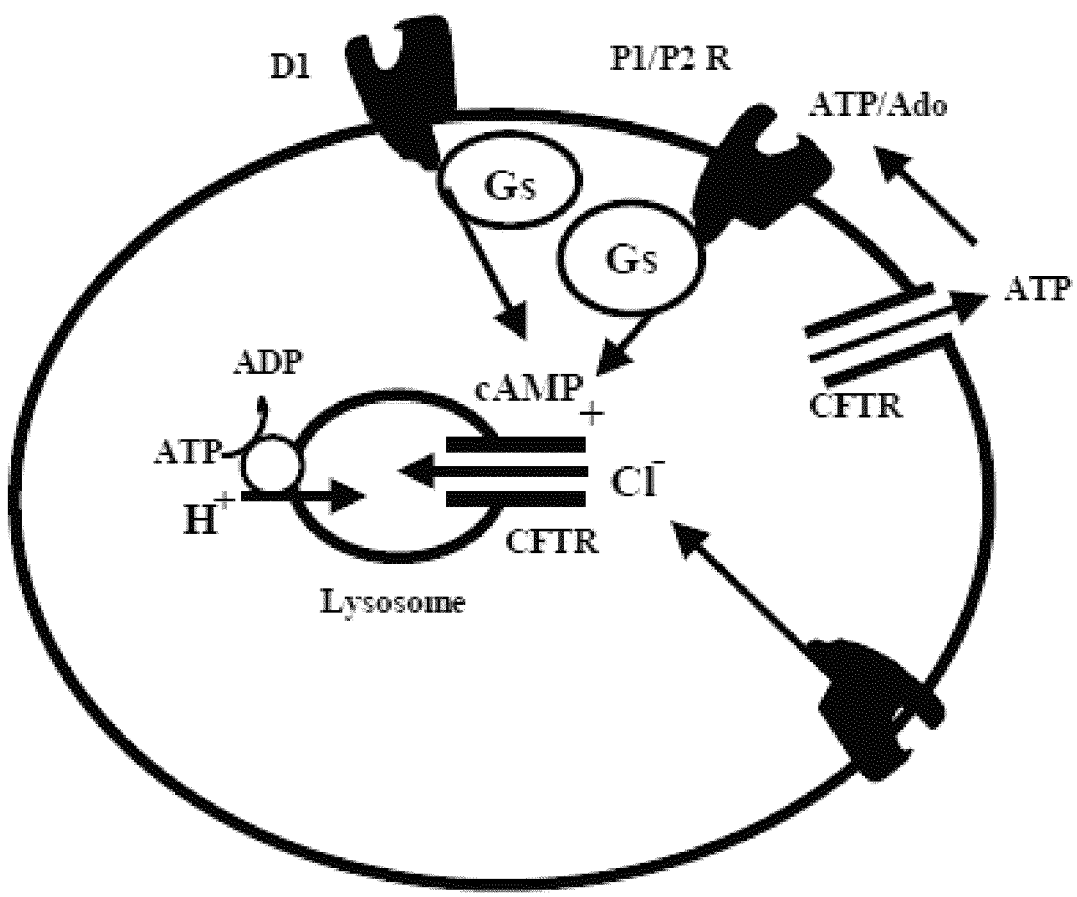
FIG. 1 diagrammatically summarizes an embodiment of the invention, showing that because channel conductance is a rate limiting step in lysosomal vesicular acidification, increasing channel activity will lower pH and enhance enzyme activity. The conductance can be opened by elevating cAMP following stimulation of $G_s$-linked receptors in addition to other mechanisms. CFTR may function on the lysosomes and/or provide a source of purines for receptor-mediated action.

Because Cl⁻ conductance is a prime target for manipulating lysosomal acidity, the recognition of Cl⁻ influx as a rate limiting step in vesicular acidification led to the determination that increasing Cl⁻ channel activity could acidify lysosomes regardless of the original source of pathology. Thus, embodiments of the present invention are directed to Cl⁻ channels of the ocular lysosomal epithelia that are most readily manipulated with the aim of developing treatment for the earliest stages of AMD. FIG. 1 summarizes the invention as embodied when activation of Cl⁻ channels restores the pH of lysosomes that have been alkalinized by A2E in the early stages of macular degeneration. Restoration increases activity of degradative enzymes and slows the rate of lipofuscin accumulation.

Further embodiments of the invention focus on the absolute values of the abnormally elevated $pH_L$ in the defective lysosomes in the RPE cells of a patient with AMD or Stargardt's disease, thus permitting correction of the pH to normal levels, restoring the damage associated with macular degeneration. Further, specific drugs are identified in this invention by combining a mechanistic analysis of lysosomal acidification with a high through-put evaluation of this pharmacologic approach. Thus, methods are provided in the present invention for slowing the progression of macular degeneration, specifically AMD and Stargardt's macular degeneration, by restoring an optimal acidic pH to compromised lysosomes in the RPE of the patient's eye.

Elevation of Lysosomal pH in RPE Cells

Measuring Lysosomal pH: In an embodiment of the invention, drugs were identified that lowers lysosomal pH ($pH_L$), recognizing the importance of acidic lysosomal pH for the degradative functions of the RPE and that $pH_L$ may be elevated by A2E in early AMD. This required the development of an efficient protocol to screen $pH_L$. Traditional dyes have used fluorescence intensity as an index of pH. However, the ratiometric qualities of Lysosensor Yellow/Blue fluoresced yellow, making readings possible that are independent of dye concentration, providing a clear advantage in acidic organelles, like lysosomes, where the volume fluctuates with the pH (Pothos et al., *J. Physiol.* 542:453-476 (2002); Li et al., *Am. J. Physiol. Cell. Physiol.* 282:C1483-C1491 (2002)).

ARPE19 is a spontaneous, immortalized RPE cell line obtained initially from a single human donor, now available at ATCC. Due to its immortality, this cell line has been studied extensively over the last decade to obtain important insights into RPE cell biology. See, e.g., Dunn et al., *Exp. Eye Res.* 62:155-69 (1996)). As a result, experiments in ARPE-19 cells were used to verify the source of the signal from Lysosensor Yellow/Blue and to optimize recording conditions.

Lysosensor Yellow/Blue co-localized with the Lysotracker Red dye in small vesicles, with a distribution consistent with lysosomal origin. Measurements of $pH_L$ were performed using a high throughput screening (HTS) protocol to maximize output and minimize variation using ARPE-19 cells in 96 well plates. HTS assays are particularly useful in the present invention because of the ability to screen hundreds, thousands, and even millions of compounds in a short period of time. Loading for 5 min. at 23° C. with 5 µM lysosensor, followed by 15 min. for internalization, produced stable and reproducible results.

The ratio of fluorescence (em>527 nm), typically excited at 340 nm and 380 nm, was measured for 20 msec, every 30 seconds, to minimize bleaching, and to determine the response to NH₄Cl. The ratio was converted to pH by calibrating with KCl buffered to pH 4.0-6.0 in the presence of monensin and nigericin. Calibration indicated a baseline pH of 4.4 to 4.5, supporting lysosomal localization. NH₄Cl (10 mM) increased fluorescence excited at 340 nm, increasing ratios (pH was elevated by 10 mM NH₄Cl (n=20, p<0.0001)), by the vH⁺ATPase inhibitor bafilomycin-A (pH was elevated by 200 nM BAF (n=20, p<0.0001)) and by chloroquine (pH was elevated by 20 µM CHQ (n=20, p<0.0001)), as expected. NH₄Cl decreased the ratios slightly at 380 nm. Nevertheless, absent the addition of the dye, none of these compounds, or any others, altered the fluorescent signal at 340 or 380 nm, showing a specificity of the measured change to $pH_L$. Thus, these results validate the use of the Lysosensor probe to measure $pH_L$ using high through-put screening methods and demonstrate that changes in $pH_L$ are reliably quantified. This quantification is necessary to predict the potential effectiveness of acidifying drugs to restore lysosomal enzyme activity.

When a population or subpopulation is found to contain a compound having desired properties, the screening step may be repeated with additional subpopulations containing the desired compound until the population has been reduced to one or a sufficiently small number to permit identification of the compound desired. Standard HTS assays may be miniaturized and automated, e.g., by replacing the standard 96-well plate with a 1536-well plate permitting the easy assay of up to 1500 different compounds. See, e.g., U.S. Pat. Nos. 6,306,659 and 6,207,391. Any suitable HTS system can be used in practicing the invention, and many are commercially available (see, e.g., LEADseeker™, Amersham Pharmacia Biotech, Piscataway, N.J.; PE Biosystem FMAT™ 8100 HTS System Automated, PE Biosystem, Foster City, Calif.; Zymark Corp., Hopkinton, Mass.; Air Technical Industries, Mentor, Ohio; Beckman Instruments, Inc. Fullerton, Calif.; Precision Systems, Inc., Natick, Mass., etc.).

The primary trigger for lysosomal alkalinization in RPE cells with macular degeneration is likely A2E. However, the efficient screening for compounds able to restore lysosomal function requires a rapidly-acting alkalinizing agent with similar mode of action that can also reduce the rate of outer segment clearance. When tested, A2E increased $pH_L$ in ARPE-19 cells by 0.4 units.

Holz and colleagues previously reported A2E responses, but the increase in $pH_L$ required four weeks of feeding the cells with A2E (14 nM) every 3-4 days, and the A2E was complexed to low-density lipoprotein (LDL; 10 µg/ml) (Holz et al., supra, 1999). However, as determined in the present study, complexing A2E to LDL did not enhance the effect of A2E in the current trials. In fact, as shown in FIG. 2A, the LDL itself had an alkalinizing effect. To reduce the lengthy time course, higher concentrations of A2E (100 nM) were tested, but the cells were killed over a period of 1-2 weeks. Therefore, alternative methods were needed to permit timely testing of the effect of pH on lysosomal activity in the RPE cells.

Therefore, in an embodiment of the invention, the testing process was significantly advanced when it was determined that tamoxifen rapidly elevated lysosomal pH, with levels reaching a plateau within 10-15 minutes (establishing the time point used in all subsequent measurements). This rapid (<10-15 minute) alkalinization of the RPE cells established a high $pH_L$ on which test compounds could be tested for their ability to modulate the pH, as compared with the 4-week, prior art time course of A2E-mediated alkalinization which had been used to achieve similar results. The rise in pH by the present method for increasing $pH_L$ was concentration dependent, with $EC_{50}$=22 µM (FIG. 2B). The "rapid-acting" increase in $pH_L$ produced by 15 µM tamoxifen (produced in <10-15 minutes) was equivalent to that which resulted from the long time course of A2E-mediated alkalinization (14 nM).

The response to tamoxifen was reversed by the channel blocker 5-nitro-2-(3-phenylpropylamino)-benzoate ("NPPB"), but was neither mimicked, nor inhibited, by 17-β estradiol (FIG. 2C), indicating that the effect of tamoxifen did not involve estrogen receptors or blockage of Cl⁻ channels (Klinge et al., *Oncol. Res.* 4:137-144 (1992); Zhang et al., *J. Clin. Invest.* 94:1690-1697 (1994); Valverde et al., *Pflug. Archiv. Eur. J. Physiol.* 425:552-554 (1993). Tamoxifen slowed the degradation of outer segments at rates approaching chloroquine (FIG. 3D). The reduction in the clearance of outer segments was dose-dependent and proportional to the effect of tamoxifen on $pH_L$, supporting the theory that the two are linked. As a result, although A2E and tamoxifen both elevated the $pH_L$ of RPE cells, the discovery of the significantly more rapid action resulting from the use of tamoxifen made this manipulation suitable for rapid screening assays.

High through-put screening methods involve providing a library containing a large number of potential therapeutic compounds ("candidate" or "test" compounds) that may be modulators of lysosomal acidity. Libraries of candidate compounds ("combinatorial libraries") can be screened using one or more assays of the invention, as described herein, to identify those library compounds that display the desired characteristic activity, e.g., modulation of lysosomal activity. A higher or lower level of $pH_L$ in the presence of the test compound, as compared with $pH_L$ in the absence of the test compound, is an indication that the test compound affects $pH_L$, and therefore, that it also modulates lysosomal activity.

The results are consistent with previous reports, further confirming that tamoxifen alkalinizes lysosomes through a detergent-like action (Chen et al., *J. Biol. Chem.* 274:18364-18373 (1999); Altan et al., *Proc. Nat. Acad. Sci. USA* 96:4432-4437 (1999)). While the incidence of retinopathies with moderate doses of tamoxifen treatment are low, the problems that occur at higher doses are consistent with increased $pH_L$ in the RPE (Lazzaroni et al., *Graefes. Arch. Clin. Exp. Ophthalmol.* 236:669-673 (1998); Noureddin et al., *Eye.* 13:729-733 (1999)). The decrease in outer segment clearance in the presence of tamoxifen and/or chloroquine supports the dependence of degradative capacity on $pH_L$, although a direct effect of tamoxifen on lysosomal enzymes may also contribute to the overall effect (Toimela et al. *Pharmacol. Toxicol.* 83:246-251 (1998); Toimela et al., *Ophthal Res.* 1:150-153 (1995)). Moreover, these experiments demonstrate the feasibility of measuring both $pH_L$ and outer segment clearance using the high through-put screening protocol of the present invention, wherein quantifying the effectiveness of drugs to restore $pH_L$ and clearance rates is needed.

Receptor-Mediated Restoration of $pH_L$.

Adenosine Lowers $pH_L$: Because identifying a drug capable of acidifying distressed lysosomes in RPE cells holds therapeutic potential for treating AMD, the effect of purinergic signaling to RPE physiology was determined. The present findings demonstrated that purines can be used to restore $pH_L$. Low doses of adenosine and the stable adenosine receptor agonist 5'-(N-ethylcarboxamido) adenosine (NECA) were independently administered to the RPE cells and found to reduce the $pH_L$ in cells treated with tamoxifen when each compound was given 15 minutes before measurements were made. A delivery for "prolonged period" of time for the purposes of this invention means ≥1 hour; ≥12 hours, ≥18 hours, ≥24 hours, 1-3 days, 1-7 days, ≥1 week, ≥1-2 weeks, to 1 month or more. However, the response to adenosine was more variable (FIG. 3A) than the effect of NECA. While not wishing to be bound by any theory, this is likely because at low concentrations, NECA activates both $A_1$ and $A_{2A}$ adenosine receptors (Fredholm et al., *Pharmacol. Rev.* 46:143-156 (1994)).

As used herein, and as accepted in the art, an "agonist" composition, when administered to a cell, such as an RPE cell or administered in vivo to the cells of a patient, enhances, extends or increases a biological activity, such as the activity of the specified receptor, attributable to the presence of, or level or changes in the level of, an endogenous composition, gene, receptor or component in the cell or in a cell in the patient system. Conversely, an "antagonist" composition, when administered to a cell, such as an RPE cell or administered in vivo to the cells of a patient, inhibits, decreases, diminishes, or may even prevent, a biological activity, such as the activity of the specified receptor, attributable to the presence of, or level or changes in the level of, an endogenous composition, gene, receptor or component in the cell or in a cell in the patient system. Recent evidence has shown that the effect may not always be as direct as previously assumed, and in some cases the effect crosses-over and may be seen in adjacent parts of the cell.

Agonists for the $A_1$ adenosine receptor $N^6$-cyclopentyladenosine (CPA) and $(2S)-N^6$-[2-endo-norbornyl]adenosine (ENBA) had no effect (see, FIG. 3B), the $A_{2A}$ receptor agonist, CGS21680, acidified the lysosomes at levels found previously to be specific ((Mitchell et al., *Am. J. Physiol. Cell. Physiol.* 276:C659-C666 (1999)); FIG. 3C). Over half of the increase triggered by 10 μM tamoxifen was reversed by CGS21680, demonstrating that the compound would largely restore lysosomal acidity to cells challenged with A2E. Message for the $A_{2A}$ adenosine receptor was identified in both ARPE-19 cells and fresh human RPE cells with RT-PCR (FIG. 3D). NECA and adenosine also decreased $pH_L$ in primary cultures of bovine RPE cells treated with tamoxifen (FIG. 3E). PCR techniques in general are described, for example, in *PCR Protocols*, Innis et al., eds., Academic Press, Inc., San Diego, Calif. (1990).

Consequently, it was determined that stimulation of adenosine receptors did, in fact, restore $pH_L$ in cells treated with tamoxifen, and likely involves the $A_{2A}$ receptor. The acidification of $pH_L$ in bovine cells treated with tamoxifen further showed that the responses to tamoxifen are neither species specific, nor restricted to a particular cell line.

Figure 4:
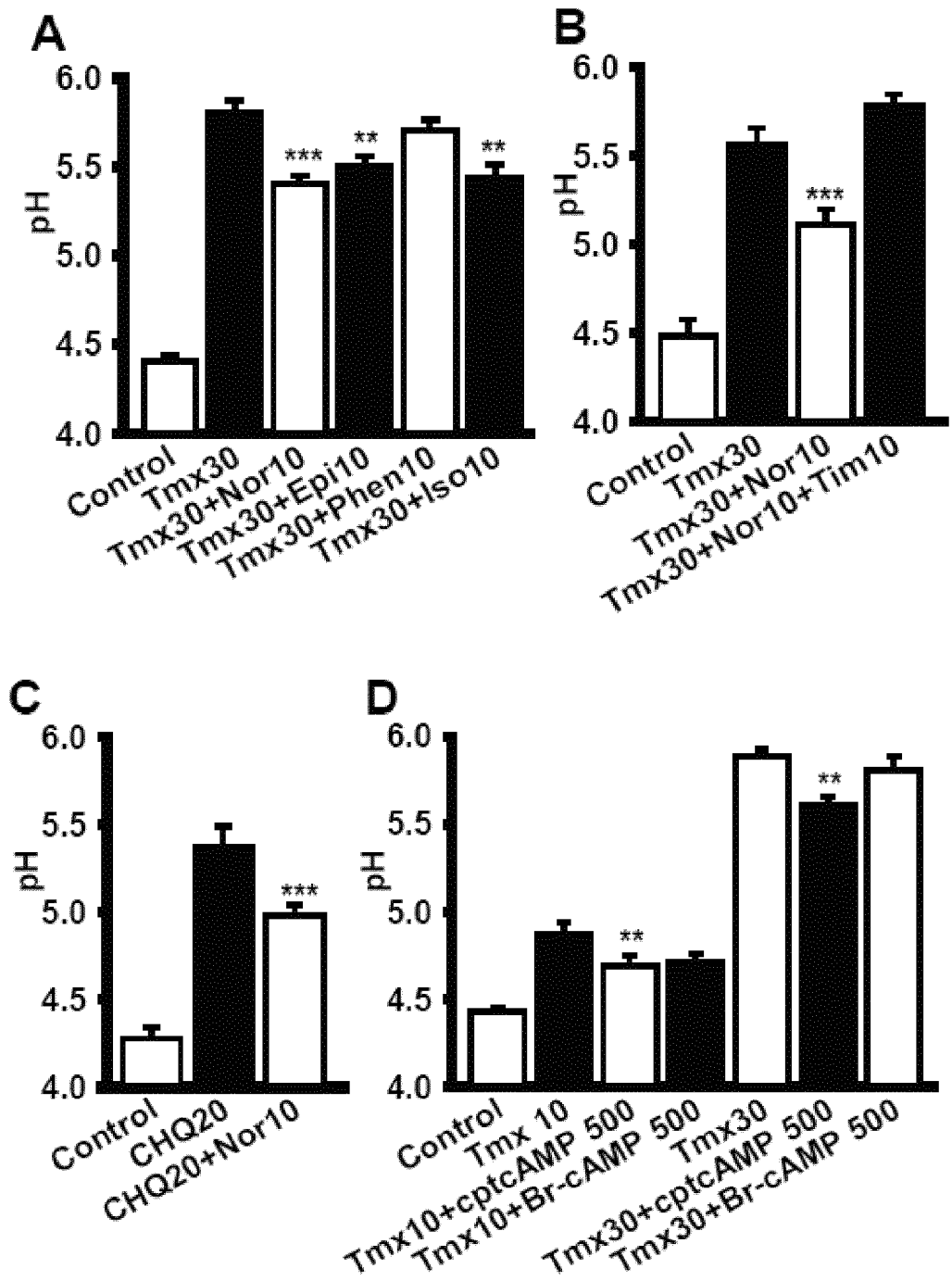
FIGS. 4A-4D are graphs showing the effect of adrenoceptor agonists and cAMP lower $pH_L$ in ARPE-19 cells.
Figure 9:
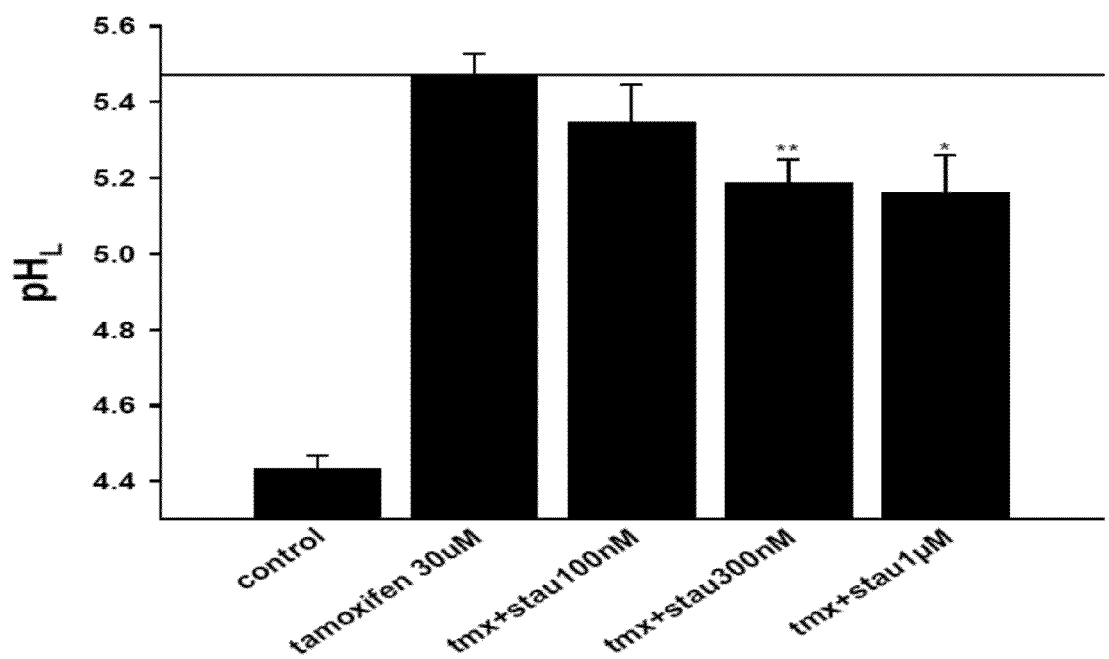
FIG. 9 is a bar graph showing that the inhibition of protein kinase C (PKC) by staurosporine also leads to a decrease in lysosomal pH in ARPE-19 cells treated with tamoxifen.

As shown in FIG. 9, inhibiting protein kinase C (PKC) by staurosporine also led to a decrease in lysosomal pH in ARPE-19 cells treated with tamoxifen, which strongly supported the concept that increased lysosomal pH is a causal step in the AMD pathology. PKC isoforms responsible for this response will be targeted with specific drugs, and treatments combined with PKC-lowering agents and agents identified above to activate cAMP, are expected to produce a more substantial decrease in pH. Thus, another category of drugs is described, to be administered, both alone and in combination with identified compounds.

β-Adrenergic Receptor and cAMP Lower Lysosomal pH: The acidification of OIL by adenosine and ATP prompted screening for additional compounds. Drugs currently used for ophthalmic treatment and those known to stimulate classic pharmacologic pathways were examined. However, compounds currently in ophthalmic use, including dorzolamide, timolol or latanaprost, did not lower $pH_L$ in ARPE-19 cells treated with 30 μM tamoxifen. Conversely, norepinephrine, epinephrine and isoproterenol did significantly decrease $pH_L$ (FIG. 4A). Potential second-messenger involvement was also probed to suggest general mechanisms of acidification. As a result, it was determined that phenylephrine had no significant effect on $pH_L$, but the reduction triggered by norepinephrine was blocked by timolol, implying involvement of the β-adrenergic receptor (FIG. 4B). Norepinephrine also reduced $pH_L$ in cells treated with chloroquine, indicating that the response was not specific to tamoxifen. Rather, it reflects a general pathway for $pH_L$ regulation (FIG. 4C)

Since the $A_{2A}$ adenosine and β-adrenergic receptors can act by stimulating $G_s$, the effect of cAMP was examined directly with cell-permeable forms of cAMP (FIG. 4D). 8-(4-chlorophenylthio) adenosine-3',5'-cyclic monophosphate (cpt-cAMP) significantly decreased $pH_L$ in cells exposed to 30 and 10 µM tamoxifen, respectively. 8-bromo-adenosine 3',5'-cyclic monophosphate (8-Br-cAMP) also seemed to acidify lysosomes treated with 10 µM tamoxifen, but the effect was not significant (p=0.054).

Thus, the ability of cpt-cAMP to lower $pH_L$, in conjunction with actions of isoproterenol and CGS21680, indicated that cAMP is a primary regulator of $pH_L$ in RPE cells. The magnitude of the acidification is predicted to restore $pH_L$ from 4.9 to 4.6 in cells treated with A2E. This corresponds to a predicted increase in activity of cathepsin D from 25% to 60% of maximum rate (Barrett et al., supra, 1977). The small increase in age-related maculopathy found in patients treated with β-blockers (van Leeuwen et al., Ophthalmol. 111:1169-1175 (2004)), might well be assigned to a lessening of β-adrenergic activity with consequent elevation of $pH_L$. Thus, the identification of cAMP as a potential messenger, combined with the findings on the Cl⁻ channels, prompted mechanistic investigations regarding the contribution of Cl⁻ channels to $pH_L$ of RPE cells.

Contribution of Cl⁻ Channels to $pH_L$ of RPE Cells

The recognition of Cl⁻ influx as a rate limiting step in lysosomal acidification led to the determination that Cl⁻ channel regulation is an effective way to control $pH_L$. The cystic fibrosis transmembrane conductance regulator ("CFTR") channel (Anderson et al., Science 251:679-682 (1991)) was selected for experimental purposes for evaluating $pH_L$ since the Cl⁻ channel is activated by cAMP, and since CFTR is present in RPE cells. Moreover, several tools are available for the manipulation of CFTR, and the relatively high incidence of cystic fibrosis ("CF") has encouraged the recent development of several drugs that can selectively activate CFTR (Caci et al., Am. J. Physiol. Lung. Cell. Mol. Physiol. 285:L180-L188 (2003); Ma et al., J. Biol. Chem. 277:37235-37241 (2002)). Substantial advances have also been made in developing gene therapy for CF (Lee et al., Biochem. J. 387:1-15 (2005); Griesenbach et al., Curr. Op. Pul. Med. 10:542-546 (2004)). Consequently, for experimental purposes, CFTR is considerably more amenable to pharmacologic and genetic manipulation than other Cl⁻ channels. While CFTR has been implicated in vesicular acidification (Barasch et al., Nature 352:70-73 (1991); Biwersi et al., Am. J. Physiol. 266:(1994)), it was understood that it does not have this role in all cell types or vesicles (Van Dyke et al., Biochem. Biophys. Res. Comm. 184:300-305 (1992); Seksek et al., J. Biol. Chem. 271:15542-15548 (1996)). However, it does acidify lysosomes in the RPE.

Effect of Pharmacologic Manipulation of CFTR on $pH_L$: It was found that the CFTR activator, genistein, acidified lysosomes in cells exposed to tamoxifen. Moreover, the CFTR inhibitor' glybenclamide, increased $pH_L$ (FIG. 5A). The reciprocal effect of the two drugs was also apparent on untreated cells, although the net effect on pH was smaller (FIG. 5B). Thus, the effects of genistein and glybenclamide are consistent with a contribution of CFTR, although the drugs are not specific, and suggest baseline levels of cAMP in RPE cells are sufficient to activate the channel. The acidification does not necessarily imply CFTR acts on lysosomal membrane, since CFTR could release ATP that acts at purinergic receptors to lower $pH_L$ through a distinct pathway (FIG. 1).

Genetic Manipulation of CFTR: Transfection with CFTR provides a mechanism to specifically increase the contribution of CFTR, and thus determine definitively whether it can acidify lysosomes in RPE cells. As a result, the lysosomes of ARPE-19 cells transfected with a full length gene for CFTR were more acidic than control cells when both were exposed to tamoxifen (FIG. 5C). Numerous controls validated this finding. First, the transfection agent lipofectamine 2000 had no effect on $pH_L$ in parallel experiments. Secondly, CFTR protein was increased >10-fold in transfected cells (FIG. 5D). Thirdly, the band size of 180 kD corresponded to the functional glycosylated band C (Rubenstein et al., J. Clin. Invest. 100:2457-2465 (1997)). Finally, a similar acidification was observed in 4 independent transfections.

Trials to identify optimal conditions found acidification most pronounced in cells transfected within 1 day after plating and measured 48 hours later, demonstrating that transfection of RPE cells with CFTR leads to an increase in CFTR protein of appropriate size and enhanced acidification in cells exposed to tamoxifen. Nonetheless, the results do not define the mechanism underlying the acidification, nor whether the primary action is on the plasma membrane or lysosomal membrane.

Figure 2:
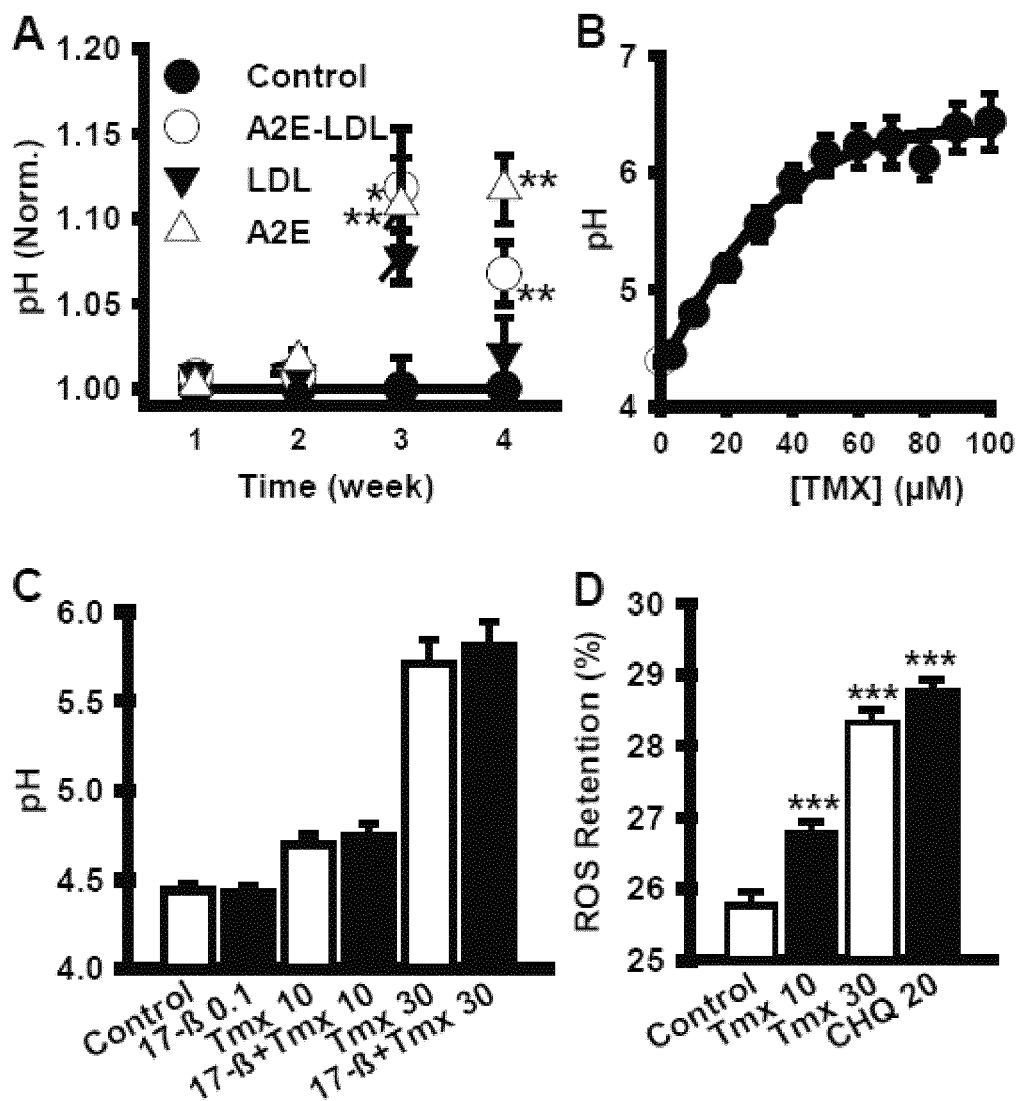
FIGS. 2A-2D are graphs showing elevation of $pH_L$ and outer segment degradation by ARPE-19 cells.
Figure 3:
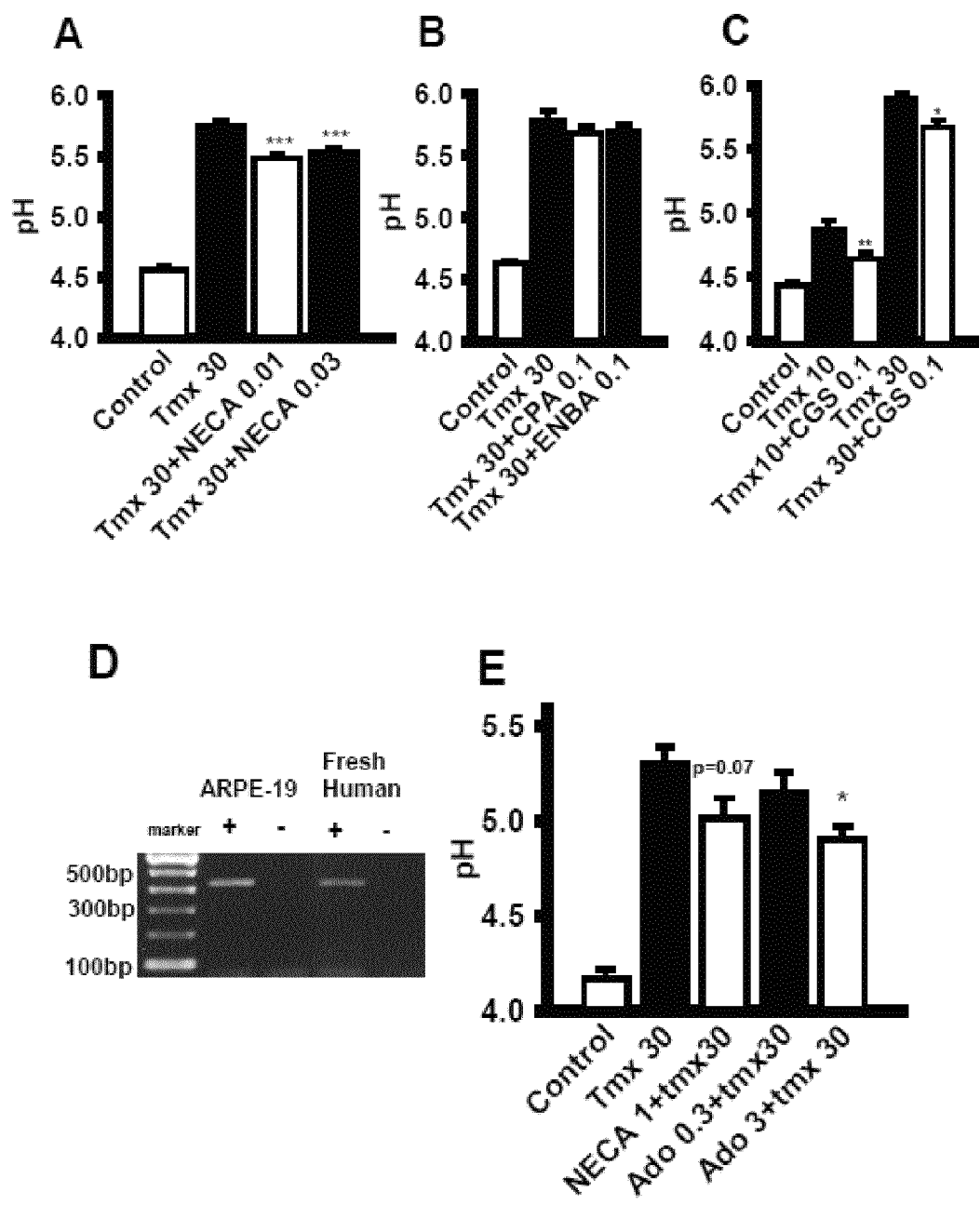
FIGS. 3A-3E are graphs showing that stimulation of adenosine receptors reduces $pH_L$.
Figure 5:
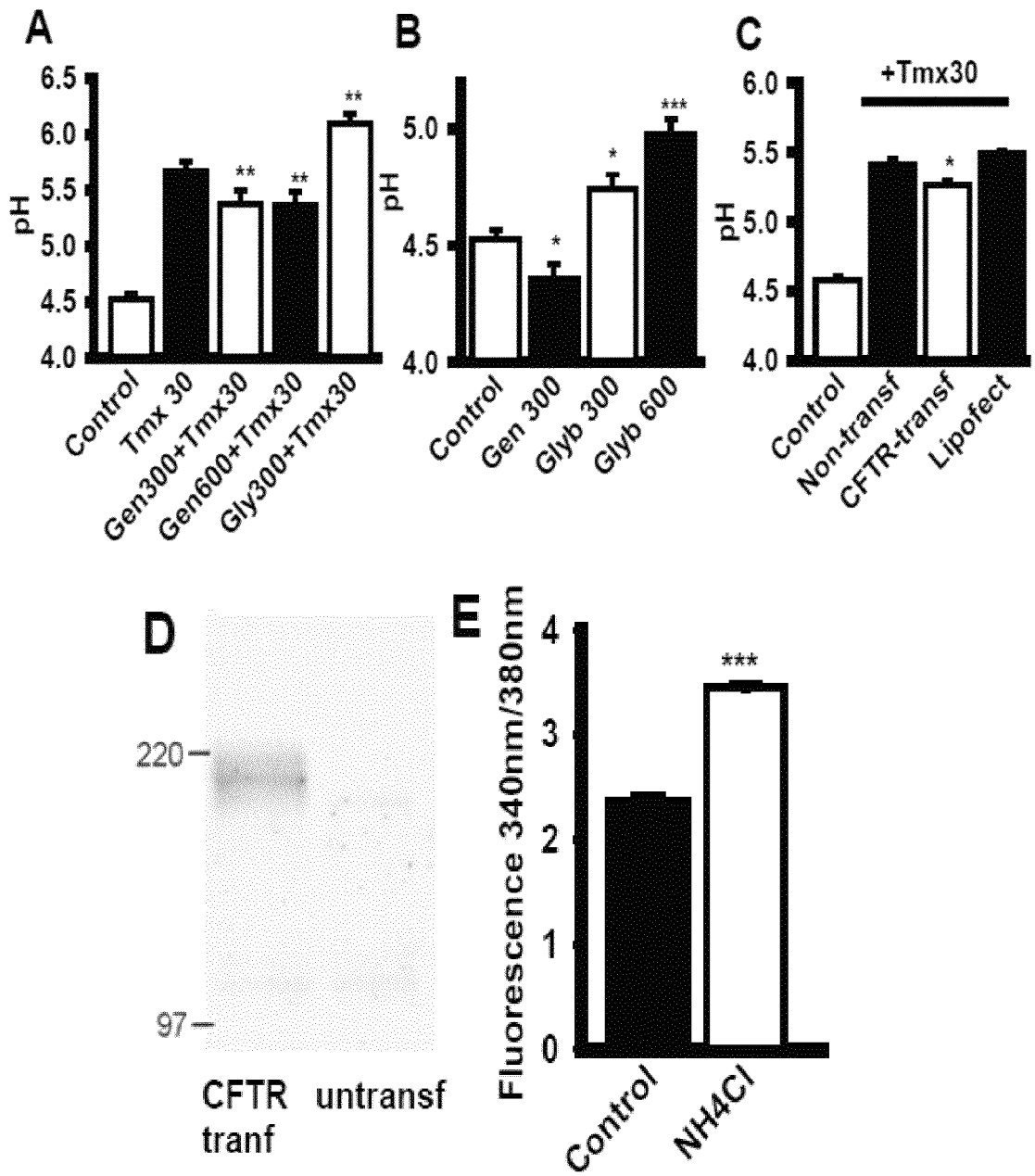
FIGS. 5A-5E show that channels contribute to $pH_L$ in ARPE-19 cells.

The data provide powerful new information to support the hypothesis in FIG. 1. Among other important points, the data embodied in the present invention demonstrate that: (i) manipulation of lysosomal Cl⁻ channel activity results in modification of the pH of the retinal pigment epithelial lysosomes ($pH_L$); (ii) Lysosensor Yellow/Blue is an effective method of quantifying $pH_L$ in RPE cells; (iii) the increase in $pH_L$ caused by A2E and tamoxifen can be quantified (FIG. 2); (iv) the reduction in outer segment degradation triggered by tamoxifen and chloroquine can be measured (FIG. 2); (v) catecholamines, inhibition of PKC, and cAMP acidify compromised lysosomes (FIGS. 3-5); and (vi) CFTR apparently contributes to this acidification (FIG. 5). These findings have broad-reaching implications for restoring lysosomal acidity and degradative function to diseased RPE cells. Therefore, it is an embodiment of the present invention to provide methods of activating channels to restore the pH of lysosomes that have been alkalinized, e.g., by A2E, in the early stages of macular degeneration, and increasing lysosomal acidity to increases activity of degradative enzymes and slow the rate of lipofuscin accumulation.

The compounds identified by the methods embodied herein, must be pharmacologically acceptable, but they may be protein or non-proteinaceous, organic or non-organic, and they may be administered exogenously or expression may be up-regulated in the patient. In the alternative, proteinaceous compounds may be produced in vitro, including by recombinant methods, and then administered to the patient.

For proteinaceous compounds, the desired expression products may be generated from transgenic constructs, comprising an isolated nucleic acid or amino acid sequence of the composition, or an active fragment thereof, that lowers $pH_L$ in RPE cells and/or restores the degradative capability of the perturbed lysosomal enzymes. The terms "nucleotide molecule," "nucleotide sequence," "nucleic acid molecule" and "polynucleotide" are used interchangeably and refer to a polymeric form of nucleotides of any length, either DNA, RNA or analogs thereof. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers (linear or circular). Amino acid sequences refer to "proteins" or "peptides" as used herein is intended to include protein fragments, or peptides. Thus, the term "protein" is used synonymously with the phrase "peptide" or "polypeptide," and includes "active fragments thereof," particularly with reference to proteins that are "proteins of interest." Protein fragments may or may not assume a secondary or tertiary structure. Protein fragments may be of any length, from 2, 3, 5 or 10 peptides in length up to 50, 100, or 200 peptides in length or more, up to the full length of the corresponding protein.

"Library," particularly as referred to previously with regard to PCR and HTS, refers to a collection of different compounds, including small organic compounds or biopolymers, including proteins and peptides. The compounds may be encoded and produced by nucleic acids as intermediates, with the collection of nucleic acids also being referred to as a library. When a nucleic acid library is used, it may be a random or partially random library, as in a combinatorial library, or it may be a library obtained from a particular cell or organism, such as a genomic library or a cDNA library. Small organic molecules can be produced by combinatorial chemistry techniques as well. Thus, in general, such libraries comprise are organic compounds, including but not limited oligomers, non-oligomers, or combinations thereof. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, catalysts, as well as combinations thereof. Oligomers include peptides (that is, oligopeptides) and proteins, oligonucleotides (the term oligonucleotide also referred to simply as "nucleotide," herein) such as DNA and RNA, oligosaccharides, polylipids, polyesters, polyamides, polyurethanes, polyureas, polyethers, poly (phosphorus derivatives), such as phosphates, phosphonates, phosphoramides, phosphonamides, phosphites, phosphinamides, etc., poly (sulfur derivatives), such as sulfones, sulfonates, sulfites, sulfonamides, sulfenamides, etc.

A "substantially pure" or "isolated nucleic acid," as used herein, refers to a nucleic acid sequence, segment, or fragment which has been separated (purified) from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term vector includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like. Suitable vectors also include, but are not limited to, plasmids containing a sense or antisense strand placed under the control of the strong constitutive promoter or under the control of an inducible promoter. Methods for the generation of such constructs are well known in the art once the sequence of the desired gene is known. Suitable vector and gene combinations will be readily apparent to those of skill in the art.

A nucleic acid encoding the therapeutic compound, or an active fragment thereof, can be duplicated using a host-vector system and traditional cloning techniques with appropriate replication vectors. A "coding sequence" or a sequence which "encodes" the selected polypeptide (its "expression product"), is a nucleotide molecule which is transcribed (in the case of DNA) and translated (in the case of mRNA) into a polypeptide, for example, in vivo when placed under the control of appropriate regulatory sequences (or "control elements"). An "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide. A recombinant polynucleotide may also serve a non-coding function (e.g., promoter, origin of replication, ribosome-binding site).

A "host-vector system" refers to host cells, which have been transfected with appropriate vectors using recombinant DNA techniques. The vectors and methods disclosed herein are suitable for use in host cells over a wide range of eukaryotic organisms. This invention also encompasses cells transformed with the replication and expression vectors, using methods known in the art. Indeed, a gene encoding the modulating nucleic acid, such as the nucleic acid sequence encoding a peptide, or an active fragment thereof, that lowers $pH_L$ in RPE cells and/or restores the degradative capability of the perturbed lysosomal enzymes, can be duplicated in many replication vectors, and isolated using methods described, e.g., in Maniatis et al., *Molecular Cloning: A Laboratory Manual*, Cold Spring Harbor Laboratory, New York (1982) and Sambrook et al., *Molecular Cloning: A Laboratory Manual*, Cold Spring Harbor Laboratory, New York (1989), and the various references cited therein.

The selected gene, made and isolated using the above methods, can be directly inserted into an expression vector, such as pcDNA3 (Invitrogen) and inserted into a suitable animal or mammalian cell. In the practice of one embodiment of this invention, the gene or gene fragment, such as the purified nucleic acid molecule encoding the peptide, or an active fragment thereof, that lowers $pH_L$ in RPE cells and/or restores the degradative capability of the perturbed lysosomal enzymes, is introduced into the cell and expressed. A variety of different gene transfer approaches are available to deliver the gene or gene fragment encoding the modulating nucleic acid into a target cell, cells or tissues.

As used herein, "recombinant" is intended to mean that a particular DNA sequence is the product of various combination of cloning, restriction, and ligation steps resulting in a construct having a synthetic sequence that is indistinguishable from homologous sequences found in natural systems. Recombinant sequences can be assembled from cloned fragments and short oligonucleotides linkers, or from a series of oligonucleotides. As noted above, one means to introduce the nucleic acid into the cell of interest is by the use of a recombinant expression vector. "Recombinant expression vector" is intended to include vectors, capable of expressing DNA sequences contained therein, where such sequences are operatively linked to other sequences capable of effecting their expression. It is implied, although not always explicitly stated, that these expression vectors must be replicable in the host organisms, either as episomes or as an integral part of the chromosomal DNA. Suitable expression vectors include viral vectors, e.g., adenoviruses, adeno-associated viruses, retroviruses, cosmids and others, typically in an attenuated or non-replicative form. Adenoviral vectors are a particularly effective means for introducing genes into tissues in vivo because of their high level of expression and efficient transformation of cells, both in vitro and in vivo.

Accordingly, when reference is made herein to "administering" the compound that lowers $pH_L$ in RPE cells and/or restores the degradative capability of the perturbed lysosomal enzymes, or a functionally equivalent peptide fragment thereof, to a patient, it is intended that such methods include not only delivery of an exogenous composition to the patient, but also methods for reducing lysosomal pH (i.e., increasing acidity) within the RPE cells of the patient, or reducing levels of lipofuscin or slowing the rate of lipofuscin accumulation. As noted, the compound may be protein in nature or non-protein. However, when the compound is an expressed protein, expression levels of the gene or nucleotide sequence inside a target cell are capable of providing gene expression for a duration and in an amount such that the nucleotide product therein is capable of providing a therapeutically effective amount of gene product or in such an amount as to provide a functional biological effect on the target cell. By "gene delivery" is meant transportation of a composition or formulation into contact with a target cell so that the composition or formulation is capable of being taken up by means of a cytotic process into the interior or cytoplasmic side of the outermost cell membrane of the target cell, where it will subsequently be transported into the nucleus of the cell in such functional condition that it is capable of achieving gene expression.

By "gene expression" is meant the process, after delivery into a target cell, by which a nucleotide sequence undergoes successful transcription and translation such that detectable levels of the delivered nucleotide sequence are expressed in an amount and over a time period that a functional biological effect is achieved. "Gene therapy" encompasses the terms gene delivery and gene expression. Moreover, treatment by any gene therapy approach may be combined with other, more traditional therapies.

The compounds used for therapeutic purposes are referred to a "substantially pure," meaning a compound, e.g., a protein or polypeptide which has been separated from components which naturally accompany it. Typically, a compound is substantially pure when at least 10%, or at least 20%, or at least 50%, or at least 60%, or at least 75%, or at least 90%, or at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

By "patient" or "subject" is meant any vertebrate or animal, preferably a mammal, most preferably a human, that is affected by or susceptible to retinal diseases or disorders resulting in macular degeneration and loss of vision. Thus, included within the present invention are animal, bird, reptile or veterinary patients or subjects, the intended meaning of which is self-evident. The methods of the present invention are useful in such a patient for the treatment or prevention of the following, without limitation: macular degeneration, age related macular degeneration, lysosomal alkylinization of the RPE cells of the eye, damaging accumulation of lipofuscin, and other diseases of the retina of the eye.

In another embodiment, the invention may further include the step of administering a test compound to the cell prior to the detecting step, wherein the absence of binding of the detectable group to the internal structure indicates that the test compound inhibits the binding of the members of the specific binding pair. Any test compound can be used, including peptides, oligonucleotides, expressed proteins, small organic molecules, known drugs and derivatives thereof, natural or non-natural compounds, non-organic compounds, etc. Administration of the test compound may be by any suitable means, including direct administration, such as by electroporation or lipofection if the compound is not otherwise membrane permeable, or (where the test compound is a protein), by introducing a heterologous nucleic acid that encodes and expresses the test compound into the cell. Such methods are useful for screening libraries of compounds for new compounds that disrupt the binding of a known binding pair.

In yet another embodiment, the present invention provides an assay for determining agents, which manipulate lysosomal Cl$^-$ channel activity to modify pH of the retinal pigment epithelial lysosomes ($pH_L$), or that bind to, neutralize or acidify lysosomes of the RPE, or other factors in a sequence of events leading to the onset of lysosomal alkylinization of the RPE cells of the eye, damaging accumulations of lipofuscin, and eventually macular degeneration, thereby reducing, modulating or preventing such pathologies. Such an assay comprises administering an agent under test to the cells or model animals, such as those described herein, at low cell density, and monitoring the onset of lysosomal alkylinization of the RPE cells of the eye or whether the agent effects a reversal of the problem. For example, Lysosensor Yellow/Blue is an effective method of quantifying $pH_L$ in RPE cells. A further assay according to the invention comprises administering the agent under test to determine and quantify the increase in $pH_L$ caused by A2E (see, FIG. 2), or to determine and measure the reduction in outer segment degradation triggered by the agent, as demonstrated using tamoxifen and chloroquine (see, FIG. 2), as well as purines, catecholamines and cAMP (see, FIGS. 3-5). Agents may, thus, be selected which effectively reduce, inhibit, neutralize or prevent lysosomal alkylinization of the RPE cells, retinal dysfunction, or the like. The agents thus selected, and the assays used to identify them, are also intended to be a part of the present invention.

In still another embodiment, sensitivity of $pH_L$ levels in vivo are used as a biomarker for measuring macular disease severity or treatment effectiveness.

In accordance with the present invention, the compound (including organic or non-organic compositions, a peptide, receptor, or an active fragment thereof), that lowers $pH_L$ in RPE cells and/or restores the degradative capability of the perturbed lysosomal enzymes, or fragment thereof, or that binds to, neutralize or inhibit lysosomal alkylinization of the RPE cells, when used in therapy, for example, in the treatment of an aging patient or one with early onset symptoms of macular degeneration, lysosomal alkylinization of the RPE cells, damaging accumulations of lipofuscin, retinal dysfunction, or the like, can be administered to such a patient either alone or as part of a pharmaceutically acceptable composition. Optionally with a preservative, diluent, and the like are also added. The compound may further be administered in the form of a composition in combination with a pharmaceutically acceptable carrier or excipient, and which may further comprise pharmaceutically acceptable salts. Examples of such carriers include both liquid and solid carriers, such as water or saline, various buffer solutions, cyclodextrins and other protective carriers or complexes, glycerol and prodrug formulations. Combinations may also include other pharmaceutical agents.

The term "pharmaceutically acceptable" refers to physiologically and pharmaceutically acceptable compounds of the invention: i.e., those that retain the desired biological activity and do not impart undesired toxicological effects on the patient or the patient's eye or RPE cells.

Various methods of "administration" of the therapeutic or preventative agent (compound or composition) can be used, following known formulations and procedures. Although targeted administration is described herein and is generally preferred, it can be administered intravenously, intramuscularly, subcutaneously, topically, intraorbitally, optionally in a dispersible or controlled release excipient. One or several doses may be administered as appropriate to achieve systemic or parental administration under suitable circumstances. Compounds or compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, saline, buffered saline, dextrose, ethanol, glycerol, polyols, and the like, and suitable mixtures thereof. Proper fluidity can be maintained, for example, by the use of a coating, such as lecithin, by the maintenance of the required particle size in the case of dispersions and by the use of surfactants. These compositions may also contain adjuvants, such as preserving, wetting, emulsifying, and dispensing agents. Sterility can be ensured by the addition of various antibacterial and antifungal agents. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Persons of ordinary skill can easily determine optimum dosages, dosing methodologies and repetition rates. Repetition rates for dosing can be readily estimated based upon measured residence times and concentrations of the drug in bodily fluids or tissues. Amounts and regimens for the administration of compounds used to lower $pH_L$ in RPE cells and/or restores the degradative capability of the perturbed lysosomal enzymes can be determined readily by those with ordinary skill in the clinical art of treating retinal disease, including macular degeneration. Generally, the dosage of such compounds or treatment using such compounds will vary depending upon considerations, such as: age; health; conditions being treated; kind of concurrent treatment, if any, frequency of treatment and the nature of the effect desired; extent of tissue damage; gender; duration of the symptoms; and, counter-indications, if any, and other variables to be adjusted by the individual physician. Dosage can be administered in one or more applications to obtain the desired results (see, e.g., dosages proposed for human therapy in known references).

When the therapeutic compound is a peptide, or an active fragment thereof, that lowers $pH_L$ in RPE cells and/or restores the degradative capability of the perturbed lysosomal enzymes, instead of direct administration to the target cells, such peptides can also be produced in the target cells by expression from an encoding gene introduced into the cells, e.g., in a viral vector. The vector could be targeted to the specific cells to be treated, or it could contain regulatory elements, such as receptors, which are switched on more or less selectively by the target cells. Increased expression is referred to as "up-regulation" as discussed herein.

By "therapeutically effective" as used herein, is meant that amount of composition that is of sufficient quality and quantity to neutralize, ameliorate, modulate, or reduce the cause of or effect of lysosomal alkylinization of the RPE cells, retinal dysfunction, macular degeneration or the like. Because $Ca^{2+}$ elevations underlie ion transport changes, and the regulation of lysosomal acidification, it is assumed when the term "therapeutically effective," with regard to administration of the compound to lower $pH_L$ in RPE cells and/or restore the degradative capability of the perturbed lysosomal enzymes, or the functionally equivalent peptide fragment thereof, that $Ca2^+$ or other necessary divalent ion is present at the levels necessary to activate the therapeutic molecule.

By "ameliorate," "modulate," or "decrease" is meant a lessening or lowering or prophylactic prevention of the detrimental effect of the disorder in the patient receiving the therapy, thereby resulting in "protecting" the patient. A "sufficient amount" or "effective amount" or "therapeutically effective amount" of an administered composition is that volume or concentration which causes or produces a measurable change from the pre-administration state in the cell or patient, this is also referred to herein as "restoring" or "restoration of" the lysosomal acidity.

While the subject of the invention is preferably a human patient, it is envisioned that any animal with lysosomal alkylinization of the RPE cells, damaging accumulations of lipofuscin, retinal dysfunction, macular degeneration or the like, can be treated by a method of the present invention. As used herein, the terms "treating" and "treatment" are intended to include the terms "preventing" and "prevention." One embodiment of the present invention includes the administration of a compound (including an organic or inorganic composition, peptide, or an active fragment thereof, receptor, etc) that lowers $pH_L$ in RPE cells and/or restores the degradative capability of the perturbed lysosomal enzymes, in an amount sufficient to treat or prevent lysosomal alkylinization of the RPE cells, lipofuscin accumulation, retinal dysfunction, macular degeneration, or the like.

The terms "inhibition" or "blocking" refer to a statistically significant decrease in lysosomal alkylinization of the RPE cells or lipofuscin accumulation, associated with retinal dysfunction, macular degeneration, or the like, as compared with a selected standard of activity or for cells or tissues grown without the addition of the selected compound (including a peptide, or an active fragment thereof) that lowers $pH_L$ in RPE cells and/or restores the degradative capability of the perturbed lysosomal enzymes. "Preventing" refers to effectively 100% levels of prophylactic inhibition. Preferably, the increased levels of the compound (meaning a higher concentration than was present before additional quantities of the compound was administered or before its expression was up-regulated in the patient) decreases lysosomal alkylinization and/or enhances acidity of the RPE cells or lipofuscin accumulation, associated with retinal dysfunction, macular degeneration, or the like, or risk thereof, by at least 5%, or by at least 10%, or by at least 20%, or by at least 50%, or even by 80% or greater, and also preferably, in a dose-dependent manner.

The invention is further defined by reference to the following specific, but nonlimiting, examples that reverse or alter lysosomal alkylinization of the RPE cells or change lipofuscin accumulation, associated with retinal dysfunction, macular degeneration, or the like. Reference is made to standard textbooks of molecular biology that contain definitions and methods and means for carrying out basic techniques, encompassed by the present invention. It will be apparent to one skilled in the art that many modifications, both to materials and methods, may be practiced without departing from the purpose or narrowing the scope of this invention.

EXAMPLES

Materials and Methods: The following Materials and Methods apply to all of the following Examples of the present invention.

ARPE-19 Cells: ARPE-19 cells (ATCC) were grown to confluence in 25 cm$^2$ Primary Culture flasks (Becton Dickinson) in a 1:1 mixture of Dulbecco's modified Eagle medium (DMEM) and Ham's F12 medium with 3 mM L-glutamine, 100 µg/ml streptomycin and 2.5 mg/ml Fungizone and/or 50 µg/ml gentamicin and 10% fetal bovine serum (all Invitrogen Corp). Cells were incubated at 37° C. in 5% $CO_2$, and subcultured weekly with 0.05% trypsin and 0.02% EDTA. In many experiments, cells were grown for 2 weeks, with the above growth medium replaced with one containing only 1% serum for the second week to encourage differentiation.

Isolation of Bovine and Mouse RPE Cells: The bovine RPE-choroid and sclera were removed, incubated in 2.5% trypsin at 37° C. in 5% $CO_2$ for 30 min, after which RPE sheets are dissected, washed and plated in 96-well plates with 10% serum medium. Mouse eyes were incubated in DMEM for 3 hrs at room temperature (RT), then in 0.1% trypsin and 0.4 mg/ml collagenase IV with 1 mM EDTA for 45 min at RT. RPE sheets were dissected out, washed, and incubated with 0.25% trypsin/0.02% EDTA in order to obtain a suspension of single cells, then grown as above.

HTS Measurement of $pH_L$: ARPE-19 cells were grown in 96-well plates, rinsed 3× with isotonic solution (IS; prepared from NaCl 105 mM, KCl 5 mM, HEPES Acid 6 mM, Na HEPES 4 mM, $NaHCO_3$ 5 mM, mannitol 60 mM, glucose 5 mM, $MgCl_2$ 0.5 mM, $CaCl_2$ 1.3 mM) and incubated with 5 µM LysoSensor Yellow/Blue (Invitrogen Corp.) diluted with IS. Extensive trials determined that the optimal response is obtained with 5 minute dye loading and 15 minute postincubation. Fluorescence was measured with a Fluoroskan 96-well Plate Reader (Thermo Electron Corp.). $pH_L$ was determined from the ratio of light excited at 340 nm vs 380 nm (>520 nM em). $pH_L$ was calibrated by exposing cells to 10 µM $H^+/Na^+$ ionophore monensin and 20 µM $H^+/K^+$ ionophore nigericin in 20 MES, 110 KCl and 20 NaCl at pH 3.0-7.0 for 15 min. All reagents were from Sigma Chemical Corp. unless otherwise indicated.

Measurement of $pH_L$ from Isolated Mouse Cells: Based on protocols that are used extensively to measure $Ca2^+$ from retinal ganglion cells (Zhang et al. *Invest. Ophthalmol. Vis. Sci.* 46:2183-2191 (2005)), cells were fixed on coverslips and mounted on Nikon Eclipse inverted microscope, visualized with a x40 oil-immersion fluorescence objective, and perfused with control solution. The field was alternatively excited at 340 nm and 380 nm, and fluorescence >515 emitted from the region of interest surrounding individual cells is measured with a CCD camera and Imagemaster software (Photon Technologies International, Inc). After baseline levels were recorded for 3-5 minutes in the absence of dye, solution was replaced with 5 µM Lysosensor Yellow/Blue dye for 5 minutes before washing for an additional 15 minutes. The ratios in the control solutions were recorded, and then acidifying drugs were added. Ratios were converted to pH with monensin/nigericin as above.

Outer Segment Degradation: Bovine retinas were homogenized in 20% sucrose with 130 mM NaCl, 20 mM Tris-HCl, 10 mM glucose, 5 mM taurine and 2 mM MgC12 (pH 7.20). The homogenate was placed in ultracentrifuge tubes with 20%, 27%, 33%, 41%, 50% and 60% sucrose, respectively, and centrifuged for 70 minutes at 28,000 rpm on a SW28 rotor (4° C.). The supernatant was filtered, diluted in 0.02M Tris-HCl buffer (pH 7.2) and centrifuged at 13,000×g for 10 minutes (4° C.). The pellet was resuspended in 10 PBS, 0.1 mM NaCl and 2.5% sucrose. Outer segments were loaded with 5 µM calcein-AM in PBS for 10 minutes, and spun 2× at 14,000 rpm to wash. Outer segments were then diluted 1:100 in growth medium and added to ARPE-19 cells in 96-well plates. After 2 hours, cells were washed vigorously 3×, and incubated with growth medium for 3 hours, after which 30 µM tamoxifen was added with acidifying drugs. After 24 hours, wells were washed 3×, and the fluorescence was read with a plate scanner at 485 nm to quantify the signal.

QPCR: Quantitative polymerase chain reaction (PCR) techniques used previously (see Zhang et al., *Mol Vis*, under revision) are applied to $Cl^-$ channels identified by EST libraries and PCR studies of human RPE cells (Wills et al., *Invest. Ophthalmol. Vis. Sci.* 41:4247-4255 (2000); Weng et al., *Am. J. Physiol. Cell. Physiol.* 283:C839-C849 (2002); Wistow et al., *Mol. Vis.* 8:205-220 (2002); Ida et al. *Mol. Vis.* 10:439-444 (2004)). As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and of an inducing agent, such as DNA polymerase, and at a suitable temperature and pH. The primer is preferably single stranded for maximum efficiency in amplification, but the exact length of the primer will depend on many factors. The amplified segments of the target sequence become the predominant sequences (in terms of concentration) in the mixture, they are said to be "PCR amplified."

Transfections: The plasmid DNA containing the appropriate CFTR construct was diluted 1:50 in serum-free Opti-MEM®I Medium, with Lipofectamine 2000™ diluted 1:25 in Opti-MEM®I Medium. After mixing, reagents were combined and incubated for 20 minutes at RT. This mixture was diluted in growth medium and added to ARPE-19 cells grown to 90% confluence in 96-well plates. Plasmids were incubated with cells at 37° C. for 4-6 hrs, after which, the transfection mix was replaced with growth medium. Cells were then grown for a further 48 hrs before measurements.

Isolation of Lysosomes: ARPE-19 cells were detached with 0.25% trypsin, centrifuged at 1000 rpm for 5 minutes, and resuspended in 0.25M sucrose with 5 mM ATP in 10 mM Tris buffer (pH 7.4 with HCl). After homogenization, samples were spun at 1000×g (10 min). The supernatant was centrifuged (20,000×g, 10 min) and the pellet was resuspended in a 0.25 M sucrose buffer with 8 mM $CaCl_2$ in Tris-HCl buffer (pH 7.4) to lyse mitochondria (15 min, 35° C.). After a subsequent centrifugation (5000×g, 15 min), the supernatant was placed on top of a discontinuous sucrose gradient (45%, 34.5% and 14.3%, Tris-HCl buffer). The lysosomal fraction was collected in the 34.5%-14.3% interface after an ultracentrifugation at 77,000×g for 2 hours in a SW71 rotor. After isolation, lysosomes were diluted 1:10 in a 150 mM KCl solution in Tris-HCl (pH 7.4) and pelleted at 25,000×g. The pellet was then resuspended in 5 µM Lysosensor dye. Cells were washed 2× by centrifugation (25,000×g, 15 min), resuspended in test or control solutions including 5 mM MgATP, plated into a 96 well plate (50 µl/well) and the pH was measured as above.

Western Blots: The term "Western blot," refers to the immunological analysis of protein(s), polypeptides or peptides that have been immobilized onto a membrane support. ARPE-19 were washed 2× and lysed in RIPA (radioimmunoprecipitation assay solution; basically PBS, 1% NP-40, 0.5% sodium doxycholate, 0.1% SDS). Samples were sonicated and cleared by centrifugation (10,000 g; 30 min, 4° C.). Concentrations were determined with BCA ((bicinchoninic acid) protein assay; e.g., Endosafe™-PTS BCA™, Charles River Laboratories. 60 µg of protein was separated by acrylamide gel electrophoresis on a SDS-PAGE gel, and transferred from the gel to a solid support, such as nitrocellulose or a nylon membrane, e.g., a PVDF (polyvinylidene fluoride) membrane (e.g., Millipore). Nonspecific binding was blocked with 5% nonfat dried milk for 1 hr (25° C.). The immobilized proteins were then exposed to an antibody having reactivity towards an antigen of interest, i.e., blots were incubated with monoclonal anti-CFTR (M3A7; Upstate, 0.5 µg/ml) overnight (4° C.). The binding of the antibody (i.e., the primary antibody) is detected by use of a secondary antibody which specifically binds the primary antibody, typically this is conjugated to an enzyme which permits visualization by the production of a colored reaction product or catalyzes a luminescent enzymatic reaction. In this case, the antibody reaction was followed by anti-mouse IgG conjugated with horseradish peroxidase (1:5000; 25° C. for 1 hr), developed by chemiluminescence detection, imaged and quantified.

Example 1

Identification of Receptors that Lower pH in Bovine and Human RPE Cells

Data has shown that the $A_{2A}$ adenosine and P2Y11 receptors linked to $G_s$ lower $pH_L$. To test whether pharmacologic manipulation could restore a perturbed lysosomal pH and enhance degradative ability in RPE cells, requires (i) definitively identifying receptors involved in lysosomal acidification, (ii) determining whether compounds found to decrease $pH_L$ in cells treated with tamoxifen are effective against A2E, and (iii) assess whether the identified compounds can restore rates of outer segment degradation. The characterization of the receptors is performed on cells treated with tamoxifen since it requires only 15 minutes to modify $pH_L$.

In general, each condition below used 3-12 independent wells per plate, in 3-6 separate plates. As levels from individual plates varied, data was normalized to the mean $pH_L$ for control wells from each plate. Fluorescent ratios were converted to pH following calibration performed on each plate as described. Incubation with Lysosensor Yellow/Blue was kept constant and all measurements were performed 15 min after removal of dye from the bath to ensure continuity. Significance was determined with a one-way ANOVA and Tukey post test. Drugs were always tested on control cells to ensure modification of healthy RPE cells was minimal, and cells were not exposed to dye to make sure effects were specific.

All background was subtracted from the fluorescence excited at 340 and 380 nm independently before calculation of the ratio.

$A_{2A}$ Adenosine Receptor: The agonist CGS21680 is selective for the $A_{2A}$ receptor at the low levels used in the preliminary data. $EC_{50}$ is 290 nM for the $A_1$ receptor; 27 nM for the $A_{2A}$ receptor; >1000 nM for the $A_{2B}$ receptor; and 67 nM for the $A_3$ receptor. Receptor specificity was confirmed with the $A_{2A}$ antagonist, ZM241385, with an $IC_{50}$ of 536 nM for the $A_1$ receptor; 1.4 nM for the $A_{2A}$ receptor; 31 nM for the $A_{2B}$ receptor; and 269 nM for the $A_3$ receptors. ZM241385 was applied to ARPE-19 cells at 3, 10 and 30 nM, 3 min before application of tamoxifen in the presence and absence of 30 nM NECA (FIG. 3A). When the response to NECA was not fully blocked by 10 nM ZM241385, the $A_{2B}$ receptor antagonist MRS1754 was tested as above. While there is currently no specific agonist for the $A_{2B}$ receptor, MRS1754 acted with an $IC_{50}$ of 400 nM at the $A_1$ receptor; 500 nM at the $A_{2A}$ receptor; 2 nM at the $A_{2B}$ receptor; and 570 nM at the $A_3$ receptor. The most effective antagonists were confirmed on bovine RPE cells.

Figure 6:
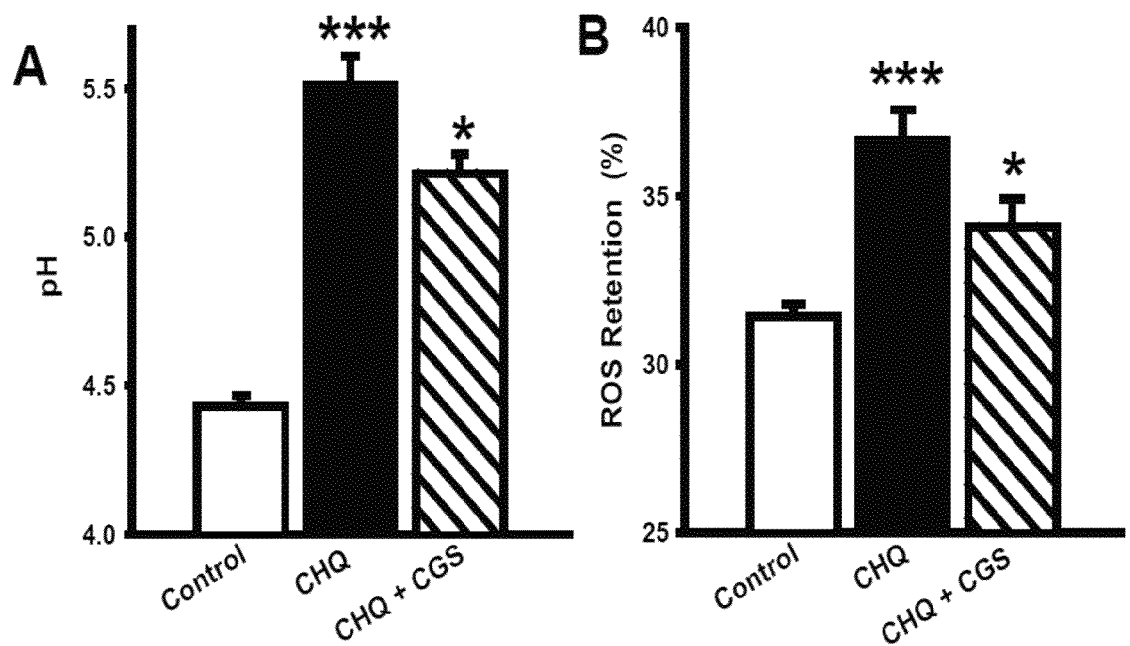
FIGS. 6A and 6B are graphs showing that lysosomal function was restored by an adenosine receptor agonist.

$A_{2A}$ adenosine receptor agonist CGS21680 (CGS, 100 nM) decreased the lysosomal alkalinization induced by chloroquine (CHQ, 20 µM) in ARPE-19 cells B). See, FIGS. 6A and 6B. The effect of restoring lysosomal pH on the activity of lysosomal enzymes was quantified from the clearance of fluorescently labeled rod outer segments, as described above. While 20 µM CHQ slowed clearance of outer segments over 24 hrs, 100 nM CGS restored the degradative capacity of the ARPE cells (FIG. 5A). This result was consistent with its acidifying effect on lysosomal pH, and confirmed that restoring lysosomal pH does, in fact, restore the degradative ability of compromised lysosomes. It further demonstrated that CGS can acidify lysosomes damaged by different insults, and emphasized the potential of CGS as a useful compound for restoring enzymatic function.

P2Y11 Receptor: The initial investigation screened agonists that act at multiple P2 receptors for their effect on $pH_L$ using the high through-put assay. BzATP, ATP, ATPγS, ADPγS and 2 MeSATP and AR-C67085 were added at 10, 30, 100 and 300 µM, respectively, and relative actions were compared with published information for the human P2Y11 receptor (von Kugelgen et al, supra, 2000; Communi et al., supra, 1997; Communi et al., Br. J. Pharmacol. 128:1199-206 (1999)). ATP was added in the presence of ecto-ATPase/eNPP inhibitors βγmATP and ARL67156 (100 µM) since they prevent degradation of ATP in these cells. Receptor involvement was confirmed with antagonists suramin, reactive blue 2 and pyridoxal-phosphate-6-azophenyl-2',4'-disulphonic acid (PPADS; all at 0.1, 1, 10 and 100 µM). Since the finding that ATP had the ability to elevate cAMP in the RPE was novel, the effect of ATP on cAMP was measured directly using the cAMP-Screen Direct Chemiluminescent Immunoassay System kit from Applied Biosystems using an HTS luminometer to measure ATP levels. The role of cAMP was confirmed by inhibiting $pK_A$ with 100 µM Rp-8-Br-cAMPS. As above, the most effective agonists and antagonists were tested on bovine RPE cells.

Example 2

Pharmacological Restoration of Lysosomal pH Increased by A2E

To demonstrate that agonists that were effective with tamoxifen also lower $pH_L$ in cells treated with A2E, basic protocols used to generate preliminary data were expanded to show the effect of acidifying drugs on ARPE-19 cells exposed to A2E. Cells were challenged with 14 nM A2E (LDL-free) for 4 weeks based on the results of FIG. 2A. Two treatment strategies were employed. First, putative acidifying compounds were applied to cells once after 4 weeks of loading with A2E, and measurements were made 15 min. later, as was done for tamoxifen. This mimics treatment of a patient with a pre-existing A2E accumulation. While A2E is likely to be retained in lysosomes once accumulated (Sparrow et al., supra, 2005; Mata et al., supra, 2000), the ability to degrade additional outer segment material may depend more closely on enzyme activity, and thus, on lysosomal pH. Secondly, acidifying compounds were given with A2E for 4 weeks and the baseline $pH_L$ was compared with cells receiving A2E alone. This indicated whether the agonists were preventative.

Autofluorescence: Preliminary trials indicated that A2E contributed less than 0.4% to the fluorescent signal in dye-loaded cells. This was important, because it suggested that small increases in $pH_L$ could be occurring even before an increase in fluorescence can be detected. It is possible that the enhanced emission at 380 nm vs. 340 nm might interfere with ratiometric assessment of the Lysosensor dye in some trials. This contribution was assessed separately in each experiment by exposing cells without dye to 340 or 380 nm light, as performed in preliminary data. If the fluorescence attributed to A2E became greater than 1% of the total signal, the appropriate subtraction was performed before determining the true ratio.

Pharmacology: Norepinephrine, isoproteranol, NECA, CGS21680, cpt-cAMP, 8-Br-cAMP, appropriate P2 agonists and dopamine were tested on cells treated with A2E. Receptor identification was confirmed using appropriate antagonists. While the initial concentrations were the same as those found to be effective above, levels were adjusted if A2E-treated cells proved to be more or less resistant to restoration of lysosomal acidity.

Anticipated results and interpretation: Stimulation of β-adrenergic and $A_{2A}$ adenosine receptors was expected to lower $pH_L$ elevated by treatment with A2E. The degree of restoration was found to depend on the magnitude of the alkalinization, but the quantification in the data suggested that treatments would restore acidity by >50%. This was predicted to double activity of cathepsin D (Barrett, supra, 1977). Drugs were expected to have a minimal effect on $pH_L$ in untreated cells, consistent with preliminary data.

The purification and stability of A2E makes its use challenging (Parish et al., supra, 1998), but the A2E used in these experiments (Neuron Systems Co.) was highly purified and regularly assessed for spontaneous isomerization. In addition, each batch was stored in the dark at −80° C. and purity is assessed regularly. Exposure of cells and A2E to light was minimized since photooxidation of A2E decreases fluorescence and increases toxicity (Sparrow et al., *Invest. Ophthalmol. Vis. Sci.* 43:1222-1227 (2002). While the photooxidation of A2E clearly enhanced its ability to injure the RPE cells (Sparrow et al., supra, 2005; Schutt et al., *Ophthalmologe.* 97:682-687 (2000)), the effects of photo-oxidized A2E on $pH_L$ were outside the scope of the current invention. Thus, the effects of A2E on $pH_L$ were first studied in the absence of added light to properly assess the effects of A2E alone, without added variables.

Example 3

Effect of Lysosomal Acidification on Clearance of Photoreceptor Outer Segments

To show that lowering $pH_L$ increased the clearance of outer segments, an approach was designed based upon the findings shown in FIG. 2, wherein tamoxifen and chloroquine slowed the clearance of outer segments. This also showed whether drugs capable of lowering lysosomal pH, also enhance clearance of outer segments. In addition, this experiment provided a second methodology to assess the effectiveness of the compounds identified above.

The primary lysosomal enzymes in RPE cells function optimally in acidic environments, and compounds that alkalinize lysosomes can slow the degradation of outer segments and enhance accumulation of undigested material. Because this accumulation appeared to be a key step in the development and accumulation of lipofuscin, the ability of acidifying drugs to also restore rates of outer segment clearance was central to the potential of a drug. This is particularly important because $Cl^-$ concentration can have additional effects on enzyme activity, complicating the relationship between $pH_L$ and degradation.

Isolated bovine outer segments loaded with calcein were supplied to ARPE-19 cells in 96-well plates for 2 hrs, washed 3× and maintained in control medium for an additional 3 hr (see Methods). Acidifying drugs were then added at the most effective concentrations as identified above. Drugs were given to cells both with, and without, tamoxifen to determine whether baseline levels of degradation were also altered. Because lipofuscin is distributed heterogeneously across foveal RPE cells in macular degeneration (Holz et al., *Invest. Ophthalmol. Vis. Sci.* 42:1051-1056 (2001)), drugs with a minimal impact on healthy cells were preferable. As some compounds may have an independent effect on the rates of phagocytosis (Hall et al., *Invest. Ophthalmol. Vis. Sci.* 34:2392-2401 (1993)), the effect of the signal in the absence of tamoxifen was subtracted from the effect with tamoxifen to isolate specific actions. Promising compounds were examined for their effects on cells treated with A2E, although the restoration of $pH_L$ is unlikely to remove A2E itself. However, other components of the outer segments are amendable to digestion by lysosomal enzymes at the appropriate $pH_L$, and acidification could minimize the secondary effect of this accumulation.

Phagocytosis of photoreceptor outer segments by the RPE involves binding, ingestion and degradation. Binding is distinguished by labeling outer segments with FITC, and quenching any fluorescence remaining on the membrane with trypan blue. While the increased brightness, pH independence, and the minimal background fluorescence with calcein-AM, make the outer segments labeled with calcein preferable in studies of lysosomes, it was determined that calcein is relatively resistant to quenching. However, the effect of binding was minimized by the 3 hour window between exposure to outer segments and the application of drugs, and the measurements taken 24 hrs later. As A2E does not affect binding itself, these precautions enabled the use of calcein with its multiple advantages.

Experiment 4

Direct Manipulation of $pH_L$ in Isolated Lysosomes

While measurements from within intact cells can identify plasma membrane receptors capable of regulating $pH_L$, the topology makes it difficult to deduce the mechanisms that were responsible. Lysosomal isolation enabled the direct access to the pertinent membrane and its $Cl^-$ channels, allowing perturbations of the processes contained exclusively on the lysosome. Therefore, the purpose of this experiment was to determine whether the pH of isolated lysosomes is dependant on Cr influx.

Cl$^-$/H$^+$ Coupling: Lysosomes were isolated as they were for the experiments resulting in the data presented in FIG. 5F. Initial measurements explored the dependence of pH$_L$ on Cl$^-$. After isolation, vesicles were bathed in KCl in the presence of 5 mM MgATP to activate the vH$^+$ATPase, and enable acidification and loading of Lysosensor. Lysosomes loaded with dye were bathed in 1, 3, 10, 30 and 100 mM Cl$^-$ and the pH was determined ratiometrically. Then Cl$^-$ was replaced with methylsulfonate, since other anions, such as gluconate, can permeate some Cl$^-$ channels (Mitchell et al., *J. Membr. Biol.* 150: 105-111 (1996)). Fluorescence ratios were converted to pH values using monensin and nigericin, as described. Lysosomes were also loaded with the Cl$^-$ sensitive dye MEQ (Woll et al. *Pflug. Arch. Eur. J. Physiol.* 432:486-493 (1996)) and the effect of external Cl$^-$ levels on intracellular concentration was determined. Ion concentrations are expressed as Cl$^-$ vs. epH to assess coupling (Hara-Chikuma et al., supra, 2005). The effects of general CF channel blocker 5-nitro-2-(3-phenyl-propylamino)-benzoate (NPPB, 30 µM (Jentsch et al. *Physiol. Rev.* 82:503-568 (2002)), along with those reported to have some specificity, such as DIDS (100 µM) and phloretin (300 µM) (Jentsch et al., supra, 2002; Sabirov et al., *J. Gen. Physiol.* 118:251-266 (2001)), and vH$^+$ATPase inhibitors bafliomycin A and concanamycin A (10 µg/ml) were tested at levels of Cl$^-$ found to give maximal acidification.

Effect of Alkalinizing Agents: The effect of 15 minutes exposure to tamoxifen (30 µM), and chloroquine (20 µM) on the relationship between pH and Cl$^-$ concentration was examined on isolated lysosomes. The effect of A2E was explored on lysosomes isolated from cells loaded with A2E for 4 weeks, as above. Cl$^-$ and H$^+$ ions were coupled in a 1:1 ratio. ClC-4 and ClC-5 proteins were recently identified as Cl$^-$/H$^+$ exchangers (Scheel et al., *Nature* 436:424-427 (2005); Picollo et al., *Nature* 436:420-423 (2005)). Deviation from a 1:1 ratio indicated a significant contribution from such an exchanger. However, since the exchangers were predicted to function on endosomes, with minimal contribution to lysosomes, such deviation was not a problem. To the contrary, the block by NPPB provided additional support for Cl$^-$ channels on the membrane, although the effects of phloretin and DIDS were difficult to predict (Sabirov et al., supra, 2001). These experiments also provide baseline pH levels to evaluate the direct effects of channel activation in the following example. Tamoxifen, chloroquine and A2E, all raise pH$_4$. The verification of Cl$^-$ as a rate-limiting step, combined with a drop in CF conductance in cells exposed to A2E, suggested that the reported decrease in vH$^+$ATPase activity evoked by A2E is secondary to a drop in Cl$^-$ conductance (Bergmann et al., supra, 2004).

Measurement of pH with the Lysosensor dye ensures that signal originates only from intact vesicles with the acidic pH required for dye loading. However, relative purity was further assessed by comparing the ratio of β-hexosaminidase to alkaline phosphodiesterase (Schutt et al., supra, 2002). If the CF conductance of the lysosomal membrane is constitutively low, characterizations are performed after activating the conductance with the catalytic subunit of protein kinase A (pK$_A$, see below). However, the findings presented in FIG. 5 indicated that the baseline activity was sufficient.

Experiment 5

Acidification of Lysosomes Through CFTR

Preliminary data demonstrated that the CFTR activators genistein and cAMP lowered pH$_L$, while the CFTR blocker glybenclamide raised it, and that transfection of RPE cells with CFTR decreases the alkalinization caused by tamoxifen (FIG. 5). As a result, an experiment was designed to confirm that the activation of CFTR could be used to acidify lysosomes in the RPE and to determine whether recently available specific compounds could restore lysosomal pH and increase outer segment clearance.

CFTR Activators: CFTR$_{Act-11}$ and CFTR$_{Act-16}$ were first identified by Verkman and colleagues (Ma et al., supra, 2002) and are now available through the ChemBridge Corp (San Diego, Calif.). CFTR$_{Act-11}$ activation of CFTR has an EC$_{50}$ of 3 µM and has no effect on cAMP levels, while CFTR$_{Act-16}$ activated CFTR with an EC$_{50}$ 0.5 µM and increased cAMP. Both compounds were applied at 0.1, 0.3, 1.3 and 10 µM in the presence, and absence, of a cAMP stimulating cocktail to verify the relationship to cAMP (500 µM cpt cAMP, 10 µM forskolin and 100 µM 3-isobutyl-1-methylxanthine (IBMX)). CFTR was also activated with apigenin (1, 5 and 25 µM (Caci et al., supra, 2003) and by the catalytic subunit of pK$_A$ (75 U/ml, Calbiochem), which activates CFTR directly (Berger et al., *J. Clin. Invest.* 88:1422-1431 (1991); Tilly et al., *J. Biol. Chem.* 267:9470-9473 (1992)). The ability of specific inhibitor, CFTR-172, to prevent the effect of the cAMP cocktail indicated whether all of the acidifications by cAMP require CFTR. Thus, CFTR-172 was applied at 10 µM, since that has previously produced a maximal block in RPE cells. Effective drugs were, therefore, validated on cells treated with A2E, and on outer segment clearance as described.

Role of ATP Release: The activation of CFTR can trigger release of ATP from RPE cells (Reigada et al., *Am. J. Physiol. Cell. Physiol.* 289: C617-C624 (2005)). Moreover, ATP and adenosine have been shown to acidify lysosomes. Thus, the effects of CFTR on pH$_L$ were expected to be mediated by extracellular purine signaling (FIG. 1). Cells were, therefore, exposed to the drugs found most effective at lowering pH$_L$ in the presence and absence of 10 U/ml apyrase and 100 µM αβmADP, since these compounds decreased the levels of ATP and adenosine (Zimmermann, In *Purinergic and Pyraminergic Signalling I: Molecular, Nervous and Urogenitary System Function*, Eds. Abbracchio and Williams, Springer-Verlag. New York, pp. 209-250 (2001)). Other identified antagonists, as identified in Example 1, were also used. A decrease in the acidification by CFTR activations implied that CFTR regulated pH$_L$ through release of ATP.

Localization of CFTR Action: Any effect of CFTR not due to ATP release could result from CFTR located on either the lysosomal membrane or on the plasma membrane. While the permeability of compounds specific for CFTR makes assignment to the plasma membrane difficult, their action on isolated lysosomes indicated a role for CFTR on the lysosomal membrane. The pH of isolated lysosomes was determined as above, but the effects of CFTR-172, CFTR$_{Act-11}$ and CFTR$_{Act-16}$ were quantified. Experiments were performed in the presence of the catalytic subunit of pK$_A$ and MgATP as necessary cytoplasmic constituents are not otherwise present. A change in the pH of isolated lysosomes by these highly specific compounds provided strong functional support to the localization of CFTR, and confirmed the report that the effect of cAMP on lysosomes requires Cl$^-$ (Van Dyke et al., *Biochem Biophys Res Comm.* 222:312-316 (1996)).

Transfection with CFTR: Transfection with plasmids containing the CFTR gene provided an additional degree of specificity in assessing the contribution of CFTR to pH$_L$. As done in the preliminary testing, transfection success was confirmed with Western blotting (FIG. 5D). The transfections were expanded in five ways: 1) The effect of the cAMP-stimulating cocktail on pH$_L$ of cells transfected with CFTR was measured to demonstrate an enhanced acidification of lysosomes, examining the effect on both tamoxifen-treated and untreated cells. 2) Cells were transfected with CFTR Δ508 as a control. CFTR Δ508 is the most common mutation in cystic fibrosis and provides defects in both trafficking and conductance that result in a large decrease in function (Yang et al., *Human Molecular Genetics.* 2:1253-1261 (1993)). Transfection with CFTR Δ508 controlled for the secondary effects of excess translational strain on the general state of the cells, and cells transfected with CFTR Δ508 were used to mimic mock-transfected cells. 3) The pH in isolated lysosomes challenged with tamoxifen was compared in cells transfected with CFTR, CFTR Δ508 and mock plasmid in the presence and absence of the catalytic subunit of $pK_A$ (in 100 mM solutions with 5 mM MgATP). 4) The rate of outer segment clearance was compared in cells transfected with wild type CFTR, CFTR Δ508 and control plasmids. 5) If the foregoing experiments indicated that the effects of CFTR were mediated by release of ATP, levels of ATP released from transfected and non-transfected cells challenged with hypotonic solution were compared using standard techniques (Reigada et al., supra, 2005).

Figure 7:
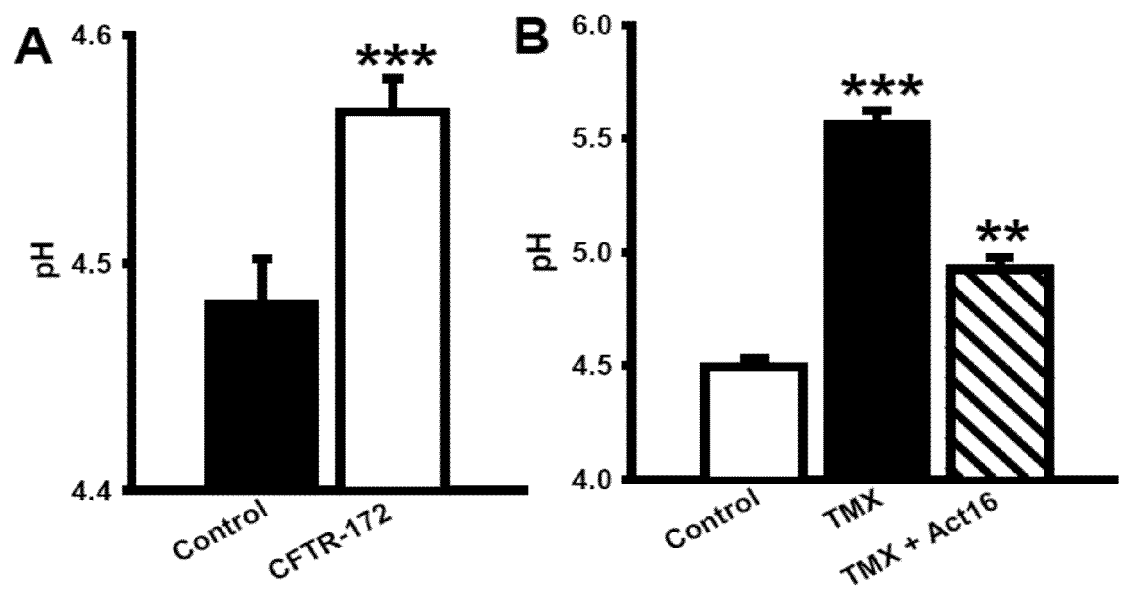
FIGS. 7A and 7B are graphs confirming the role of CFTR in acidifying lysosomes.

Results: As shown in FIGS. 7A and 7B, specific CFTR antagonist CFTR-172 (10 μM; n=32) increased lysosomal pH, verifying a role for CFTR in maintaining this pH. FIG. 7B shows that the newly developed CFTR activator $CFTR_{Act16}$ (Act16, 10 μM) restored acidity in cells exposed to 30 μM tamoxifen (TMX, n=6 for all). While the mechanisms underlying these effects remain to be determined, these results provided definitive confirmation of the role of CFTR. The relative effectiveness of $CFTR_{Act16}$ at lowering lysosomal pH also suggested that it offers a powerful new tool to restore lysosomal function. It also meant that modification of $pH_L$ by genistein, glybenclamide and cAMP in the preliminary data did not require an alternative mechanism, such as the $vH^+AT$-Pase. These results do not necessarily imply that patients with CF are more likely to show RPE dysfunction, since parallel channels are likely, particularly in non-transfected cells. Nor do they imply that A2E necessarily has a direct affect on CFTR molecules, although it does suggest possible routes to restore lysosomal pH. However, by using a functional assay, only the effect of transfection was detected if the extra CFTR activity contributed to lysosomal acidification.

Experiment 6

Effect of A2E on RPE $Cl^-$ Channel Expression

While CFTR provides an important target to acidify lysosomes, the development of additional approaches was enhanced by the molecular identification of CF channels altered in the disease. The addition of A2E to cells allowed the effect of a single parameter to be evaluated.

In this experiment, A2E were fed to flasks of confluent ARPE-19 cells 2-3 times per week. A2E without LDL was given at 14 nM, based upon results shown in FIG. 3A. RNA was collected at 0, 7, 14, 21 and 28 days and frozen. Once all RNA for a given trial was collected, it was reverse-transcribed in parallel and message levels were analyzed with quantitative PCR (QPCR). An approach used to successfully examine A3 adenosine receptors in retinal ganglion cells was employed (Zhang et al., *Mol. Vis.*, under revision). Transcript levels of ClC-3, ClC-4, ClC-5, ClC-6, ClC-7, VMD2, CliC-1, CliC-4, CFTR, VDAC1, VDAC3, and $vH^+ATPase$ at the different time points were compared by normalizing levels to those of the housekeeping gene GAPDH (see primer sequences in Methods section). Primers were chosen based on EST libraries of the RPE choroid (Wistow et al., supra, 2002; Ida et al., supra, 2004), or on detection with RT-PCR (Wills et al., supra, 2000; Weng et al., supra, 2002). No template controls were used to confirm specificity. Data was analyzed by examining the rise of SYBR green with thermocycle number using the delta-delta threshold crossing (ΔΔCt) approach. The reaction was performed in the Applied Biosystems ABI 7500 QPCR machine of the Penn Vision Research Center. Each reaction was performed in triplicate, with 4 independent flasks used for each time point. All products were sequenced and results were compared to published sequences with the Blast program (http://www.ncbi.nlm.nih.gov/BLAST). The measurement of $pH_L$ on cells treated in parallel ensured a tight correlation between changes in channel expression and changes in $pH_L$.

Thus, this experiment determined whether A2E alone is capable of altering expression of $Cl^-$ channels. Changes in expression levels that occurred before a rise in $pH_L$ was first detected suggested that the change could be causal, while modifications occurring after this point suggested a reactive response. The expression of ClC-7 was expected to decrease early on, since it is highly expressed in lysosomes, and is required for effective lysosomal clearance (Kasper et al., *EMBO J.* 24: 1079-1091 (2005); Kornak et al., *Cell* 104:205-215 (2001)). Changes in the level of VMD2 were also monitored with particular interest. The contribution of a channel depends upon its cellular location, and transcript levels do not indicate whether the channel is on the plasma or lysosomal membrane. The electrochemical gradient predicts that $Cl^-$ leaves the cell through channels on the plasma membrane, which in turn decreases the driving force for $Cl^-$ entry into the lysosomes. Thus, either increases or decreases in channel expression can be used to address the problem.

Experiment 7

Restoration of Lysosomal Acidity in $ABCA4^{-/-}$ mice

Figure 10:
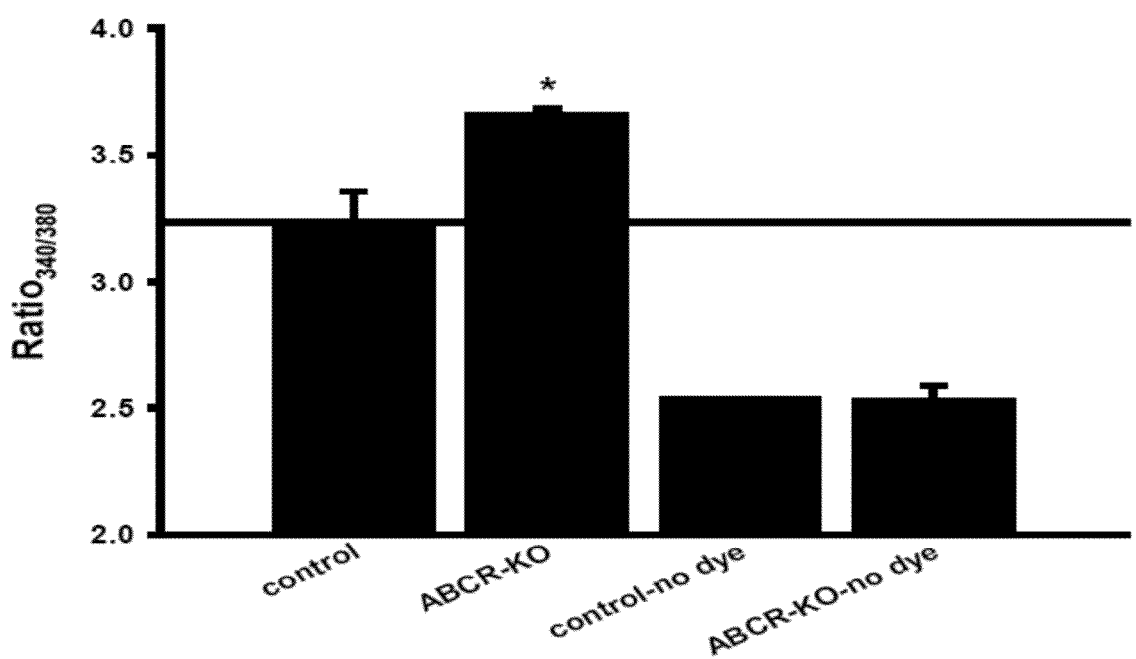
FIG. 10 is a bar graph showing that ABCA4 mice had an increased ratio of dye at 340/380 nm, consistent with an increased lysosomal pH, and consistent with the elevation found when A2E was added to ARPE-19 cells, showing that elevated pH occurs in an animal model of Stargardt's disease.

Because a paucity of molecular information about bovine $Cl^-$ channels restricted the experiments in Example 6 to the use of ARPE-19 cells, relevance of the findings to the in vivo state is further explored with $ABCA4^{-/-}$ mice to test the prediction that these manipulations identified in vitro in RPE cells are effective in restoring $pH_L$ acidity in vivo to lysosomes in an animal model of macular degeneration, and to identify the $Cl^-$ channels that were altered by the pathology. $ABCA4^{-/-}$ mice are missing the gene that is mutated in Stargardt's disease, and share many characteristics with the human form including increased A2E. As shown in FIG. 10, $ABCA4^{-/-}$ mice had an increased ratio of dye at 340/380 nm, consistent with an increased lysosomal pH, showing that elevated pH occurs in an animal model of Stargardt's disease, representative of a human response, and supporting the concept that lowering pH has direct implications for treating this disease, and by extension, for treating macular degeneration in both the model animal and in humans.

Figure 8:
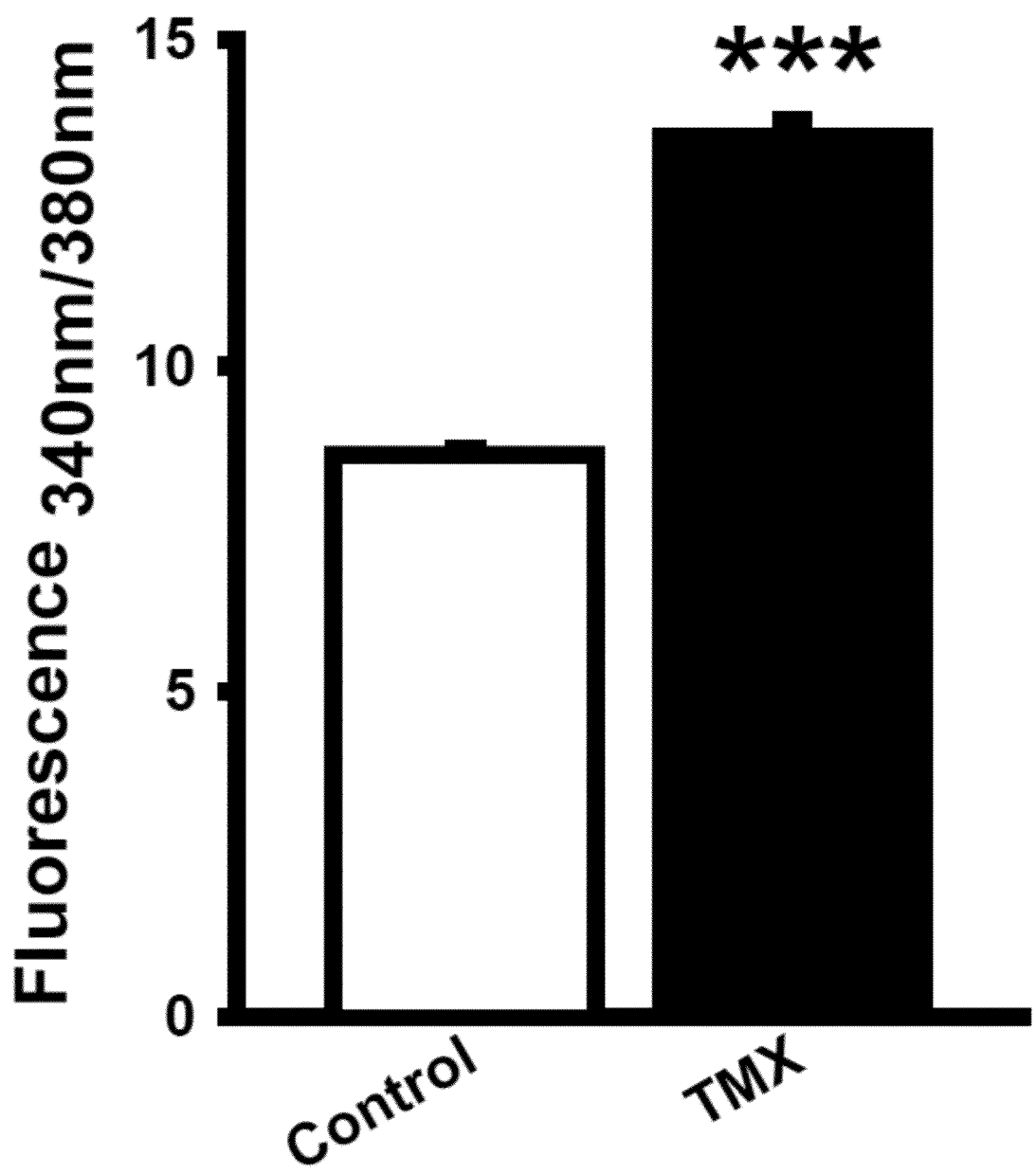
FIG. 8 is a graph showing measurements of lysosomal pH from fresh mouse RPE cells. Tamoxifen increased the 340/380 nm ratio in isolated mice RPE cells loaded with LysoSensor dye, consistent with an increase in pH as found in ARPE-19 cells. This demonstrates the feasibility of measurements from ABCA4$^{-/-}$ mice as described herein. ***p<0.001, n=6.
Figure 11:
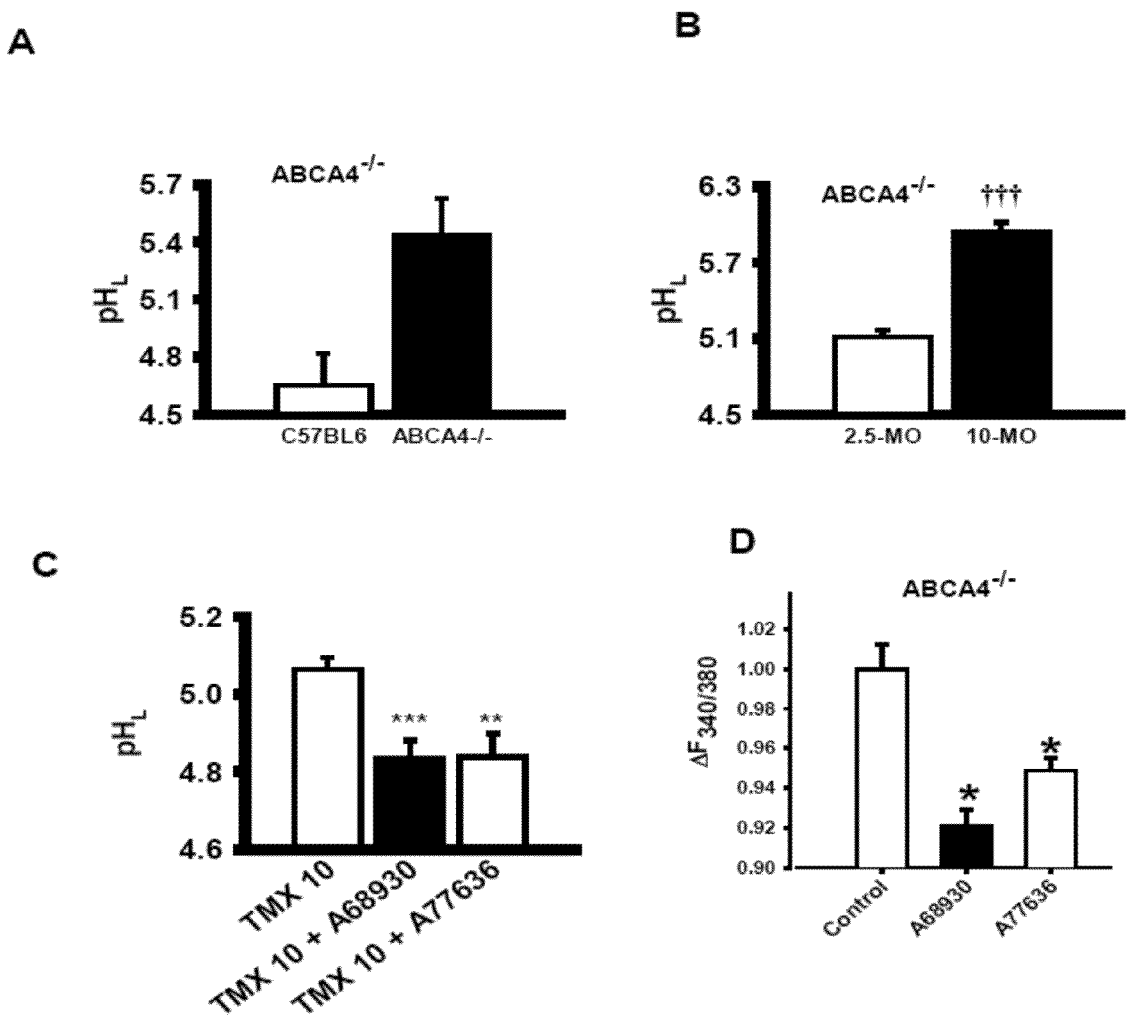
FIGS. 11A-11D are graphs showing the degree to which lysosomal pH is altered in ABCA4$^{-/-}$ mice, and restoration of lysosomal pH with D1-like dopamine receptor agonists.

Measurements of Lysosomal pH from Fresh Mouse RPE Cells: To verify the effectiveness of the $ABCA4^{-/-}$ model, the LysoSensor Yellow/Blue assay system was tested. LysoSensor Yellow/Blue dye was detected in freshly isolated mouse RPE cells, and first viewed as a brightfield image. The same field was exposed to fluorescence imaging, and excited at 360 nm (em: 510 nm). It was, thus, confirmed that the pigment does not interfere with fluorescence. As shown in FIG. 8, tamoxifen (30 μM) increased the 340/380 nm ratio in isolated mice RPE cells loaded with LysoSensor dye, consistent with the increase in pH found in ARPE-19 cells. This verified the feasibility of measurements from ABCA4$^{-/-}$ mice as an AMD model for experimental purposes. See, FIGS. 10 and 11.

Drugs that are identified in vitro as effective to lower pH$_L$ and restore rates of outer segment clearance will ultimately be confirmed in an animal model of AMD in vivo once details for efficient delivery to the posterior eye have been determined. The early onset of A2E accumulation makes the ABCA4$^{-/-}$ mouse an appropriate animal model for such an evaluation. However, initial studies will focus on the effect of the identified drugs.

Restoration of pH$_L$ in ABCA4$^{-/-}$ Mice: The ABCA4$^{-/-}$ mouse demonstrates a progressive accumulation of A2E in its RPE over 18 weeks when housed in 12 hour cyclic light of 25-30 lux (Mata et al., *Proc. Nat. Acad. Sci. USA* 97:7154-7159 (2000)). As a result, lysosomal pH increases early, and is measured in ABCA4$^{-/-}$ mice at 6, 12 and 18 weeks from RPE cells within 5 hours of sacrifice. As cell division may dilute the lysosomal contents, culturing these cells would diminish the effect on pH. However, the signal/noise from measurements of isolated cells with the plate reader is not acceptable. Instead, this signal is measured using the microscope-based imaging system, previously used successfully to measure Ca$^{2+}$ from freshly isolated retinal ganglion cells (Zhang et al., supra, 2005). This system was also used to record pH$_L$ from ARPE-19 cells before the high through-put system was developed. Initial readings are made with excitation at 340 and 380 nm in the absence of dye to record any autofluorescence for later subtraction. Next, cells are bathed in 5 µM Lysosensor dye for 5 minutes, followed by 15 minute wash. Baseline pH$_L$ is monitored for 3-5 minutes from cells in isotonic solution, after which CFTR activations and other compounds identified above to acidify lysosomes are added at appropriate concentrations. Once a new pH is reached, control solution is returned and the protocol repeated. The pH$_L$ is calibrated at the end of the experiment by perfusing with monensin/nigericin solutions. Parallel experiments are then performed on ABCA4$^{+/+}$ mice.

Assessment of ABCA4$^{-/-}$ Mice: The correct interpretation of the foregoing experiments depends upon assessment of genotype and phenotype. ABCA4$^{-/-}$ mice are bred and housed as described, using protocols established in the inventors' laboratory. PCR for the ABCA4 gene is performed on all mice used in this study, thus confirming the genotype. Several phenotypic changes have been characterized in ABCA4$^{-/-}$ mice including increases in levels of A2E levels, morphological changes surrounding Bruch's membrane and reduced magnitude of the ERG a-wave maximal response (Weng et al., *Cell.* 98:13-23 (1999); Mata et al. *Invest. Ophthalmol. Vis. Sci.* 42:1685-1690 (2001)). While it is neither practical nor necessary to repeat all assays, disease progression in the mice is determined as described by performing full field ERGs on age-matched wild type and knockout mice. The time course of the decrease in the a-wave is compared to that published by Travis and colleagues to orient the progression to other phenotypic changes. Thus, this experiment shows that pH$_L$ is elevated in ABCA4$^{-/-}$ mice, as compared to control animals, and that pharmacologic manipulation can restore the acidic pH to lysosomes of ABCA4$^{-/-}$ mice.

Experiment 8

Restoring Lysosomal pH

Having determined the damaging effect of age-increased pH in RPE cells, specifically in the effect on the ability of the lysosomes to clear spent photoreceptor outer segments and lipofusin via the Cl– channels, this experiment focused on how to restore optimal acidic pH to the affected lysosomes in the RPE, and to the identification of drugs or compounds that can achieve that effect and also prevent or restore the damage caused by the increased pH. Further this experiment evaluated the effect of D1-like dopamine receptors and D1-like dopamine receptor agonists, which led to the discovery that the D1-like agonists represent the most likely target. This is particularly relevant since the D1-like agonists are also currently being developed to treat Parkinson's disease.

Initially, the magnitude of the damage to lysosomes in RPE cells from the ABCA4$^{-/-}$ mouse model of Stargardt's disease was evaluated. In 6 trials of in RPE cells from ABCA4$^{-/-}$ mice (26 mice aged 216±28 days), as compared to 7 trials in cells from wild type mice (22 mice aged 215±32 days), increased pH$_L$ was clearly documented as rising from 4.65±0.17 to 5.43±0.19 units. See, FIG. 11A. This is precisely the range over which degradative lysosomal enzymes loose their function, further linking this defect to the accumulation of partially degraded material found in the RPE of patient's with Stargardt's disease. Lysosomal pH rose with age (FIG. 11B; 4 trials, 2 ABCA4$^{-/-}$ mice each; age shown in months (MO), consistent with both an age-dependent rise in A2E levels and the progression of Stargardt's disease (Mata et al., supra, 2001).

Recognizing that increased cAMP, and receptors coupled to the Gs protein that leads to elevated cAMP, led to the general conclusion that stimulation of the receptors coupled to the Gs proteins offered a treatment for restoring an acidic pH to the perturbed lysosomes, and thus, for improving degradative function. The most effective receptor is decided by numerous factors, including the availability and side-effects of appropriate agonists to the selected receptor. As such, D1-like dopamine receptors were selected as a particularly well-suited target.

There are five subtypes of dopamine receptors, D1, D2, D3, D4, and D5. D1 and D5 receptors are members of the D1-like family of dopamine receptors, whereas the D2, D3 and D4 receptors are members of the D2-like family. For the purposes of this invention, D1-like receptors are defined as D1 (D1α) and D5 (D1β) dopamine receptors. Both subtypes have similar affinities for "D1" receptor agonists and antagonists. See U.S. Pat. No. 6,469,141 and the references cited therein, wherein calcyon is defined as a D1 dopamine receptor activity modifying protein. Activation of the D1-like family receptors is coupled to the G protein Gαs, which subsequently activates adenylyl cyclase, increasing the intracellular concentration of the second messenger, cyclic adenosine monophosphate (cAMP). Increased cAMP in neurons is typically excitatory and can induce an action potential by modulating the activity of ion channels.

The dopamine receptors are a class of metabotropic G protein-coupled receptors that are prominent in the vertebrate central nervous system (CNS). The neurotransmitter dopamine is the primary endogenous ligand for dopamine receptors. These receptors have key roles in many processes, including the control of normal motor function and learning, as well as modulation of neuroendocrine signaling. Consequently, D1-like agonists are being developed to treat Parkinson's disease (Lewis et al., *CNS & Neurol. Disord. Drug Targets* 5:345-353 (2006); Mailman et al., *Curr. Op. Invest. Drugs* 2:1582-1591 (2001)). Abnormal dopamine receptor signaling and dopaminergic nerve function is implicated in several neuropsychiatric disorders.

The specific D1-like receptor agonist A77636 reduces Parkinsonian activity in a primate model of the disease when delivered orally (Smith et al., *J. Neur. Trans.* 109:123-140 (2002).). Chronic administration of D1-like receptor agonists has also been used as a long-term treatment for Parkinson's disease, demonstrating the relative safety of long-term use of the drug. Most of the known side effects are tolerable, or even beneficial, including increased cognitive ability (Stuchlik et al., *Behav. Br. Res.* 172:250-255 (2006)) and improved memory (Cai et al., *J. Pharm. Exp. Ther.* 283:183-189 (1997)).

In the present example, two specific D1-like agonists A77636 and A68930 were tested and shown to lower lysosomal pH in ARPE-19 cells (FIG. 11C). In 8 tests, dopamine D1-like receptor agonists A68930 (1 µM) and A77636 (1 µM) decreased lysosomal pH of ARPE-19 cells treated by tamoxifen (n=8). In addition, in 8 further tests, the two drugs also restored lysosomal pH in fresh RPE cells from ABCA4$^{-/-}$ mice (FIG. 11D; values are given as the ratio of light excited at 340 to 380 nm, an index of lysosomal pH. *=p<0.05, =p<0.01, *=p<0.001 vs control). The test mice were 11 months old, demonstrating that this treatment is effective, even on mice whose lysosomes have been damaged for an extended time. Thus, it is shown that the use of D1-like dopamine agonists is an effective treatment for both Stargardt's disease and macular degeneration. As the RPE cells contain D5 receptors (Versaux-Botteri et al., *Neurosci. Letts.* 237:9-12 (1997)), these will ultimately be a target. But since specific agents are not currently available, agents that stimulate D1 and D5 receptors are appropriate.

Experiment 9

Restoring Lysosomal pH$_L$ by Modulating P2X7 and/or P2Y12 Receptor Activity

Recognizing the significance of acidic conditions to maintain the optimal activity of the degradative enzymes in the lysosomes of the RPE cells, the lysosomal acidification is regulated by a series of membrane proteins, with proton delivery primarily mediated by the vacuolar proton pump (vH+ ATPase). Elevation of the lysosomal pH, results in impaired degradation of material by lysosomes, leading to pathological consequences both to the RPE cell and to the immediate area adjacent thereto. While re-acidification of pH-compromised lysosomes can rectify an elevated lysosomal pH in RPE cells and restore or enhance their essential degradative function, it has been further determined that stimulation of the P2X7 and P2Y12 receptors has a converse effect, thereby elevating lysosomal pH$_L$ in RPE cells. Consequently, as shown, administering "antagonists" to P2X7 receptor, or alternatively to the P2Y12 receptor, also effectively reacidifies lysosomal pH$_L$ in the RPE cells. As a result, as further demonstrated, administration of an antagonist either to the P2X7 receptor or to the P2Y12 receptor enhances degradative function of RPE lysosomes, and thus provides an alternative to treatment for macular degeneration, and/or offers an element in a combined treatment therefor.

There are many different receptors for ATP each with different effects. The endogenous agonist to the P2X7 receptor is ATP, while the endogenous P2Y12 agonist is ADP. The P2X7 receptor is unusual, and recent science suggests that the release site for ATP is close to the receptor. This enables endogenous specificity of action. ATP is not very stable endogenously due to the presence of many ecto-ATPases, and the P2X7 receptor requires large amounts of ATP to open, and thus localized release is logically acceptable.

As previously demonstrated, RPE cells constitutively release ATP, which extracellular enzymes then convert this to ADP (Mitchell, *J. Physiol* 534:193-202, (2001); Reigada et al., *Am. J. Physiol. Cell Physiol.* 289:C617-C624, 2005)). This allows for autostimulation of both P2X7 and P2Y12 receptors. A variety of pathological stimuli that can enhance the release of ATP (Mitchell et al., *Purinergic Signal* 4:101-107 (2008); Reigada et al., *J. Physiol.* 575: 707-720 (2006)), which then enhance the autostimulation of P2X7 and P2Y12 receptors, resulting in the increase in lysosomal pH$_L$, leading to reduced degradation of metabolic waste and to subsequent increased lipofuscin production and/or accumulation in the RPE cells. Consequently, by applying "antagonists" to the P2X7 and P2Y12 receptors ("P2X7 receptor-antagonist," and/or "P2Y12 receptor-antagonist"), the resulting pH elevation by endogenously released ATP is inhibited or prevented, thereby enhancing degradation of the metabolic waste by the lysosomes, reducing lipofuscin accumulation, and thus reducing the onset or progression of AMD.

Figure 12:
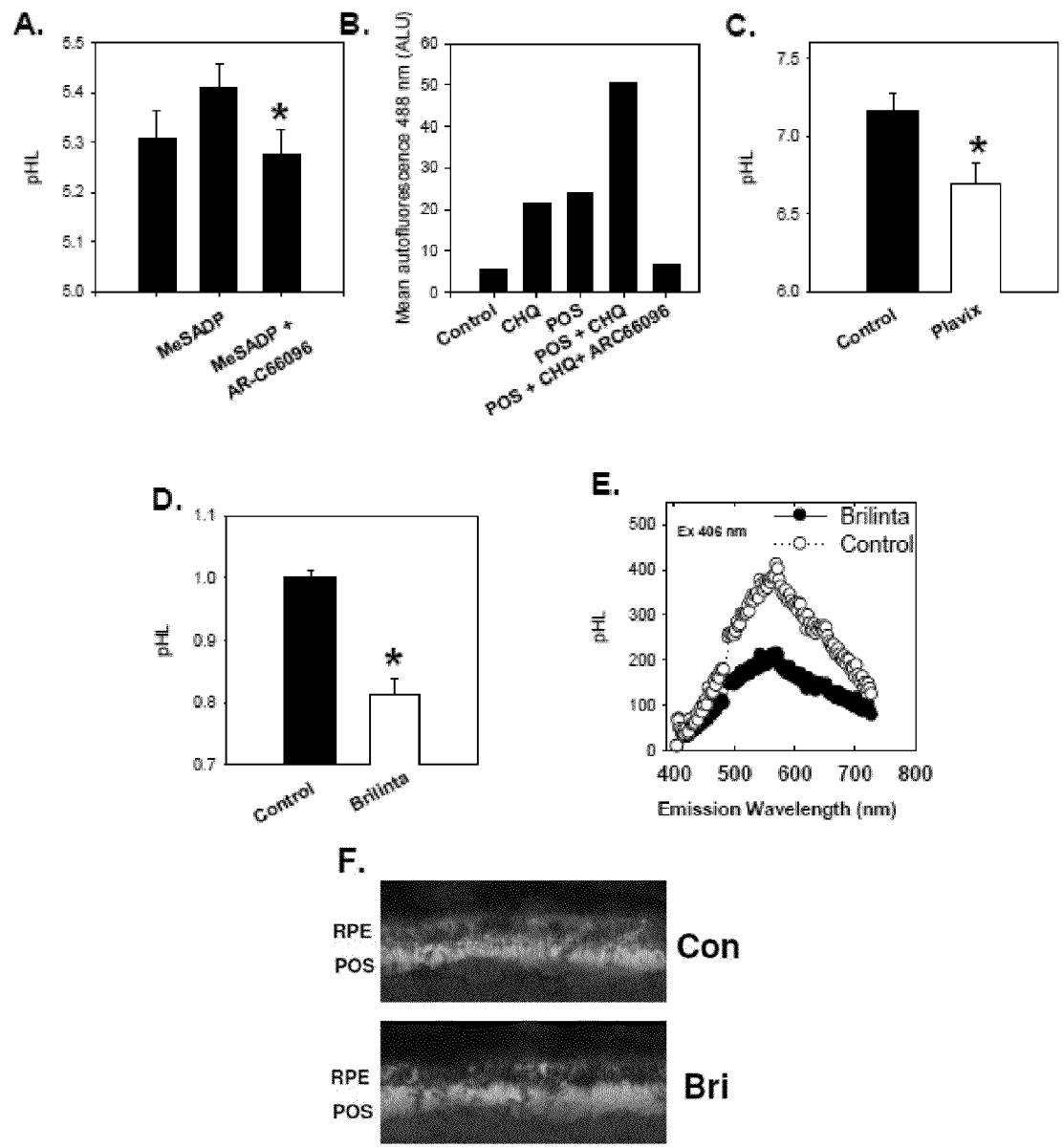
FIGS. 12A-12F show the effect of inhibiting the P2Y12 receptor. The graph of FIG. 12A shows that in ARPE-19 cells, stimulation of the P2Y12 receptor with agonist MeSADP elevated the lysosomal pHL, while the P2Y12 antagonist AR-C66096 inhibited increased pHL, restoring lysosomal acidity. The graph of FIG. 12B shows that outer-segment-associated autofluorescence in ARPE-19 cells is decreased in the presence of P2Y12 antagonist, AR-C66096, as seen in FACS analysis of autofluorescence readouts from ARPE-19 cells excited at 488 nm. The graph of FIG. 12C shows that lysosomal pHL in RPE cells from 9-11 month old ABCA4-/- mice was reduced by a single dose of a P2Y12 inhibitor (Plavix). The graph of FIG. 12D shows that Treatment with 20 month old ABCA4-/- mice with 12 ug/ml ticagrelor (Brilinta) in the water for 19 days reduced lysosomal pH of RPE cells. Data is expressed as ratio of pH sensor and proportional to lysosomal pH. The graph of FIG. 12E shows that treatment of 26 month old ABCA4-/- mice with 12 ug/ml ticagrelor (Brilinta) in the water for 4 days resulted in a decreased autofluorescence in RPE cells at various wavelengths observed when excited with a 406 nm laser. The images of FIG. 12F compare autofluorescence images in untreated ABCA4-/- mice (upper, Con)), with comparable animals treated with Brilinta (lower, Bri) in the water.

As shown in FIG. 12A, in ARPE-19 cells, stimulation of the P2Y12 receptor with agonist MeSADP elevated the lysosomal pH$_L$ while the P2Y12 antagonist AR-C66096 inhibited these actions and restored lysosomal acidity. AR-C66096 tetrasodium salt is available from Tocris Bioscience, Ellisville, Mo., as 2-(Propylthio) adenosine-5'-O-(β,γ-difluoromethylene) triphosphate tetrasodium salt, or $C_{14}H_{18}F_2N_5Na_4O_{12}P3S$, also referred to as FPL 66096, or ARL 66096, Cat. No. 3321. As the P2Y12 receptor decreases cellular cAMP, this effect is consistent with the ability of cAMP to acidify lysosomes.

Outer-segment-associated autofluorescence in ARPE-19 cells was decreased in the presence of P2Y12 antagonist AR-C66096 as seen in FIG. 12B. FACS analyses were conducted on auto-fluorescence readouts from ARPE-19 cells excited at 488 nm. The cells were treated for 7 days with 10 µM chloroquine (CHQ), resulting in visibly increased autofluorescence. As previously shown above, this increases lysosomal pH$_L$, presumably the increased fluorescence reflects a perturbation of autophagy (or "autophagocytosis"), which is a catabolic process involving the degradation of a cell's own components through the lysosome. To maintain a balance between the synthesis, degradation, and subsequent recycling of cellular products there are a variety of autophagic responses, but all involve degradation of intracellular components via the lysosome. Typically, autophagy involves the formation of a membrane around a targeted region of the cell, separating the contents from the rest of the cytoplasm, and then the resultant vesicle fuses with a lysosome and the contents are subsequently degraded. Increased autofluorescence is also observed when cells are fed with photoreceptor outer segments (POS) for 7 days, which likely represents an increase in partially degraded outer segment material.

Autofluorescence is, therefore, indicative of incomplete degradation of material by the lysosomes, resulting in an analogous autofluorescence is frequently observed in macular degeneration. In effect, age related macular degeneration is the pathological consequence of failed housekeeping by the RPE cell, whereby failure of the lysosomes to completely degrade the ingested material, even in part, leads to accumulation within the RPE cell of autofluorescent lipoprotein aggregates termed lipofuscin. In turn, over time the RPE cell expels some of the aggregates into the subretinal space leading to the pathological sequence recognized as age related macular degeneration (AMD). But fortunately, the concentration of retained material can be quantified by the intensity of an autofluorescent signal emitted by the RPE cell. Thus the demonstration that RPE cells exposed to photoreceptor outer segments for 7 days ingested the outer segments and then developed autofluorescence indicative of impaired degradation provides compelling evidence that the pathological sequence can be interrupted, offering correction options as both in prevention and treatment of AMD, as well as pharmacologically-enhanced clearance of the ingested material.

The effects of the two treatments on autofluorescence were additive (POS+CHQ). However, antagonizing P2Y12 receptor with AR-C66096 reduced this enhanced auto-fluorescence to near control levels, indicating that antagonizing the P2Y12 receptor enhances the breakdown of unwanted autofluorescent material in RPE cells. The ability of the antagonists to reduce autofluorescence in absence of an additional agonist implies that ATP released from the cells is sufficient to stimulate the P2Y12 receptor and slow lysosomal digestion, thus increasing autofluorescence. Consequently, by applying exogenous antagonists to the P2Y12 receptors, the resulting pH elevation by endogenously released ATP is inhibited or prevented, thereby enhancing degradation of the metabolic waste by the lysosomes. This reduces autofluorescent lipofuscin accumulation, and thus reduces the onset or progression of AMD.

As seen in FIG. 12C, the lysosomal $pH_L$ in RPE cells from 9-11 month old ABCA4−/− mice was reduced by a single dose of a P2Y12 inhibitor. In this example the selected P2Y12 inhibitor was clopidogrel (commercially available as Plavix), but the invention need not be so limited, and other P2Y12 inhibitors, such as AR-C66096, may be used. The clopidogrel was given orally at 50 mg/kg and the pH measured from RPE cells that were removed 4 hrs later.

Similarly, treatment of 20 month old ABCA4−/− mice with 12 ug/ml ticagrelor (Brilinta) in the water for 19 days reduced lysosomal pH of RPE cells. Resulting data, as shown by the graph in FIG. 12D, is expressed as ratio of pH sensor and proportional to lysosomal pH. This is important because the mice used in the experiment are representative old and diseased animals, and the drug was put in the water at levels used in patients clinically.

Treatment of 26 month old ABCA4−/− mice with 12 ug/ml ticagrelor (Brilinta) in the water for 4 days resulted in a decreased autofluorescence in RPE cells at various wavelengths observed when excited with a 406 nm laser. See. FIG. 12E. The decreased autofluorescence is evidence of enhanced degradative activity to clear intracellular aggregates.

Finally, as recorded in the photographic images of FIG. 12F, autofluorescence in untreated ABCA4−/− mice (upper, Con)) were compared with those treated with Brilinta (lower, Bri) in the water. Again, this demonstrates that oral drug treatment is effective against older mice. The decrease in autofluorescence suggests it may be of considerable use as a treatment to prevent, reduce and treat AMD.

Other known compositions that inhibit the P2Y12 receptor, include cangrelor, ticagrelor (tradename Brilinta developed by AstraZeneca, and safely used in many clinical trials), prasugrel (tradename Effient, a.k.a Effient, Daiichi Sankyo Co.), ticlopidine (tradename Ticlid) and elinogrel (PRT-060128). All are available from AstraZeneca. At least one of the identified antagonists is selected, and dosage can be determined by one skilled in the art in light of the data provided in the foregoing experiments and results shown in the Figures, since these antagonists operate in the manner described herein to inhibit the action of the P2Y12 receptors.

Turning to FIG. 13A, again in ARPE-19 cells, stimulation of the P2X7 receptor with agonist BzATP resulted in elevation of the lysosomal $pH_L$, while the P2X7 antagonists A438079 (from Tocris) and BBG prevented this rise. A438079 is also available from Tocris Bioscience, Ellisville, Mo., as 3-[[5-(2,3-Dichlorophenyl)-1H-tetrazol-1-yl]methyl]pyridine hydrochloride salt, or $C_{13}H_9Cl_2N_5 \cdot HCl$, Cat. No. 2972, which is devoid of activity at other P2 receptors. BBG, now available for ophthalmic use, is $C_{47}H_{48}N_3NaO_7S_2$, also known as Acid blue 90, or Coomassie® Brilliant Blue G from Sigma-Aldrich (St. Louis, Mo.) and ILM-Blue manufactured by DORC (Dutch Ophthalmic Research, The Netherlands). Other known compositions that are also useful to inhibit the P2X7 receptors (antagonists for the P2X7 receptor), e.g., A740003 (18/40 nM), AZ-10606120 (19/1.4 nM), AZ-11645373 (6 nM human), KN-62 (15 nM human), A-839977, A-74003, NF279, MRS 2159, all commercially available from Tocris; A-847227 available from Abbott Laboratories (Abbott Park, Ill.); GSK314181A available from GalaxoSmithKline Pharmaceuticals (Middlesex, United Kingdom); AZD-9056 available from AstraZeneca (Wilmington, Del.); CE-224535 available from Pfizer, Inc. (New York, N.Y.); AF-4025 and AFC-5128, available from Affectis Pharmaceuticals AG (Martinsried, Germany); EVT 401 available from Evotec (Hamburg, Germany); and MRS2306 and MRS2540 available from the National Institutes of Health (NIH, Rockville, Md.). At least one of the identified antagonists is selected, and dosage can be determined by one skilled in the art in light of the data provided in the foregoing experiments and results shown in the Figures, since these antagonists operate in the manner described herein to inhibit the action of the P2X7 receptors.

Figure 13:
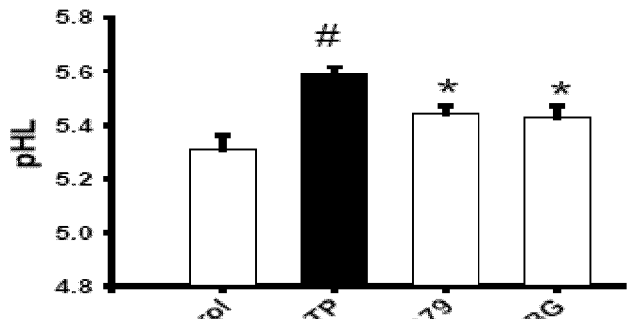
FIGS. 13A-13C are graphs showing the effect of inhibiting the P2X7 receptor.
Figure 13:
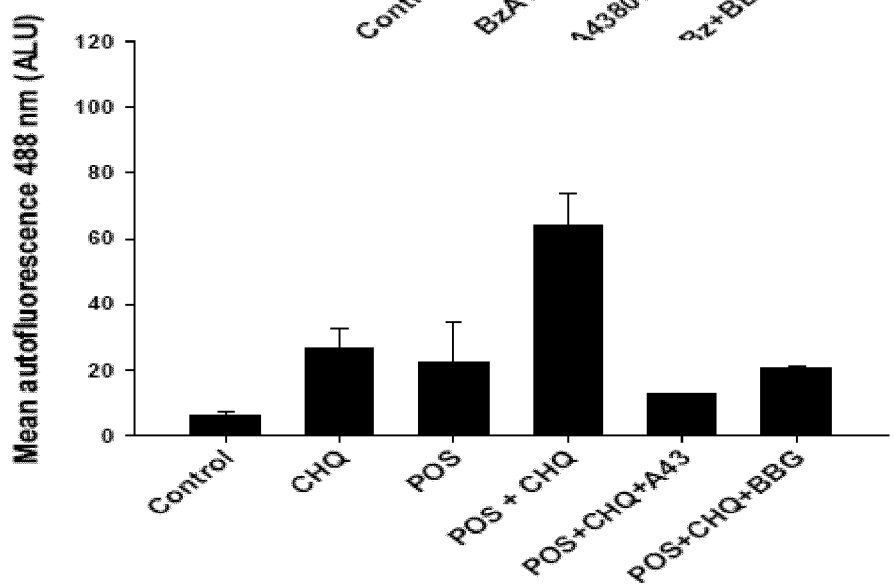
Figure 13:
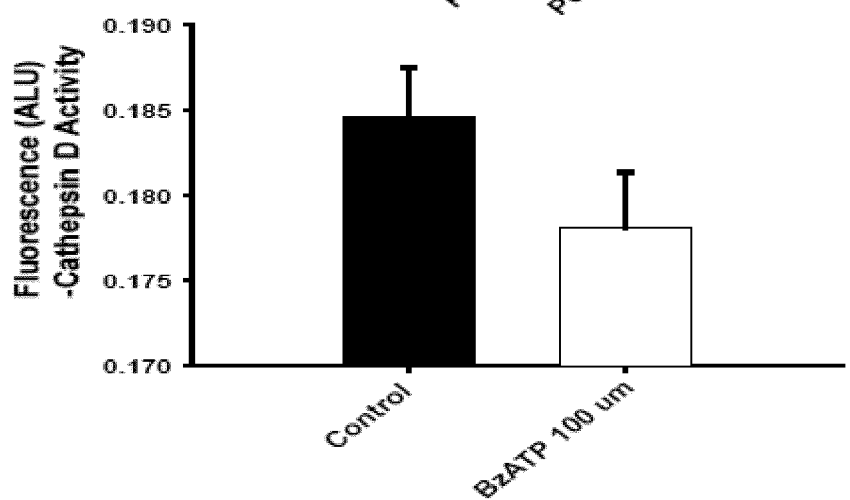

As above, outer-segment-associated autofluorescence in ARPE-19 cells is decreased in the presence of P2X7 antagonists (FIG. 13B). FACS analyses were conducted of autofluorescence readouts from ARPE-19 cells excited at 488 nm. Further treating the cells for 7 days with 10 μM chloroquine (CHQ) increased autofluorescence; corresponding to the previously shown increase in lysosomal $pH_L$ and presumably the increase fluorescence reflects a perturbation of autophagy. Feeding the cells with photoreceptor outer segments (POS) for 7 days also demonstrated increased autofluorescence as above, likely representing an increase in partially degraded outer segment material. The effects of these two treatments on auto-fluorescence were also additive (POS+CHQ). However, antagonizing P2X7 receptor with A438079 or BBG reduced this enhanced autofluorescence, also indicating that antagonizing the P2X7 receptor enhances the breakdown of autofluorescent material in RPE cells. Thus the ability of P2X7 antagonists to reduce autofluorescence offers clinical benefit as autofluorescence in the RPE, when associated with failed cellular digestion, is a clinical hallmark of macular degeneration.

In FIG. 13C, it is shown that BzATP reduced lysosomal enzyme activity. Cathepsin-D activity in ARPE-19 cells, monitored with a fluorescent reporter, was visibly decreased by the addition of BzATP. Cathepsin D is the major lysosomal protease responsible for degrading photoreceptors in the RPE, and thus changes to cathepsin D activity reflect the ability of the lysosomes to successfully degrade (dispose of) phagocytosed outer segments. This shows that degradative activity is impaired by stimulation or increase of the P2X7 receptor, which is consistent with the findings that stimulating the P2X7 receptor increases the lysosomal $pH_L$, leading to reduced degradation of metabolic waste and to a subsequent increase in lipofuscin production and/or accumulation in the RPE cells. Consequently, by applying exogenous antagonists to the P2X7 and P2Y12 receptors (i.e., P2X7 receptor-antagonist, and/or P2Y12 receptor-antagonist), the resulting pH elevation by endogenously released ATP is inhibited or prevented, thereby enhancing degradation of the metabolic waste by the lysosomes, reducing autofluorescent lipofuscin accumulation, and thus reducing the onset or progression of AMD.

Figure 14:
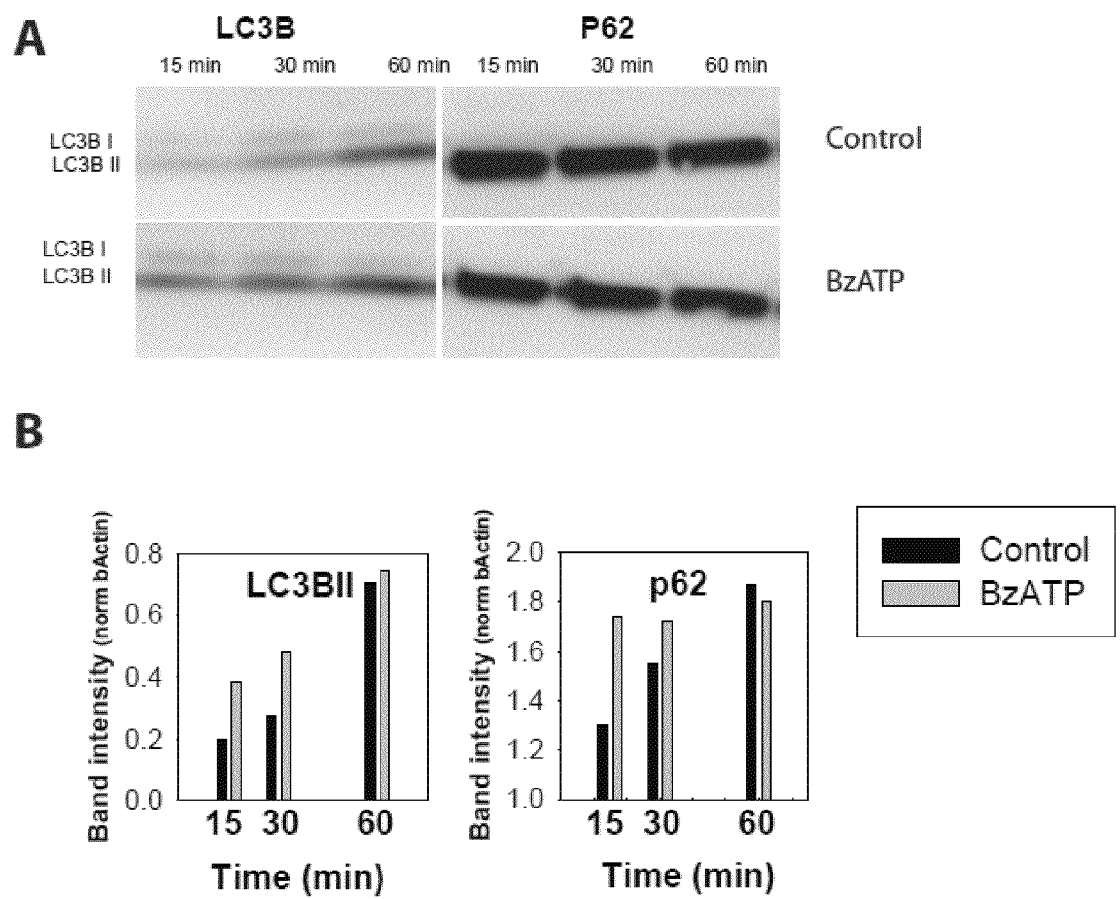
FIGS. 14A and 14B show that stimulation of P2X7 receptor modifies autophagy.

Additional evidence to support the beneficial effects of antagonizing the P2X7 receptor is indicated in FIG. 14. While the RPE cells must degrade phagocytosed outer segments, they must also degrade and dispose of their own waste material through a process termed autophagy. The ability of P2X7 receptor stimulation to rapidly raise levels of autophagy markers LC3BII and p62 are consistent with the effects of raising lysosomal pH, for they imply that lysosomal alkalinization prevents the RPE cell from degrading material from autopagic vesicles containing p62 or tagged with LC3BII. (See, Kabeya, Y., et al., "LC3, a mammalian homolog of yeast Apg8p, is localized in autophagosome membranes after processing." *EMBO J.,* 22:4577-4577 (2003); Moscat, J. and Diaz-Meco, M. T. (2009) "p62 at the Crossroads of Autophagy, Apoptosis, and Cancer," *Cell* 137:1001-1004 (2009)). Therefore, these responses demonstrate that overstimulation of the P2X7 receptor interferes with the cells basic housekeeping.

Consequently, the foregoing results demonstrate that modulating the P2X7 and P2Y12 receptors, more specifically antagonizing the P2X7 receptor, and by extension the P2Y12 receptor, beneficially enhances the RPE cell's ability to prevent, reduce and/or treat accumulation of unwanted debris. Accordingly administration of antagonist to either the P2X7 receptor or the P2Y12 receptor enhances degradative function of RPE lysosomes, and as a result results in the acidification, or re-acidification, of pH-compromised lysosomes to rectify elevated lysosomal $pH_L$ in the cells. Thus the essential degradative function of the lysosome is restored or enhanced, providing a treatment for or prevention of macular degeneration.

In sum, by combining a mechanistic analysis of lysosomal acidification with a high through-put evaluation of this pharmacologic approach, specific compounds that lower lysosomal pH and increase the activity of degradative enzymes have been identified, and the findings are applied to animal models. Thus, methods are provided in the present invention for slowing the progression of AMD by restoring an optimal acidic pH to compromised lysosomes in the RPE, and an effective treatment is provided for reversing macular degeneration and the damaging effects of abnormally elevated $pH_L$, particularly as found in AMD and in Stargardt's disease.

The disclosure of each patent, patent application and publication cited or described in this document is hereby incorporated herein by reference, in its entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method of treating age-related macular degeneration (AMD) in a patient subject to or symptomatic of age-related macular degeneration (AMD), the method comprising administering to a patient at least one P2X7 receptor antagonist selected from the group consisting of A438079, (3-[[5-(2,3-dichlorophenyl)-1H-tetrazol-1-yl]methyl]pyridine hydrochloride salt, C13H9C12N5•HC1, BBG for ophthalmic use, C47H48N3NaO7S2,Acid blue 90, Coomassie® Brilliant Blue G, A740003(18/40 nM), AZ-10606120(19/1.4nM); AZ-1645373(6 nM human); KN-62(15 nM human), A-839977, A-847227, AZ-116453743, GSK314181A, AFC-5128, AZD-9056, CE-224535, AF-4025, EVT 401, MRS 2159, MRS2306 and MRS 2540, to inhibit P2X7 receptor activity, thereby acidifying lysosomal pH ($pH_L$) in the retinal pigment epithelium (RPE) cell(s) of the patient's eyes.

2. The method of claim 1, further comprising decreasing or preventing a damaging accumulation of lipofuscin or waste products in the RPE by acidifying lysosomal $pH_L$.

3. The method of claim 2, further comprising enhancing degradation by the lysosome by acidifying lysosomal $pH_L$, thereby enhancing disposal of phagocytized photoreceptor outer segments and enzymatically decreasing or inhibiting damaging accumulations of lipofuscin or precursors thereof, and metabolic waste in the RPE.

4. The method of claim 2, wherein the P2X7 receptor-antagonist is administered to the RPE cells in an amount sufficient to decrease the $pH_L$ or restore acidity of lysosomes in the RPE cell.

5. The method of claim 2, further comprising restoring or preserving photoreceptor normality and photoreceptor activity to the eye of the patient subject to, or symptomatic of lipofuscin accumulation in or adjacent to the RPE cells.

6. A method of treating age-related macular degeneration (AMD) in a patient subject to or symptomatic of age-related macular degeneration (AMD), the method comprising administering to a patient at least one P2Y12 receptor-antagonist selected from the group consisting of AR-C66096 (C14H18F2N5Na4O12P3S), AR-2-(Propylthio) adenosine-5'-O-((β,γ-difluoromethylene) triphosphate tetrasodium salt, cangrelor, ticagrelor (Brilinta), prasugrel (Effient), ticlopidine (Ticlid) and elinogrel (PRT-060128) to inhibit P2Y12 receptor activity, thereby acidifying lysosomal pH ($pH_L$) in the retinal pigment epithelium (RPE) cell(s) of the patient's eyes.

7. The method of claim 6, further comprising decreasing or preventing a damaging accumulation of lipofuscin or waste products in and adjacent to the RPE by acidifying lysosomal $pH_L$.

8. The method of claim 7, further comprising enhancing degradation by the lysosome by acidifying lysosomal $pH_L$, thereby enhancing disposal of phagocytized photoreceptor outer segments and enzymatically decreasing or inhibiting damaging accumulations of lipofuscin or precursors thereof, and metabolic waste in the RPE.

9. The method of claim 7, wherein the P2Y12 receptor-antagonist is administered to the RPE cell in an amount sufficient to decrease the $pH_L$ or restore acidity of lysosomes in the RPE cell.

10. The method of claim 7, further comprising restoring or preserving photoreceptor normality and photoreceptor activity to the eye of the patient subject to, or symptomatic of lipofuscin accumulation in or adjacent to the RPE cells.

* * * * *

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial
<220> FEATURE:
<223> OTHER INFORMATION: Chemically Synthesized

<400> SEQUENCE: 1
atggggcctt gatggsagca c                                                 21

<210> SEQ ID NO 2
<211> LENGTH: 20
<212> TYPE: DNA
<213> ORGANISM: Artificial
<220> FEATURE:
<223> OTHER INFORMATION: Chemically Synthesized

<400> SEQUENCE: 2
ggcgaagcat ccccattagg                                                   20

<210> SEQ ID NO 3
<211> LENGTH: 20
<212> TYPE: DNA
<213> ORGANISM: Artificial
<220> FEATURE:
<223> OTHER INFORMATION: Chemically Synthesized

<400> SEQUENCE: 3
tgctttagtg gctgcatttg                                                   20

<210> SEQ ID NO 4
<211> LENGTH: 20
<212> TYPE: DNA
<213> ORGANISM: Artificial
```

<220> FEATURE:
<223> OTHER INFORMATION: Chemically Synthesized

<400> SEQUENCE: 4
ccagaacggg atactttcca                                        20

<210> SEQ ID NO 5
<211> LENGTH: 22
<212> TYPE: DNA
<213> ORGANISM: Artificial
<220> FEATURE:
<223> OTHER INFORMATION: Chemically Synthesized

<400> SEQUENCE: 5
gcatactgct gggaagaagc aa                                     22

<210> SEQ ID NO 6
<211> LENGTH: 27
<212> TYPE: DNA
<213> ORGANISM: Artificial
<220> FEATURE:
<223> OTHER INFORMATION: Chemically Synthesized

<400> SEQUENCE: 6
gactcgacat aggctgcctt ccgagtc                                27

<210> SEQ ID NO 7
<211> LENGTH: 18
<212> TYPE: DNA
<213> ORGANISM: Artificial
<220> FEATURE:
<223> OTHER INFORMATION: Chemically Synthesized

<400> SEQUENCE: 7
ctcccacggg tgttcaag                                          18

<210> SEQ ID NO 8
<211> LENGTH: 19
<212> TYPE: DNA
<213> ORGANISM: Artificial
<220> FEATURE:
<223> OTHER INFORMATION: Chemically Synthesized

<400> SEQUENCE: 8
caagcctctc tttcccagg                                         19

<210> SEQ ID NO 9
<211> LENGTH: 22
<212> TYPE: DNA
<213> ORGANISM: Artificial
<220> FEATURE:
<223> OTHER INFORMATION: Chemically Synthesized

<400> SEQUENCE: 9
ggtgattctg aaccttgcct ca                                     22

<210> SEQ ID NO 10
<211> LENGTH: 22
<212> TYPE: DNA
<213> ORGANISM: Artificial
<220> FEATURE:
<223> OTHER INFORMATION: Chemically Synthesized

<400> SEQUENCE: 10
tcctcttgtt agccctccac ct                                     22

```
<210> SEQ ID NO 11
<211> LENGTH: 20
<212> TYPE: DNA
<213> ORGANISM: Artificial
<220> FEATURE:
<223> OTHER INFORMATION: Chemically Synthesized

<400> SEQUENCE: 11
ccgaaaactt actggagaac                                                     20

<210> SEQ ID NO 12
<211> LENGTH: 20
<212> TYPE: DNA
<213> ORGANISM: Artificial
<220> FEATURE:
<223> OTHER INFORMATION: Chemically Synthesized

<400> SEQUENCE: 12
gatcatccag gaatcaccaa                                                     20

<210> SEQ ID NO 13
<211> LENGTH: 21
<212> TYPE: DNA
<213> ORGANISM: Artificial
<220> FEATURE:
<223> OTHER INFORMATION: Chemically Synthesized

<400> SEQUENCE: 13
cagcaatggt tcaagtggca a                                                   21

<210> SEQ ID NO 14
<211> LENGTH: 21
<212> TYPE: DNA
<213> ORGANISM: Artificial
<220> FEATURE:
<223> OTHER INFORMATION: Chemically Synthesized

<400> SEQUENCE: 14
gggctctgag agtttgtgct c                                                   21

<210> SEQ ID NO 15
<211> LENGTH: 21
<212> TYPE: DNA
<213> ORGANISM: Artificial
<220> FEATURE:
<223> OTHER INFORMATION: Chemically Synthesized

<400> SEQUENCE: 15
ggcatggtca agatagatct g                                                   21

<210> SEQ ID NO 16
<211> LENGTH: 22
<212> TYPE: DNA
<213> ORGANISM: Artificial
<220> FEATURE:
<223> OTHER INFORMATION: Chemically Synthesized

<400> SEQUENCE: 16
gtataagcat gacctgaagt ag                                                  22

<210> SEQ ID NO 17
<211> LENGTH: 20
<212> TYPE: DNA
<213> ORGANISM: Artificial
<220> FEATURE:
<223> OTHER INFORMATION: Chemically Synthesized
```

```
<400> SEQUENCE: 17
ggagattgac gccaacactt                                              20

<210> SEQ ID NO 18
<211> LENGTH: 18
<212> TYPE: DNA
<213> ORGANISM: Artificial
<220> FEATURE:
<223> OTHER INFORMATION: Chemically Synthesized

<400> SEQUENCE: 18
acgggcatag gcgttctt                                                18

<210> SEQ ID NO 19
<211> LENGTH: 20
<212> TYPE: DNA
<213> ORGANISM: Artificial
<220> FEATURE:
<223> OTHER INFORMATION: Chemically Synthesized

<400> SEQUENCE: 19
acacagctgg gctggacata                                              20

<210> SEQ ID NO 20
<211> LENGTH: 24
<212> TYPE: DNA
<213> ORGANISM: Artificial
<220> FEATURE:
<223> OTHER INFORMATION: Chemically Synthesized

<400> SEQUENCE: 20
aacttcctct gagagacacc ttca                                         24

<210> SEQ ID NO 21
<211> LENGTH: 20
<212> TYPE: DNA
<213> ORGANISM: Artificial
<220> FEATURE:
<223> OTHER INFORMATION: Chemically Synthesized

<400> SEQUENCE: 21
ggtccactgg cccatacaca                                              20

<210> SEQ ID NO 22
<211> LENGTH: 21
<212> TYPE: DNA
<213> ORGANISM: Artificial
<220> FEATURE:
<223> OTHER INFORMATION: Chemically Synthesized

<400> SEQUENCE: 22
cgtaggtgat ttgcaaccac a                                            21
```